United States Patent
Foo et al.

(10) Patent No.: US 12,286,460 B2
(45) Date of Patent: Apr. 29, 2025

(54) POLYPEPTIDE AND RELATED PRODUCTS, METHODS AND USES

(71) Applicant: AGENCY FOR SCIENCE, TECHNOLOGY AND RESEARCH, Singapore (SG)

(72) Inventors: Roger Sik Yin Foo, Singapore (SG); Vinh Dang Do, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 797 days.

(21) Appl. No.: 17/430,484

(22) PCT Filed: Feb. 12, 2020

(86) PCT No.: PCT/SG2020/050069
§ 371 (c)(1),
(2) Date: Aug. 12, 2021

(87) PCT Pub. No.: WO2020/167252
PCT Pub. Date: Aug. 20, 2020

(65) Prior Publication Data
US 2022/0227822 A1    Jul. 21, 2022

(30) Foreign Application Priority Data
Feb. 12, 2019 (SG) .............. 10201901195V

(51) Int. Cl.
*C07K 14/47* (2006.01)
*A61K 38/00* (2006.01)
*A61K 47/00* (2006.01)
*A61P 9/00* (2006.01)
*C12N 15/63* (2006.01)
*C12Q 1/6883* (2018.01)

(52) U.S. Cl.
CPC .............. *C07K 14/47* (2013.01); *A61K 47/00* (2013.01); *A61P 9/00* (2018.01); *C12N 15/63* (2013.01); *A61K 38/00* (2013.01); *C12Q 1/6883* (2013.01)

(58) Field of Classification Search
None
See application file for complete search history.

(56) References Cited

U.S. PATENT DOCUMENTS
2003/0176681 A1    9/2003   Feng et al.

FOREIGN PATENT DOCUMENTS
WO    2018111193 A1    6/2018

OTHER PUBLICATIONS

Zhang et al. (Physiol Genomics 44: 1133-1140, 2012) (Year: 2012).*
See et al. (Nature Communications 8, Article No. 225, 2017) (Year: 2017).*
Mullin et al. "Genetic regulatory mechanisms in human osteoclasts suggest a role for the STMP1 and DCSTAMP genes in Paget's disease of bone." Scientific Reports 9(1): 1-7 (2019).
Niculescu et al. "Precision medicine for suicidality: from universality to subtypes and personalization." Molecular Psychiatry 22(9): 1250-1273 (2017).
Rosca et al. "Mitochondria in heart failure." Cardiovascular Research 88(1): 40-50 (2010).
Zhang et al. "Functional prediction and physiological characterization of a novel short trans-membrane protein 1 as a subunit of mitochondrial respiratory complexes." Physiological Genomics 44(23): 1133-1140 (2012).

* cited by examiner

*Primary Examiner* — Sergio Coffa
(74) *Attorney, Agent, or Firm* — NIXON PEABODY LLP; Mark J. Fitzgerald; Jeanne N. Jodoin

(57) ABSTRACT

The invention relates to an isolated polypeptide encoded by Sghrt and related uses. In addition, methods of assessing a heart function, treating impaired heart function by inhibiting Sghrt, identifying a potential drug for treating impaired heart function, and dedifferentiating and/or proliferating a heart cell by inhibiting Sghrt are claimed.

5 Claims, 12 Drawing Sheets
Specification includes a Sequence Listing.

SEQUENCE LISTING

```
<160> NUMBER OF SEQ ID NOS: 26

<210> SEQ ID NO 1
<211> LENGTH: 47
<212> TYPE: PRT
<213> ORGANISM: Homo sapiens

<400> SEQUENCE: 1

Met Leu Gln Phe Leu Leu Gly Phe Thr Leu Gly Asn Val Val Gly Met
1               5                   10                  15

Tyr Leu Ala Gln Asn Tyr Asp Ile Pro Asn Leu Ala Lys Lys Leu Glu
            20                  25                  30

Glu Ile Lys Lys Asp Leu Asp Ala Lys Lys Lys Pro Pro Ser Ala
        35                  40                  45

<210> SEQ ID NO 2
<211> LENGTH: 47
<212> TYPE: PRT
<213> ORGANISM: Sus scrofa

<400> SEQUENCE: 2

Met Leu Gln Phe Leu Leu Gly Phe Thr Leu Gly Asn Val Val Gly Met
1               5                   10                  15
```

Tyr Leu Ala Gln Asn Tyr Asp Ile Pro Asn Leu Ala Lys Lys Leu Glu
                    20                  25                  30

Asp Ile Lys Lys Asp Leu Asp Ala Lys Lys Pro Pro Ser Ser
            35                  40                  45

<210> SEQ ID NO 3
<211> LENGTH: 47
<212> TYPE: PRT
<213> ORGANISM: Bos taurus

<400> SEQUENCE: 3

Met Leu Gln Phe Leu Leu Gly Phe Thr Leu Gly Asn Val Val Gly Met
1               5                   10                  15

Tyr Leu Ala Gln Asn Tyr Asp Ile Pro Asn Leu Ala Lys Lys Leu Glu
                    20                  25                  30

Glu Ile Lys Lys Asp Leu Asp Ala Lys Lys Pro Pro Ser Cys
            35                  40                  45

<210> SEQ ID NO 4
<211> LENGTH: 47
<212> TYPE: PRT
<213> ORGANISM: Rattus norvegicus

<400> SEQUENCE: 4

Met Leu Gln Phe Leu Leu Gly Phe Thr Leu Gly Asn Val Val Gly Met
1               5                   10                  15

Tyr Leu Ala Gln Asn Tyr Asp Met Pro Asn Leu Ala Lys Lys Leu Glu
                    20                  25                  30

Glu Ile Lys Lys Asp Leu Asp Ala Lys Lys Pro Pro Ser Ser
            35                  40                  45

<210> SEQ ID NO 5
<211> LENGTH: 47
<212> TYPE: PRT
<213> ORGANISM: Mus musculus

<400> SEQUENCE: 5

Met Leu Gln Phe Leu Leu Gly Phe Thr Trp Gly Asn Val Val Gly Met
1               5                   10                  15

Tyr Leu Ala Gln Asn Tyr Glu Met Pro Asn Leu Ala Lys Lys Leu Glu
                    20                  25                  30

Glu Ile Lys Lys Asp Leu Glu Ala Lys Lys Pro Pro Ser Ser
            35                  40                  45

<210> SEQ ID NO 6
<211> LENGTH: 49
<212> TYPE: PRT
<213> ORGANISM: Gallus gallus

<400> SEQUENCE: 6

Met Leu Gln Phe Val Leu Gly Phe Thr Leu Gly Asn Val Val Gly Met
1               5                   10                  15

Tyr Leu Ala Gln Asn Tyr Asp Ile Pro Asn Ile Ala Lys Lys Leu Glu
                    20                  25                  30

Asp Phe Lys Lys Asp Val Glu Ala Lys Lys Pro Pro Ser Asp Lys
            35                  40                  45

Ser

<210> SEQ ID NO 7

```
<211> LENGTH: 46
<212> TYPE: PRT
<213> ORGANISM: Danio rerio

<400> SEQUENCE: 7

Met Leu Gln Phe Ile Leu Gly Phe Thr Leu Gly Asn Val Val Gly Met
1               5                   10                  15

Tyr Leu Ala Gln Asn Tyr Glu Val Pro Asn Ile Ser Lys Lys Ile Glu
            20                  25                  30

Ala Phe Lys Lys Asp Val Glu Ala Lys Lys Lys Pro Pro Glu
        35                  40                  45

<210> SEQ ID NO 8
<211> LENGTH: 2521
<212> TYPE: DNA
<213> ORGANISM: Mus musculus

<400> SEQUENCE: 8
```

| | | | | | |
|---|---|---|---|---|---|
| ggggcgtaaa | ccggaacctg | gcagcgggtt | ccgccctcgc | gccggggagg | agtcccggag | 60 |
| ccgagctgga | gctggagcac | ctctcacacc | ctcctcgccc | tccccaccga | catcatgctc | 120 |
| cagttcctgc | ttggatttac | tttgggcaac | gtggttggaa | tgtatctggc | tcagaactat | 180 |
| gaaatgccaa | acctggctaa | aaaacttgaa | gagattaaga | aggacctgga | agccaagaag | 240 |
| aagcccccta | gttcctgatg | cctgcctggc | actgcaatct | ggaccacca | gttccatcct | 300 |
| ggggggcctg | tctccttcac | agccacgtcc | aaagctgtgt | tcctctttgg | tctcagaccc | 360 |
| tgcgcgttgc | tgaggctcca | gcacgggcca | gaagtggagt | tagctttccg | tttccagcat | 420 |
| ctccccgttc | ccgtatcttc | cgtccacctg | cttctgagac | ctaagcctgg | aaccatggtg | 480 |
| ctaggttagc | agccgcaacc | atgacaggac | tcactcgcct | gtgctctggg | attcctaccg | 540 |
| cctactgtca | agaaatgaat | ggatttggat | agctgctggg | gactcactgt | ctagcagtga | 600 |
| taacaggagc | ttgctagaca | aactaaactg | tgttaaagtc | attaaagtca | gtatcttcaa | 660 |
| gccagtttct | ggtgaattaa | tccatttatt | atatattgtt | accaaggagc | tccatggttg | 720 |
| atgatttaac | cagtaaatca | tttgctggtc | attaaccagg | aaactatttt | atgcattcta | 780 |
| taaaaagcaa | acaaactggg | aaaacttaaa | acatgcaaag | taactgttgt | cttcgtacag | 840 |
| ttcagtctat | gcagtctatg | tttttcctta | atgatatatt | tgaactgaat | ctgccgtaaa | 900 |
| agagccattc | tttatgctgg | cacttgatag | gatgggtgga | taaatgagga | gctgttgata | 960 |
| aaataatgtt | actttttttt | ttttaaacat | taaaatgtat | cctaattata | taacttcata | 1020 |
| gtgaaccccc | taagagaagt | gtggtgcaaa | tgtgtggtaa | agtgagtctc | tctgggatct | 1080 |
| gggatctgat | gcttccccca | ccccgcccc | ccaccccac | ccccacccac | ccccgcccc | 1140 |
| cggttgaggc | atcctccccg | gaagcaggac | ggaccatcag | gcgtcagcaa | cttcattttt | 1200 |
| tttaaagaca | gtctcccagt | gttacccagg | gtggtctcaa | gctcctgggc | tcaagtaatc | 1260 |
| ctcctgcctc | agcttccggg | tgctgggacc | acaggtgtgc | accatggtgt | ccagcctagt | 1320 |
| ccgtaatgtt | tttaattaaa | aaatatttaa | aaattattcc | cacaggagat | gataggaaag | 1380 |
| tgatttcaca | tgaagactct | ttctagcctc | tgtcttattc | ccaggtacaa | ttcctcaggc | 1440 |
| aatccctggt | gtcaggttcc | tgtgtgcctt | tgagaaggag | tgtctaacca | cataagtgtt | 1500 |
| ttcgtctttt | gttacataca | tacatacata | catacataca | tacatacata | catacacaca | 1560 |
| cacagtatgt | atgtattgtg | tgtgtgtgtg | tacacatatg | cttttgtct | cttcctatca | 1620 |
| cttttgtttt | tgcacagagt | catgacgccc | acgcttttac | agtcagtgat | aacattgaat | 1680 |

```
ttctgacccct cctgcctctg cctctcaggt gcagggatcg taggtgtgca ctgccatgcc    1740
caactgtgct ttttaaagct cttttcttt tctttcattt gcttgtttt ttgagatagg      1800 gtagcccag ctggcctgga actcactctg tagaccaggc tggcttcata ctcccagaga     1860
tccgtctgcc ctttgcctcc tgagtgctgg gattgaaggt ggctccatca tgcttggctt    1920
gcttctttat tcttaatgga gagcatcccc cttccgtcag tacgttaacc ttcccccttt    1980
gtttactgtg cgcggttcca ctgaatgggt gtttcataat tgaatgtgct actgctgagt    2040
gcttaggctg gtcttctgct ggtgtggtgc tagcactgaa cctgatgccc atatctgccc    2100
agagtagagc tataggataa cgactcacag tctagtttgc taagacacgg tgtgtctcgt    2160
ttcagagggc ttattgggca acttccctga caatgaatgc cttttttgaa gaccacaggt    2220
tgcaaagata agttagggac atctgtctgt tttcgggaag tgaggacagt gaccccatat    2280
gggaatcaga acatggcatt gctccttaga gatacattcc atccctgtca aggtcatctc    2340
tgtatacgag acagaggttg gcttctccct agcagtgggg agtggggagt ggtgtgttct    2400
tctgagactc tgtaacatct acctcatgag ggtttcctgg gaaacagtga gatgatgttc    2460
tgtgctctgt tagactgtgc tttgcaaact gtccaataaa tagtagctac ccattggaaa    2520
a                                                                    2521

<210> SEQ ID NO 9
<211> LENGTH: 1232
<212> TYPE: DNA
<213> ORGANISM: Mus musculus

<400> SEQUENCE: 9
acctctcaca ccctcctcgc cctccccacc gacatcatgc tccagttcct ggtgagtggg      60
gcctcggagg atcgggcctc gcggtcgcct cgttcccccg gggtcccggg tcggcggtgc     120
acggctctgc agttggggct cgtcgccctc gggtttgctc gcgcagtttt cctctggcct     180
cctcctaagt ccttgggtct ttgcctgggt ttgtttatat gtagtccttc aagttccgaa     240
aactttgggg tgtcagtgat atgactgcgt tttcaaaaaa ccacttactg tgagctcttg     300
gcgaaatctt cgcgcttgga tttactttgg caacgtggt tggaatgtat ctggctcaga     360
actatgaaat gccaaacctg gctaaaaaac ttgaagagat taagaaggac ctggaagcca    420
agaagaagcc cctagttcc tgatgcctgc ctggcactgc aatctggacc caccagttcc    480
atcctggggg gcctgtctcc ttcacagcca cgtccaaagc tgtgttcctc tttggtctca    540 gacccctgcgc gttgctgagg ctccagcacg ggccagaagt ggagttagct ttccgtttcc    600
agcatctccc cgttcccgta tcttccgtcc acctgcttct gagacctaag cctggaacca    660
tggtgctagg ttagcagccg caaccatgac aggactcact cgcctgtgct ctgggattcc    720
taccgcctac tgtcaagaaa tgaatggatt tggatagctg ctggggactc actgtctagc    780
agtgataaca ggagcttgct agacaaacta aactgtgtta aagtcattaa agtcagtatc    840
ttcaagccag tttctggtga attaatccat ttattatata ttgttaccaa ggagctccat    900
ggttgatgat ttaaccagta aatcatttgc tggtcattaa ccaggaaact attttatgca    960
ttctataaaa agcaaacaaa ctgggaaaac ttaaaacatg caaagtaact gttgtcttcg   1020
tacagttcag tctatgcagt ctatgttttt ccttaatgat atatttgaac tgaatctgcc   1080
gtaaaagagc cattctttat gctggcactt gataggatgg gtggataaat gaggagctgt   1140
tgataaaata atgttacttt tttttttta aacattaaaa tgtatcctaa ttatataact   1200
tcatagtgaa cccccctaaga gaagtgtggt gc                                1232
```

<210> SEQ ID NO 10
<211> LENGTH: 690
<212> TYPE: DNA
<213> ORGANISM: Mus musculus

<400> SEQUENCE: 10

```
gagctggagc tggagcacct ctcacaccct cctcgccctc ccaccgaca tcatgctcca        60
gttcctgtcc ttcaagttcc gaaaactttg gggtgtcagt gatatgactg cgttttcaaa      120
aaaccactta ctgtgagctc ttggcgaaat cttcgcgctt ggatttactt tgggcaacgt      180
ggttggaatg tatctggctc agaactatga aatgccaaac ctggctaaaa aacttgaaga      240
gattaagaag gacctggaag ccaagaagaa gcccctagt tcctgatgcc tgcctggcac        300
tgcaatctgg acccaccagt tccatcctgg ggggcctgtc tccttcacag ccacgtccaa      360
agctgtgttc ctctttggtc tcagaccctg cgcgttgctg aggctccagc acgggccaga      420
agtggagtta gctttccgtt tccagcatct ccccgttccc gtatcttccg tccacctgct      480
tctgagacct aagcctggaa ccatggtgct aggttagcag ccgcaaccat gacaggactc      540
actcgcctgt gctctgggat tcctaccgcc tactgtcaag aaatgaatgg atttggatag      600
ctgctgggga ctcactgtct agcagtgata acaggagctt gctagacaaa ctaaactgtg      660
ttaaagtcat taaagtcagt atcttcaagc                                        690
```

<210> SEQ ID NO 11
<211> LENGTH: 8922
<212> TYPE: DNA
<213> ORGANISM: Mus musculus

<400> SEQUENCE: 11

```
gagctggagc tggagcacct ctcacaccct cctcgccctc ccaccgaca tcatgctcca        60
gttcctggtg agtggggcct cggaggatcg ggcctcgcgg tcgcctcgtt cccccgggt       120
cccgggtcgg cggtgcacgg ctctgcagtt ggggctcgtc gccctcgggt ttgctcgcgc      180
agttttcctc tggcctcctc ctaagtcctt gggtctttgc ctgggtttgt ttatatgtag      240
tccttcaagt tccgaaaact ttggggtgtc agtgatatga ctgcgttttc aaaaaaccac      300
ttactgtgag ctcttggcga atcttcgcg gtaagttggg tcggaggagt catcaagatg       360
acttggctcc tgtcctctcc acgcgacttc ccgtagaccc ccatctatta tatacggctt      420
atttgaggcc tcagagtgcc tttcacacgc cgtgcattag tcagccacat cacgaggtcg      480
cagcgagaga tccacagtgc cctccctctt cagacccttta cagattgccc gctttgagga    540
gtgagtcaga ctgccctgcg agtaactctt gtaaaaacct gcccctcccc acacccttc      600
aagtctcctt tttgagttaa cacgttttc tggcaaaaat caagtatttc taaaattgcc       660
tgttgaggat tctaggaaac ttgccagtca aattttcaga tgaaagtttt caaacacttt      720
cagatgaaag cgtttcatct tcgaattcta ataaagcaga tatcttcttt ctttcccacg      780
gtcagtggct acctggtgct ccgagaatga gtattgttta cataaaactg ccctacaaag      840
actcagttgc ctctggggtt tctctagtgt cctaactagg ccttagttta ggaggtagga      900
gtaattagca gtaatttact tgttaggaat cacttttaaa agcagcatca gccagctagt      960
gtaaggtgat aggattggcc cttccactgc atttgctgtt cattgataag cagggagaac     1020
attaaatcga ttacacttaa ccttttaagt gctttgctga atgaggctac ctggtgcggg    1080
actagcgctc tgtacttaaa catgggtttt gattggaaaa ttcaaaattt tcaacattta     1140
```

-continued

```
tggagagatg ctgaagccga ccattagatg cttagctagg atgtaactga tgttccttct    1200
cttgccctgg gtctgtctcc tcttcattgc ttttgttggg aaaagtggaa tcagatgtac    1260
agagatggaa tcaactttcc tcttgtggaa cttggtcaaa cactgctagt ttctgcaaat    1320 cttgctttt  acattagccg tttcaactgt tttctaaatg gttaagagtt tagaccctat    1380
ctttaatctc aaggtgtgtg tgtatgtgtg tgtgttgggg acgtggggtt gggtgggtgt    1440
tggccaggtt atttaaattt tctatgcttc agtttgcacc tcatgaggtt tcaaaaggag    1500
ccaagatgtt gaacacgtaa acactaaatc gtggttgaga tatactgccc tgtctcttct    1560
gtaaggtatc agaaatggga actggcctcc cactgatagg agaggcttgg gtgtggtgga    1620
aagattccag gctcttccct ttgatggtgc aaggcagctg aatactttgt aacctctgag    1680
atgttgccta agttgaaaac ttgcatttga ttgtgtggct tgtctaccca ttaccccctat   1740 ttccacaccg cactccacag cttgctccta gcttggctga agttctttga aggaacacct    1800
agatgggaat tggactgtga gcactgctgt gagtgtcagg gcacctgaac actgctacag    1860
tttctgttcc tcttccccct ggggcccagt agcatcacct cctcataact caccctcatt    1920
cagctgctgg ggcctgtgca ccgtgctgtg tgggttctgt cctgggatag ctcagaattg    1980
cggagtgagg ggaccatatc tgggtgtagc agctgggagg ctctctcccct gtctctaatc    2040 ttgtctcccg ctgcttgctt ctgctcttag ttcctgtgaa gtgcttaagt ccggagctgg    2100
ctgtgcttcc taaactcacc cttagggaac gggctcctcc ccaagccagc acctttcaca    2160
tcagcttcca ggacaacctt gaatcccctt ctctgtgctt ccagatccca gtatcaact    2220 gtcagtggct ttcctttgcc tttctctcag cctctactca tctggattga gtttgccttc    2280
ctgctttccc agtcctttcc ccacacttaa cgctcacatt tgaaatgttg acatagtcat    2340
tgatttcttt ctcgtattca tgcattcacc ggtttatcta gtcttttctt agaatcatgt    2400
aataccgtag gtgcatcttc tttgttacat tgcatccgtt tatctgttga tgactgtgcg    2460
tgcctctcct gtgagggcct gcacgtgcaa gaagtctgag gacagcctcc agcagccggt    2520
tctccttccc tcatgtgggt ctaggggggtt gagctcaggt tgccaggctc gggtgcaggg    2580
tgttaccctg ctgagccatt tttccacgcc agacctgctg tgtagtcacg agtaagatct    2640
ttacttgctc cgtgcctcag tttcccccag cataagcctg ggcagtaata gtggttattc    2700
cacgtgtgca tgcttgtgag gatcaggctg tgaactagca gggttctcca gtctggctgg    2760
catactgcca cttctctcca ctactaaagg atttggttgg ggatataaag ggacttagtc    2820
aatacgcagt gagtgacttc gtttgcactc agctctgcat attgctgggc ccatccgcat    2880
atttaactaa ccatggatta gataaatatg aatgaatatg aaaaatataa atattagcag    2940
atagttgctc atcaatggta tgtgtacagt ttttccttgc cgttcctgag cagtgcagtg    3000
ggatagactg ccgcaggcct tccatacagt aggtcttatg agtgatcaag agggttagag    3060
tgtatgggag gacatggggg gctcccgtgc agttgtagga cctgcttgaa tagctacaga    3120
tgttggtgtg gggggtgtcc tgggatggag cccctcatta atttttaggtc ttccttcttc    3180 acctcattac taccgttgat tataagatag tggttacaag gtagctccag cttcttttag    3240
agcaggcaaa cccgtacacc ttttcccagag agatttcatg tacttctgtt gaatattggc    3300
acattaagga ggttttttt  tctccttctt ttcttctcta agcagtatta ctgaatataa    3360
agcatgcttt cctaggaagc agtgaagggc tttagcccta gcaaggtttt gctttaatac    3420
acagaatgta gggttgtttt tttttaaact actaaacatt tggtgatagt cttcacactg    3480
agtttaaaaa ctaagacaga gaaatggtag tgtgtgtaca tgcctccttg gaaggccttc    3540
```

```
tgatttcttc ttttgaatct gaatttaaga atgctgttgc catggctgaa gagatgcctc    3600
ggctgttgag agcgctggtc gctcttccaa aggacctggg tttgatttgc tgtacattga    3660
tagaggctca caacatctgt aactcgagtc ctaggggttc tgatgttctc tttggcctct    3720
gtgcatactg cacgcatgtg gtgggcatta tattatacat gtgggcagga cacccataca    3780
ggtaaacata aatagcattt taaaatattt tatcaactta gctttttatt agttctagtt    3840
agttaatgta cagttttttg agttgtagat gcttttacca taaaccaaat gtcattttta    3900
ggtttccttt tcagtgctgg catgagccta tatttgctta acaattttta aaaagatttt    3960
tattatttta agtgtgcttg tgctcagggt agaggtgtga gttctctggt gagttgcggg    4020
taggcatgag ctgcctggta tgggtgctag gactgagctc gcatcctctg aaagagtagc    4080
atgagctctg agtcgctgag ccatctctcc aacccttttt aaaaatagat tcttaaatcc    4140
ttatcagtaa cttgggcctg ggtgtgttat ttttgaaaat acagtttgat gagtcacatt    4200
cggacttgtc agccgctttg aggttttgcc aggagctgtg ccagataaac attgcggttt    4260
tatttgctgg tctccagaca caactttctg aaagggaagg ccctgagtgg atggcagatg    4320
catctgtttt ggagtaggcg ctgtgccttt tagcagagct ttttagtgtt aatggataaa    4380
gcattgttga ccaatctgtt tgtgtgttaa agaaatagg tacacttaca ataatgtaga    4440
ctcctcatgc gcagactctt ccatttattg gactggttct attttgcacc tctgaatttt    4500
ccattctttc taacaaagtc caggttggaa gccatgaagt tgtctttggt ttcttctact    4560
tcactccagg tagttgagat gactttacca aatttggtga tattgtttgt ttgcttgttt    4620
gtttgcttgt ttgttttgtt ttgtttggca ttgagacaaa ggttcaccca tttattgtat    4680
gtaatccagt ggcttcagtg tgctcagaga tcgtgtacct tctcatttta cataaaaaag    4740
aaactgtata atataggag tcatttctca ttcccctctc caaactggac aatcaacagt    4800
tggttttcta tcaatgtgga attgctgttt tgtatttttt ttttaataga accatacagt    4860
atgtggtctt ttctgactgc ccttgactgc actgtcaagg ctcctctact gacagcatgg    4920
agcagtgagc gcttcatttc tcgatatgat gagtatgtgt taatcagctc tccagttgtt    4980
tccgctcttg gttgttagga atgggctaag ccaggaatat tgaggaggca ttttgtggg    5040 ggttcatgtc caccttttgg tgcatgccca cactggagtt gtcacatcct ataactgtgc    5100
acacagcact ctggaaagtg gctagatggt ttttcagagc ggccatgtgt tatacaccag    5160
tggaagatga agacctccgc cccatgtctt gccagcattt gttgtttgtt ttgtttggtt    5220
tggttttgct gcttttgagt aaagccatct aagcggatgt gccgtggttc ctcgtggttt    5280
tgattagcgt ttcctcggtg actgatgtca acatctcgt gggcttgttg actccgtgtc    5340
tttggaggat ccactcacag cttctgccac ttttaaatt gaattatgta tctccgtcat    5400
ttaattgtga aagaccagat tatgatttgc aaataattct attttgtggt ttgtcctttc    5460
tctttgatgc tgttatttga agggcaaaca ttttatatt tcgtgtgtgt atgtacacgt    5520
gactatgcag gactgtttgg ctgtgcatac agatgtccag gtttagattt gcttttcttg    5580
tctgctccta cctgttgacc atctcctgaa gcaagcacgc tttcctgact tctgggttct    5640
ccatcatttt cctgagtgag tggcacttct cacatgtgct ctgcatcata tttaaaatgt    5700
cgcgttgtag atttggtagt attctggaac gggtgccgcg tatagaggcc atgggttttg    5760
tttgtcttct aaaataactg tccccttttc tgcccagtg cttggtgaca ttgacaaaat    5820
agttagttag gcagtgttta ttttgagaca cacattgtaa gaattaggaa ttctgtgtct    5880
```

```
gagccggaac gtttcagtgt tgggctgatt cagaggtgag gaagcgcagc ggagctggag      5940
cgggttgagt ggcccacgaa ggcacggtct ctcggacgaa ggcacggtct cgtctctctt      6000
gcggggctac tgcttctcac ggttcctcgt gccggctagg attcacagca tcaaggagtt      6060
cttcccctct ccttttaaat tttgtctcaa attaaattat cttctggtt ttcagaaagt       6120 tgtggtttga atctactaga gtgaaaaaaa tgtaattctg attcttattg ctaccttagt      6180
aatgactttt aaaacatca gaaaatggtt agcagcttga aactaggtag cttcttttat       6240
gtttcttgct aacaaccaac caatttaaaa ctgcctttgg gtttaaaggt taagtataag      6300
acagacccag ttgtagttct ccttttttgt gttttctccc ttcagggttt atttttacta     6360
tttatggtgg tggtggtggt agtggtagtt gtagtgtgca ctatgttcac tggcatgtgg     6420
atgccggcag agggcagaat aaggtgttgg ttcctgaagc tggagtcagt tgtgagctga     6480
ctaacatggg cgatgagaac tgaactctgg tactctgcag tggtcctaac tgctgagcca     6540
tctctccagt accccatct gtatccttgc ctcacctgca tctcatgtgt gagtgatggg      6600
acacttaatg ctgttctttg atttctgtct taacttctct gttgagactg agttagtggc     6660
aataccgttt aaacaaaaca atgggaaaaa agggtagatg ccaatttgaa tttattaagt     6720
tagaaattag cccacagtta caagctctga aataaaagt cactgaggga aatcagaatt      6780
atcattaaat tgcacgtctg tggaactctg gcccatttgt gtatatggag tatttgtgta    6840 tatgagtat tctacatttt caggagaata ctcactcagt ggggtaaatg tttacagttc     6900
tctaaaagtt gtccatgtcc cttttgtcat tgagtgggag ccacagacct taagtgtcct    6960
gccctttagt ccccacccctt ggcgtggtgc taggctccgt gatgtgtcag agtttcctgt   7020
tcttctctgc ccttgaggat ttgagtcccc gagtaactgg agttgttgtc tgctgctgct    7080
ttcctgaata accctgggca aaccgctcta gctcttttga aataaggaga gactaaactc    7140
tgagagcccc tttattttc taagcttttt tgattcaaac gggttttgt tgttgttgtt      7200 ttgagaagaa gtcttgtttt gtggggatga gacttttgct gggtagctgg gactctctgt    7260
gtagaccagg atggcctctc caggccaaga atgcccctgc ctctgaatgc tgatggcaaa    7320
tgtgagccac catgcccagc tcccgtgggt atttgcaagt gaataccttt tttatcagct    7380
gtgtacagga gtaacagtac ctacaacaaa cagtaacgag taatagtaac aaaatcagaa    7440
cactggcttc cagaccttc aaacttgctc aaagccaccg ttattctgtc ctaatgttgg     7500
tgcatggtat atatgtatgt gattgtttca tagaagaaag atgtgacttc tctgttggat    7560
gcagtcctac actgaggacc tgggcagtca cctgccgtgc acttcttggg aagatgcagc    7620
ccgtgtgtct gacatagttg caggctcctg gtgggttttg cctgcagtgt aactctcctg    7680
ttctgttctt tcagcttgga tttactttgg gcaacgtggt tggaatgtat ctggctcaga    7740
actatgaagt aagtgactac attcatgtct ttcttggctt actgtaaccg tttcatagtt    7800
acatagttac ctctctcaag gtgaagtttg cgtgctaaca cagtgaggtc tgtaaatgta    7860
actccttaat tttatagaaa gcttttctgt tgtttgagaa agtaactgaa ctcacaaagg    7920
cacggtgtcc gcacatcatc ccaggagaac tggatgtgaa tttagcgtgg cttgtaggag    7980
gaagacggtt tgggaaagtg aggagtcaca tccacctcac tgttggtgta tgagggaggg   8040
aggaggggtg gaaaaatgct gtcacagccc aacgagaagc ctcgaatgtg ttgcagagag   8100
acaaaggatt acattttctt ctgtacccag ggacaggaac tttgttgctt tcttattgcc    8160
tatagataca cttcttttat ctggcacttg agctgaaggt ccaagtgtgt atctaaaggg   8220
agtgctgggc ctggctttca gagaggaaat gtaaatctaa cactgatagc taatatatat   8280
```

```
agatacaagc caaggaaaca ccactgagta ggtctccaga ggaagccaaa gccttggcaa    8340
agccctttgt cctttaaaga agagctgtga aagatactgg caagtctttc tagtcttcct    8400
atctatagct aaattataat gtttctttt tcctcttta aagatgccaa acctggctaa      8460
aaaacttgaa gagattaaga aggacctgga agccaagaag aagcccccta gttcctgatg    8520
cctgcctggc actgcaatct ggacccacca gttccatcct gggggcctg tctccttcac     8580 agccacgtcc aaagctgtgt tcctctttgg tctcagaccc tgcgcgttgc tgaggctcca    8640
gcacgggcca gaagtggagt tagctttccg tttccagcat ctccccgttc ccgtatcttc    8700
cgtccacctg cttctgagac ctaagcctgg aaccatggtg ctaggttagc agccgcaacc    8760
atgacaggac tcactcgcct gtgctctggg attcctaccg cctactgtca agaaatgaat    8820
ggatttggat agctgctggg gactcactgt ctagcagtga taacaggagc ttgctagaca    8880
aactaaactg tgttaaagtc attaaagtca gtatcttcaa gc                       8922

<210> SEQ ID NO 12
<211> LENGTH: 34186
<212> TYPE: DNA
<213> ORGANISM: Homo sapiens

<400> SEQUENCE: 12
aaacatccta aattccttcc attgattgaa cagaccctct ttttggccaa agggactcca      60
gaaagacctt aaaactgagt tcccagacat gatggtacgg gaggtcagac atgcctcgtt     120
atatcccctc tcctttgcag tttaaatgca acaactgatc agcattaatg ttaaaacaca     180 gaccagggg agtaagctct ttcctttctg tctggcagca gccatcaggt aagccaaaat      240
ggatgcatac aagtacatcc aggagcaatg gaggaagaag cagtctgatg tcatgcgctt     300
tcttctgagg gtctgctgct ggcagtactg ccagctatct gctgtccacg gggctccctg     360
ccccacctgg cctgataaag cacgccagct gggctacaag gccaagcaag gttacattat     420
atataggatt catgttcacc atggtggtca aaaatgccca attcctaagg gtgcaactta     480
tggcaagcct gtccatcatg gtgttaacca gctgaagttt gctcgaagcc ttcagtccat     540
tgcagaggag cgagttggac acaactgtgg ggctctaaga gtcctgaatt cttactgggt     600
tggtgaagat tccacataca gatttttga ggttatcctc attgatccat tctatgaagt      660
tatcagaaga aatcctgaca cccagtcgat caccaaacca gtccacaagc agagggagat    720
gtgtgggctg acatctgcag gccaaaggag ctgtggcctt ggaaagtgcc ataagttcca    780
ccacactatt gatggttctt gctgggcagc ttggagaagg cgtgatactc tccagctcca    840
ccgttaccac taatataagt aaagtttggg ccaggcgtgg tggctcacgc ctgtaatccc    900
agcactttgg gaggccgagg cgggcggatc acaaggtcag gagatcgaga ccatcctggc    960
taacacgttg aaacctcgtc tctactaaaa atacagaaaa ttagccgggc gtggtggcgg   1020
gcgcctgtag tccagctac tcgggaggct gaggcaggag aatggcgtga acccgggagg     1080
cggagcttgc agtgagccga gactgcgcca ctgcactcca gcctgggtga cagagcgaga    1140
ctccgtctca aaaaaaaaaa aaagtttgta aaattcgtac ctaataattt aggacagtca    1200
tgtctgctta caggtgttat ttgtctgtta aaactagtct gcagattgtt tcatgaatgc    1260
tttgtcaaat tatgaaaatt aaagtgcaat aattttgaa gacaataagg gatggtgtat     1320
cttgtttcta ataagatgaa cttttttgt ctttgcttta tcttattagg gagttatata     1380
tcttattagg gagttagtgt ttaaaacata ctgtgtggta taataggctt aaaataaatt    1440
```

```
ctttaaaaga gaaagagaga aaaaaacaca cacatacaca gaccggaaga ctgacagaac   1500
agactctttg tggcgatgat acaaattgtc aacaggacct atggccatcc caggcaagaa   1560
acccagctag gccagtgaaa ctgagagcca acctgatgag gcctgccaaa tgcaacttct   1620
ctcacttgtt tttagtcacc tgcttttagt ggattaaaaa acccacatag ctaaagtcac   1680
agagctaaac aatatatatc taagctccca ctatcttcct tatggataac atctctgaca   1740
tctgggttgc ttgataaagg tttcttgttt ttcaggaagt tggggtcagt tcttgtacag   1800
tttaaaccac caacctctca actgggcctg catgaaagcc cgatgggtgt ccttctgaca   1860
ttagagggcc aaaacctcca cactcagatc atgctaagga tgtcattttg tgaccatgta   1920
tcctataaag agccatgaag cttgactacc tcgcgcagat aacccattgc caaacttttc   1980
cttaccttca accgcctttc cccacacctc agaccaccct gctcctctat cccataaata   2040
tccctaaaac ccatctttgg ggaggcagat ttgagatctg ttctcccgtc tcctcggctg   2100
gctgcctggt gaataaacct tttctctgct acaaaactca tcatctcagt gactggcgtg   2160
cggcacacgg cagcatgggc cccatacggt acccagcctc taccttgatt acacaacacc   2220
tgattacaca acgctgatta cacagcacac ctgcggagct tgagagctaa caagcctcct   2280
ttcctccccg caaagtccag ctgggcccaa gtagaggatg ctgcaaaagc ccccacgatt   2340
cagctgcgaa cctagggatg ggacccgctg ctcatgccgt ccttctaggt tagagagccc   2400
taaactgggc tgtgtatcag aatagtccgc gtgctgagaa taatatagat tcctgggcct   2460
cggcccaggt ttacagaggc gggatgctca aggatgccca gccaggctcg ggacttgctc   2520
ttcgcaagtc ctgtcgcgcg ctcgctgccc gccggttca ggcggtgagg ccaacgcgct   2580
ccgccagggg gaacctgggc gctgcgacac tgcaagtcgt ttccgggcgc gggctgagtg   2640
ggaggagcgg ggcggggcgt ggcgtgaccc ggaagtcgac gaggggttcc gcccccccg   2700
cgcatgggga ggtaggctcg gaccggcccg cggagctgct gcagtccttc gcgccctcct   2760
cgccctcccc accgacatca tgctccagtt cctggtgagt ggagctgccg aagagcgggg   2820
cccgctgcct ggggcgtgcc tcggaccccca tttccccctt gaggattgcc gaccccgccg   2880
acccggcctg ggcgtgggtc cagcggtccc ttcgtccccc gcgcctggtc gtcgcctcgc   2940
agggcggccg ttttcttcct gcctccccag aaaatccctt tgccaatatt tttctgcagc   3000
catccaagtc cctaaaactt tgaggtgtca gagagtgtgc gtttccagag cttcttattg   3060
tgtgccgcgc ccgcgctca ttgtgcaatc tttgtattaa agcttgtgtg gtccttgatg   3120
acttttcgta gtccgccccc ctttctttct gcgctcctgt tccattacat ggtcgccggc   3180
cggtccctgc tgtggagccc tgctagttgg cttttctgag gaggtaggaa ggccaggaat   3240
aaaccgtaaa ttagccacct cacgaagtcc gagaggctaa gtcctcatca gaccttcag   3300
agttggagga atgagtcaga cactggtata caagtaattt ttcccaaaat gtgtaagcat   3360
gagtaagcag actatttctc ttggctcctt atttgagtta aaaacgagtt ttctggcaaa   3420
actcggtata tttcaaaaat tgcttggtga aggttccagg agttgctcat caaatttca   3480
agtgaaagtt tttctgccaa gctattgtgc attcaaaact tgatgctttc aacctctatt   3540
ttttttatt tttatttttt tttgagacgg agtctgctg tgtcgtcagg ctggagtgca   3600
gtggcgcaat ctgggctcac tggaacctcc gcctcccggg ttcaaccgat tctccctcct   3660
cggcctccgg agtagctggg attacaggcg cgcaccagga tgctcagcta atttttgtat   3720
ttttagtaga cgggttttc accaagttgg ccaggctggt ctcgaactcc tgacctcaag   3780
tgatcaaccc acctcagcct acgaaagtgc tgggattaca ggcgtgagcc actgctcccg   3840
```

```
gctcaaatgc tgtatctttt tttgttgttt gttttaacgg agtcccgctc tgtcgccagg    3900
ctggagtgca gtagtgcgat ctcggctcac tgcagcctcc gcttcctggg tttaagcgat    3960
tctcctgcct cagcctcccg agtagctggt gcgcgccagc aggcccagtt aattttgta     4020
tttttagtag agacggggtt tcaccccgtt ggccgggatg gtctcgatct cctgacctcg    4080
ggatctgcct gcctcagcct cccaaagtgc tgggattaca ggcgtgagcc tccgcgcccg    4140
gccccaaatg ctgtatcttt atcaaagaga ttaaaacaca aaatgcaccc cttttgtcct    4200
tttgaaagat ggtaatggat tgttaaatcc aattagtcaa aagagtgtcc ttaatctgcc    4260
cagctaagac agggctgctc ctttgcctct aggagtttct gtagtgtcct aactagatgt    4320
tagtttagga gttcagaata atgacagtca ttttcttgta gtaaacacta gattaaaagc    4380
ggtatcactt agctccagag tatagaatga tgtaattgag ctgcttacta tatctgttgc    4440
tcattgataa actgagagga catgattcaa ttacagttaa cttttctaagt ggttttgcag    4500
aatgagtcta tttggttttg caataaactt ttactgtgtg ttaattttt tttttttttt     4560
tttttttga dacaaggttt ctctttgtca cctaggctag agtccagtgg cacaatcatg    4620
gctcagtgca gtcttaatt cctggcctca agcagccttc ccacctcagc ctctttagta     4680
gtagctagga ctacaggccc gcactaccac ccgtgactaa ttttaaaatt ttttttttgt    4740
agagacaggt cttgcctagg cctcccacag tgttgggatt acaggcatga gccaccactg    4800
tgcctggtca gattctgatt tgagaattca gaattctcag tatttaagga gagatgctaa    4860
agctgtcaat tatattccta gctcagaagt aactgaacac tgatgttctc tcaccctctg    4920
gtcttccacc tcattgcttt tttttttaaa taagtggata gcattacttt tcacattgat    4980
tccacctctg tcaaatgagc cactgactct aaagttgagc aagtatttct ctttgtgtgc    5040
agtcatttca tctattaaaa aatgaccatc atgttctagt gtttaagaga ttaaacttca    5100
gagtcagact tctcagtttg aactctgcct cccatcattt tcaagctgtg gtagcgtggg    5160
tgggctattg aaattttctg tgctcccatt tccacatctg aaaatgcaaa cccacctcac    5220
agttttgttg tgaggattaa aaatgagtta acacattaaa gaacttaaaa acaggagcac    5280
tcaacaagga ttcagatagt gttcagtttt tcttttgcag ggttcatttg aaccctgatt    5340
gagtttcttc tcaagtgggg attagcttct ctcagaaggg taggtgatag gaaaggttta    5400
gaagtgatga aacagtcaca agttaagcag tgcgttgtca ttacacattt tggaaccgtc    5460
taagatgttt ctcctacagt tgtgatttgt ggacagtttg aaaaccactg cacttgcttg    5520
tgttggtgat aacgtccttc cattattcat attcctcctc agattaaaat attctccctt    5580
tgtccctatc ttgaagagac cttgttcctg tgattttccc cttttctttt actgcagttt    5640
ttcccctttg ttattactat ttttaatagt ggagataggg tctcactata ttgcccaggc    5700
tggtcttgaa ctcccaggct gaagcaatcc tcccacctca gtctctcaaa gtgttggatt    5760
atgggcttga gccactgctc ctagactttt tttttttttt ttaaatgcag tgcttcagaa    5820
atttgtgtgt cgtctttgcg caggggccat tctgatctct gtatcattcc agttttagtg    5880
tatgtgctgc caaagtgagc accccccttt cttttactgc agtaaaagac acctcttgc     5940
agatagttac caacactacc tgagggaagc tactgcttcc ttaatcgtaa ggtttagcta    6000
gagttatttt aaggatgctt ttggcgggaa gctaacatga tggcactgct gggggctttg    6060
tgcacactgc ctatgatgtt gttattgtgt tattgtaatc tgttgctttt ttttttttg     6120
agacagaatc tcactctgtc acccaggctg gagtgcactg gtgccatctt ggctcactgc    6180
```

-continued

| | |
|---|---|
| accctccgcc tcctgggttc aagcgattct cctgcctcag cctccgggtt caagcgattc | 6240 |
| tcctgcctta gcctccgaag tagctgggat tacaggcata tgccaccaca cctggctaat | 6300 |
| tttatatttt ttagtagaga tggggtttca ccacgttggc cagcctggtc ttgaactcct | 6360 |
| gacctcaagt gatttaccca cctcggtctc ccaaagtgct gggattacag gcgtgagctc | 6420 |
| ctgcacccgg ccggttttcc ctttatcctt tttgccttcc taaatactct tcaaggcccc | 6480 |
| actttgatct ttttccatga ggccctcctg atgacttatg cttctgaaac ctttacacta | 6540 |
| ttatgtcttt gttttgtttt gtttttgaga cagcgtctca ctctgtcacc caggctggaa | 6600 |
| tgctgtggtg caatctcggc tcactgcaac ctctgcctcc ttggttcgag cgattctcgt | 6660 |
| gccttacctt cccaagtagc tgggattaca gacgtgtgcc accatcccg gctaatttt | 6720 |
| gtatttttag tagaaacagc catgttggcc aggctggtct caaactcctg gcctcatgtg | 6780 |
| atctgcccgc ctctgcctcc caaagtgctg ggattacagg tgtgagccac tgtgcctggc | 6840 |
| cttacactat tacactatta tgatccattt cctcatttat ttaggtctca tgtcttttca | 6900 |
| gtaacttctg ataattatc ttgcaccttg tttgttatgt ttattctat tttgttaatt | 6960 |
| atttcaccag ttgatggaca ttcaagatgt ttccactttt ggctatgatg agtaatcctg | 7020 |
| ctaggaatat ttgtatacag ctttttgtgt ggatatgtat ttcagttctg ttgagtatat | 7080 |
| accctaaagt gggattgctg cattatgtgg tatctttatg ctcaactttt tgaggaactt | 7140 |
| ttggactgtt ttccagagta gctgcaccgt tttacattct cactagtaat gtatgacggc | 7200 |
| ttcaatttct ccacatcctc gccaacattt cgtgtagctc ttattgtttt tgttaaagta | 7260 |
| attctagtgg gtgtgatgta gttcctcatt atggttttgc tttgcatttc ctcagtgact | 7320 |
| aatgttgagc atcttttcat atgcttgttg actgtttgta gctttggaga aatcctttca | 7380 |
| catcatttgt ccattttat ttttgtttta ttttatttat ttattttga gacggagtct | 7440 |
| cgctttgtcg cccaggctgg agtgcagtgg tgcagtctcg gctcactgca acctctgctt | 7500 |
| cctgggttca gtgatttct cctgcctcag cctcccgagt agctgggact acaggcgtcc | 7560 |
| accaccatgc ctggctaatt tttgtatttt tagtagaggc ggggtttcac caagttggcc | 7620 |
| aggctggtaa ttgaactcct gacctcaggt gatcccccaa ccttggcctc ccaaactgtg | 7680 |
| ggattacagg tgtgaaccac tgtgcctggc caatttgccc attttaaat tgagtttttt | 7740 |
| tgtgtcactc agttgtaaga attatttata tattctggat acacatccct tatcagatat | 7800 |
| atatttgaaa atattttatc tcattctgtg tgttgtcttt tgactttctt gatggtgttc | 7860 |
| tctgaaacac agatatttt aattttgatg aggtccaatt ttttttttg gttacttgta | 7920 |
| cttttggtgt catatctaag aaaactatt gcccagcccc actcatgtga aacacagata | 7980 |
| ttttaatttt tgatgaagtc caatttttt ttttggttac ttgtactttt ggtgtcatat | 8040 |
| ctaagaaaac tatttgccca gccccactca tgaaggttta cgcctatgat ttctttgaag | 8100 |
| agttttatag ttttagctct tacatttagg tctttaatcc atttttgagtt aattttttgta | 8160 |
| tatagtgtga gataggagtc cacctttatt ctttgcatgt ggatatccca ttgtcccagc | 8220 |
| accatttctt gaaaagatta ttcccagcac catttcttgg aaagactatt ctttctatat | 8280 |
| tgagttcctt ggcactcttg ttgaaaatca cttgaccata agcctttatg gtgtattcct | 8340 |
| gggctctcca ctttattcca ttgatcttta ttgatcaata gaaacaattc agtcttcttt | 8400 |
| ccttgccacc acagtaatcg gcttttctct aatgggtact tggttttctt aaaaaaaaaa | 8460 |
| ttacctttt aaattcctac atcttttcat catctaatag gtccttgttt cctcagcctt | 8520 |
| ttctgagtat aggtaccggg agagtgcttc tcaggcagtg ctttcatcat gttgctgagg | 8580 |

```
gcagagtagt cagtgtctcc ctaccatgat tgcatgtgaa ggaaactccc ctgcctctga   8640
tgcccaggct ggagtgcagt ggcatgatct cagctcactg taacctctac ttcctgggct   8700
caagtgatcc tcccacctca gcctccagag tagctgggac tacagatgta tgccaccaca   8760
tccggctagt tttgcatttt gttggtagag atgtagtttc accatgatgc ccaggctggt   8820
ctcaaactct tgggctcagg ccatcctctc accttgtctt cccaaagtac tgggattaca   8880
agcgtagcca ttgtacctgg ctgccctacc tgcttgttga agcccaacat ctagacctt    8940 ccagctttcc atacttaatt ctctccattc tttaactcaa attctctttt ccagtcaggc   9000
ctgtttcttt tatgccagtc atcacatgtc cattcccatc tcgtgccttg attttccaca   9060
ttcagttttc ttcgcatttc ctttaccagt tgtattagtc cattttcaca ctgctgataa   9120
agacataccc gagactgggt aatttacatg gaaaaaggg tttaatggac ttacagttcc    9180
acatggctgg ggaggcctca atcatggcag aaagcaagga ggagcaagta acgtcttaca   9240
tggatggcag cagacaaaga gagagcttgt gcagggaac tcctctttat aaaaccatca    9300
gatctcatga gacatattca ctatcacgag aacagcatgg gaaagacctg ccctcatgat   9360
tcagttacct cccacttggt ccctcccaca acgtgggaat tcaagatgag atttgggtgg   9420
gaacacagcc aaaccgtatc accagtttaa atgtgaacac ttagcatatt tagagccttt   9480
aatatcaacc tgaggtatat attttttcaag tatgatttct taaaagaatc acttttgtgt   9540
cattcatttt gccacttaat gcatggccta gttctgatgt ttggagcatc tgttaacatt   9600
gaaaatcctg tgcagggtcc tgccttctgt tgttatataa ctattttacc tagcatttct   9660
tcctattcat catataagtt ctctaagggc agagatcatt tttaatcctt tcatgggct    9720 aaatatgagg ttgattttta gtataaggtc tgcagtccct taatcaaaat ctttaggggc   9780
cgtatgtatt tgggaaatca gatttctttc agattttaga aaagtaataa gctgcatcat   9840
gtacctcggt acttaacacc cccagcagca tctgggatag cactttgtaa tctaaatgta   9900
ttaaaatttt tggtgtgaga catattctcc agcgaggagg tctaaggcag gatcctatat   9960
ttaaagattt ctatttctat agcaaaaaat gattattcac actaaagtgt gataatgaca  10020
taaataggct cctgttagtt caggtcagat atgcttttgc taccaaatga gttatgatga  10080
aatgtagttt ggattgagtt gggttttcaga attgtggata atggattgtg gagcttcact  10140
gattcttagt gtactctcta tttatagagc tgacaatgcg attcttctgt tgtgtactgc  10200
tctgtgccag tctagacttc tcttttgggg ctcttagctc cagtatcttc ttcccatcta  10260
tttttcctgt acactacttt cctcatctca gtcctctgtt ctcaaacttc cagtgttta   10320 ccattaattg tccccaatgt ttctgtgaaa agaagctact tttcatacc cctaaagtct    10380 caaaattatt acagagaggg tgtgatagta atgcacttag tgttgagctt gggaagaaag  10440
cattgcattc cttatgccac agtcttctct acagggaata ctaaggggtg accatgtgat  10500 atggggaag cagggcattg tgatggcatt cagctgacag aactactgat gaggtttcca    10560
ggtcttggcc tggaagaagt taggcattct tggcctgcaa ggaggtttca gactcatcca  10620
agacctccta taatctgact ccagtctaac ctctcagact gagtcactgt tcctcagatt  10680
taggttttac tttttttgtct aaacttgcct actgaccatc ccgtgaatga catactgtat  10740
atgcttttct ggcttcatgc attttttccca acatttctct tagtgatatt tttcttgtgt  10800
atttaatctt atgatactcc tttggtagat ccggtagtat tctgaaactg gaattgatat  10860
gacttgttta gaggctcatg gttttttgttt tgtgttgtgt tttaaaataa tcatgagttt  10920
```

```
tttatgtgcc ctgatacctg gcaaagttgc caaaatgaag ccacgttaga catgccacat   10980
ttatttagag acacatttgg taagaactag gaatcttagc atgttggagc tggacattac   11040
attgtgagta taatgtttta taaatcagga agctcaaatc agcaaagctc cagagaggtt   11100
aagtgtcttg ctttaggcac accgcttgat agtggtggaa ccagaactcg attatttttt   11160
ttgaaagttt ttaaatccca tgttttttct ttttggtgtt agagctaata ctttcatttg   11220
acttgttttc tcttctttta agcaaattta atactccttc tggatttgga aaccatttc    11280
ctacctggtt tcaacccata ggagaaaaaa atcattctcc ttcaaggtgc aacactggta   11340
aaagtaggat tttgcaggcc atatctgatt aatcaaatga tcagaacggt ctatgattag   11400
agataagata gactcttcta tgattttat tgctaacaac aaaccaattt aaattatact    11460
tttggtgttt caagcttagt aagtttaaag tgtactaagg acccagctgc attctgttcc   11520
cctgtgtgca tctccaactt gaagagaagg ttcagtcatg ccatgtgatt gatggtgtta   11580
agtgccacat tttatttttt taaacctctc tgctgtgtat tgattaaata aaagcaacaa   11640
tgattaaaga aaatgatgaa aaaaattgat gctagtttga atttataaaa tgagaaatta   11700
agctccagat ggagcctctt agttaccaga ggaaaacagg gaattattat cattaaaact   11760
caaagctgag gagccttggc ccttttggat atatctaaat tttcatgaac cagttttgt    11820
ttaggaaaat agtcaccaaa tgagataaat atttaaagtt ttctaaaaat tgcacccgtc   11880
tcttgtcact gtgtttccca ccggccttaa atgtcctgcc tgttagactg tacctgtggc   11940
agagtgctaa gccatatgtg ctctcagtgg tgtgtcagag ttttctcttc ttttctgtaa   12000
tcacatattt tagttttga gtgtgaagct aatgtagatt gtcctgtcct ccttgttgtg    12060
aatgtccttg gagaagtccc ttcccatcct gggcctcaag ttcctctttt gaactatgaa   12120
gagattgtaa actgtgaaga gtcccttcat tctctgagat cctatgattt gactgaatat   12180
ttatttattt ttattttgag acagtgtctt gctctgtctc ccaggctgga gtgcagtggc   12240
acaatctcag ctcactgtaa cctctgcctc ccggtttcaa gtgattctcc tgcctcagcc   12300
tcccgaatag ctgggattac agatgtgagc caccacgcct ggctaatttt tgtatttta    12360
gtagagacga ggtttcacca tgttggccag gctggtctga aactcctgac ctcaagtgat   12420
ctaccacttt ggcctcccaa agtgctggga tataggcgtg agcctctgtg cccggccttg   12480
actgaatact ttaaaaactg aataattttt atttgattta aaaaggaata acaatatcca   12540
taaccaaaaa aagacaaaaa aattgcagca tgcaacaaga aaaatctgaa ctttggcttg   12600
agtttccagg acttgtagtc aagtatttat gtgggttgtg aggggataag agaatttagg   12660
gtagctttat acagtgttac catttattct ttttgttgt tttattttt tcttatgttt     12720
ggttggtgtc accatttatt cttttgtatg ctgtttagcc tctggagagg gcatctctgt   12780
gtttatagaa gaaaaatgtg actctcatgt tgtacacagc cctagactgg acatcaaggt   12840
cttctaactg tcctaagctt cttaggaaga tattgtctat gtattttagt ttggaatcag   12900
actggcacag gactcggcat gcactataac tcttactgtt ctattttttc agcttggatt   12960
tacactgggc aacgtggttg gaatgtatct ggctcagaac tatgatgtaa gtggccatat   13020
ccatgacttc cttgattcca tgtaactgtt ttagagtgac ttttctttgt ttgaggtaag   13080
gtgtgacttc cagcataaat gtagtccata tggctgaggc aaaactcctg aatattgtag   13140
aatggtttgc cattgtttga aaagtaatc caactcatga aacagctgtc ctccatatca    13200
ccacaagagg gcaaaatccc ttcagtttag ctgggctcat gatcatcctc agctgtggct   13260
tgttagccga gagtaatatt aagttgggct cttaaaattc tttgggaaat catgtgataa   13320
```

```
gtgagaattt aaaaattaat tggataatat tttcagcccc actatccagt agtagagatg   13380
acttagaatt ttggagatgc atctgggtag ggggactgaa aaatatagat ctatattcca   13440
tctccaaaat tctaagtgta gcacatttgg ggacagagtt ttgtgaagtt gtattaacct   13500
cactttatag gtggtgatgt tgaaaaccag gtggtgcagc agcctatgaa tggggattct   13560
ggacaggagt ttgaaaaaga caagcaaggg aaacatgata ctaacttgat ttgttataaa   13620
gcttttcata tgacaaaggg aattcctttg tcaaccttcg tttgagtcat acagttttct   13680
aggcaaaggc tacattatgt cacatttatt gtttatatgt acaaccttta cttggcacca   13740
gatcgagcgg aagtgggtat acaaaagtag aagtgggttt cagagaagga gcatacttat   13800
ctgacaactt ctgatatctt tcacatgcag ttataaggct aagaaatacc actattggcc   13860
gggtgcagtg gctcacgcct gtaatcctag cactttggga ggccgaggtg ggcagattgc   13920
tcaagctcag gagttcgaga ccagcctggg cagtgtgacg aaagcccatc tttacaaaaa   13980
atacaaaaat tagccagggg tggtggcatg tccgtggtcc caactacttg cgggattgtg   14040
gcgggaagga tcacttgagc tctggaggtc aaggctgcag tgagctgtgt ttgcaccatt   14100
gccctccagc ctgagtgaca gagtgaaacc ctatcttaaa aaagaaagca aaagaaata   14160
accactattt agcagatctc ttttggagga agataaaagc ttgtaaaacc atttatcttt   14220
ggaggaagag aagtacaaga atattgatta ggtagatgca aaattataat aaccttttt   14280
ctcttcaaag ataccaaacc tggctaaaaa acttgaagaa attaaaaagg acttggatgc   14340
caagaagaaa cccccctagtg catgagactg cctccagcac tgccttcagg atatactgat   14400
tctactgctc ttgagggcct cgtttactat ctgaaccaaa agcttttgtt ttcgtctcca   14460
gcctcagcac ttctcttctt tgctagaccc tgtgttttt gctttaaagc aagcaaaatg   14520
gggcccccaat ttgagaacta cccgacattt ccaacatact cacctcttcc cataatccct   14580
ttccaactgc atgggaggtt ctaagactgg aattatggtg ctagattagt aaacatgact   14640
tttaatgagt agtgtcttct ttatcgtttg cgattttttac taccttttt caaaagaaaa   14700
attgatgagt tttgtatagc tggtcagata caaataatag tgacttcaca gtttagtaat   14760
tataatgggt acttgttaaa catttggtac taaattatgt tgctgcaaag taattaaaat   14820
tagtatctag agctagtttc tggtgaatta ttcattttatt ttgtactgtt gttaggcagc   14880
tctgtagttg ctaatttaac caataagtca atttgctatt catgaagaaa cgattctgag   14940
aatcctgtca ggaattgggg aatgaaaaaa tacacaaaat aatggtcttt gtcccagtag   15000
agttcatagt ctatttagtg tgcatgtttt tccttaatga tgtatttgat ctgacttttt   15060
tccttctcaa aagaatcata cttgggatta caggtacatt tgatgttata tgatggataa   15120
gtgaaaagtt tttaaaggag attttatacc ttttcacatt aaaaaaggta tttatattat   15180
tactttgtag tgattgtctt aagaaaaaat atagcccaaa tgtatagtaa aatcagcagc   15240
tcaagaagaa tttctgcttc tctttgtagt tgatgctttg ttttttcctg cagtcagaaa   15300
ttccttgtat ttgtcaaatg tataatcagc ttgtattgtt tttaaattaa aaaaaatttt   15360
gaataattaa cttttgccat gggacaagat acaaaagtaa tttcatataa agggcctctc   15420
ccacccctgt tctctggctc ctggctcctg tttgacaagt tactgttacc acttcgcctt   15480
atacttttga gaaagagtct gtgcctaaac aaacacgtgt aacacaaata gtaactatac   15540
atggaggtct agccctcgcc ttttttttt cttttttttct ttttaatgg agatcattct   15600
ataccagcat gtaagtagca aggaacctca ttctttttt ggctgcctaa aatttttttg   15660
```

```
aatagatata acataattga tttaatctgc tactggtgaa tgcttaggtt gttcttttgc    15720
tattacagtg ataacttcaa tcctaatgtt attaagcata tcgattcagg gtatagctat    15780
aagatgaagt cctaaaagta taatttagac taaatacaaa tacccatttc gctagctgtt    15840
ttgtttcaga ggacttgttg agcagcttca ctaataatgc cattttttgaa gacatggcag    15900 gttcagaatc aataaactgg aagaattgtt cagagcatct ttttcagac agtgatgaca     15960 ttgattctgt atatgataaa gtgattctgc ttctcttttga caacttgcat ctctcctaca   16020
tggaagtaag ttttattcct gtcaatgttg tctttgtgtg tgacagatta ggattaaatt    16080
atggtttgac ttttcctagc agcgtgatca tgggcaagtg gctttttttt tttttttttt    16140
ttgagacaga gtctcactct gctgcccagg ctggagtgca gtggcacagt cttggctcac    16200
tgcaactcct gcctcccggt ccaagtgatt ctcgtgctgc agcttctcaa gtagctggca    16260
tcaccaccac acctggctaa ttttttgtatt tttagtaacg acgaggtttc accatgttgg   16320
caaagctggt ctcaaattcc tggcctcaag tgatctgccc acttcagcct cccaaagtgt    16380
tgggattaca ggcgtgagcc actgcgccca gcttttttaa acttttagat tcatttaata    16440
ggtaaattgc atgtcacggg tttgtagctt attctttcag aaactcttgc attatctgta    16500
gacgtggacg taaatatcca cctcataggg ttttcataaa aataattga gataatgtat    16560 gtaatgtttc acagtgcttt gcagactatc taataaatag tagctattag tacaaacttg    16620 ttgcttttg gctagttctg cagtcacttt tggaatcagt ttatgaacca cacaaaaagt     16680
ttgtcattat tctgtagtcg ctgttttga tactgatgaa aatttacagt atccacctgg     16740
attgtaccat ctggctcaca agatttgatc ttgaattgtt agcacaatga actacagcct    16800
caaaggatga agtttacct tgcgggtatt aaaaatgcta gaagcttaga aagctgtttc     16860
caaagaggga ttccttgtta ccaaccatga tagcattgct gtggtgtgtg tggtctccca    16920
gagtggctgc tttgggattg gaggtcactt agctattaga aggataggtc tctttatatt    16980
ataccttgta aacaaggctc atttggactt agggcttcct ttagaggtga cacttaacct    17040
tggcaagggg atcatttcta ccagtgggat ccatctagca gatcagttct taaattcggc    17100
ttcatcatgt aaaactgctac acagtgcagg ctgactttgc attcaccatt cagatacct    17160 ctcctagttt tatgttcttg gcagcagtga aaaggacctc agagttctca ggcaagatga    17220
tcttcactga gctatatgtt ggaggagccc agaaccatca tagttttagg gtgtagttga    17280
aaatccttac tgtgaatggg gtttatggca ctgaaagtta cccctcccct gggaattttg    17340
taggaaccct tgccacacag atcaatggag tggtgggaag aagcaccaca agacaggcct    17400 ttttttttc ctttaaaaaa tgtttgaaag ctcctactaa tatggttagg aaaacttctg     17460
ccacatctga ccataaaatg agagttgctc aaaatactag tgcagattac tctgacatgt    17520
gaaatacaag acttcaggat tgatgctaga aaaatacagt gaacttgaaa agcttatccc    17580
taaactgtaa tcctcccaaa caaaacaaaa acaaagcaag aaaaaaagcc ttatttaaaa    17640
ttgtcaaaag aggctgaatt ttatgaagtt accaaaagta tatctttaga cttttcttct    17700
gatttggtat tttatgtatt taagcagtta cctgattctg atttaaagga gcaattttat    17760
ttctcttttt ctaactcatt tacccaatga gtttgtgtga ctatagagaa aagtaggctg    17820
tgtggttttt ctagttgtct atacacattg cctcatagag catatgtacc catggtacac    17880
atgtgtaatg ttttcatttc cactaacccg ttcactccct agatactatg ctggtgtttt    17940
tctgctgagg tctcccacat ttttaatgcc ttttctgagt tattcctcct gaaggaacgt    18000
tatatactgt actggagcaa atgaggcttt tcttaaactt ccagtcttgg gttttgcatg    18060
```

```
tagcatttcc attccttaca gatgaatgag ttcttttttc cctattgact attagggctt    18120
cgccttgcgg aaaggaatag ggtggtgaag ggaaaatatt ttgagatctt gcctgctctt    18180
aatagggagt ttgtgacact tagattttca agtgttcatt ttatacctttt cccaaatctg    18240 gttgcagtgt atttagtcaa gcattgaaga cctaacatat ggcatgtttt gcaaggcaca    18300
gggaaagaaa aatgaactga gaacagtgag accttgtgga agttcccagg gtgggacgtt    18360
gaaaccctgg gtcctgggcc ttcctgaatc acagcctcgg tgggaggatt ttatgaaagg    18420
tacagtgcag ttgcatcatc ttacacagtt gtacaggact gggaccaaaa aaggtgccat    18480
gtaaatagtg catgcaattg tgttcagtgt tcgttcagtg aggacagccc cactgagcta    18540
cctgtgtact caggtggtct cggttccctt tgcgttctaa tggtttgagt ttcttgctgt    18600
attgagagtg attctagtgt ttagagactt tttcaaacat cacggtctcc agatgtgaag    18660
ccaactacct catttattgt atggttgaac aaacagattt gttctgatgt tggaaggaaa    18720
actagctgct tttgatttgt taaaagatgg tacatgagtg tttgtgatat gtaaatacta    18780
atgtgaaaga ttgtatacca tgtacttaat gtctgactta gtggaatttc aaaggcaact    18840
ttgactaagc aaatttgata aagaattggt ttaagaataa gatgcaacta tacttagtga    18900
ctttggctca cagtttcatc atccataaaa tattagaaga taaaattaaa ttatatttgc    18960
aagagacaca agactattaa ggagggctag aagttatcca acagtggagt gatttagatg    19020
acaaggagtt attaatcata tttgccattt cctgtcactg gaatgggtaa ccttgcttgg    19080
cttgaatctc cagttctggg aaagaacagt gctgtgcttg agagcagttt agtgagaccag   19140 actgaaataa acgctctttc taaattggct agttgaatgc attcactact cggaacacct    19200
ggcagcagtt gctggcacag ctttcccttc aggagtgagt caggttctca catagttgaa    19260
tactggccag taattctaag tccacttaat tctaaatcaa cttttctttc tcttttttact   19320 tatactccca gaatcttaca gattgcacct ttgtcctatt gtctgactta ggggcaaagg    19380
atctgtgttc tgtgatggtt cataaatgtg atgtttggct gctctgataa taagagtaat    19440
accctgactc ttgaaaattt aaagcaaatg actttagaga tgttggctgg atcaaatcag    19500
ctgtagcgta cctaacattg gtatttcatt tgggcttgtg aggtcttaac tattatattg    19560
gacaaataat tttggtctaa ctcacagggc agaagcactg atgttcccat taaccatggt    19620
cagtcacatt ctgtggttga agcacatgtt tgtggtggtt tcttttgctc caaagaaat    19680 tttacaactc acagatgctt gatcaattaa gggagtgatt ttatagataa attattgtgg    19740
gaaaacagca cgtgctatca gtagtaactt aaaatcactt aaaacagtgc agtaattgta    19800
ggggactccc tttcccctaa gatatattta gcaaacaact gatgggagaa ataaaaaata    19860
tgtaacacta acaaactaga gggattgaga gctatctcca gtcatgtagc aaggatatct    19920
atcatggaga aaacggcatg gtcttcagga ggagaaagaa gccttgatttt ccagacagtt    19980 gttttctcat gggacacgtt tattgagcat ttacagctta ccacattgta gaagttgctg    20040
ggggatttca agagccatag acagctcttc tccctcaagg ggctcatgta gggatgtgta    20100
ggaagtgaca gatgtgtttg gacctttggc tactacctaa tactttgttt tctcaggaac    20160
aaactactta ttaaatccag aagcaagcca gtctaatata ataataatgc tgtggtctta    20220
attatagttt tggtttccct tataagacac ataggaaagt tttccctccc tcccaaaact    20280
taaccaaggc aatagtattt ctggttagtg acaggtggag agagagatgt taatctcaat    20340
gtatcttctt tcttgacttc cctttccttt tgagacggag cctcgctctg tcgcccaggc    20400
```

| | | | | | |
|---|---|---|---|---|---|
| tggagtgcag | tggtgcgatc | tcagctcact | gcaacctctg | cctcctgggt | tcaagcgatt | 20460 |
| cttctgcctc | agcctcctga | gtagctggga | ttacaggcgt | gcaccaccac | gcccggctaa | 20520 |
| ttttttgtatt | tttagtagag | tcggggtttc | actctactaa | aaccctgttg | gtcaggctgg | 20580 |
| cctcgaactc | ctgacctcat | ggtccgcttg | cctcagcctc | ccaaagtgct | gggattatag | 20640 |
| gcgtgagcca | ccgcgcccgg | ccgacttccc | tttcctttga | ctaatagaac | aacaccagcc | 20700 |
| tctttctgaa | agggaacact | atatgggaat | ttggtgccaa | ggtaaagggg | agccattgag | 20760 |
| gagagatgct | taaaagggaa | tgaaagtggt | gatgaaagag | tactaattgc | catgaggaag | 20820 |
| acctactaag | aatgccttct | tgtggagaga | acttaggata | gaagcactta | agagaaagga | 20880 |
| gctgatggcc | gggcgtggtg | gctcacacct | gtaatcccag | cactttggga | ggctgaggca | 20940 |
| ggtggatcac | ctgaggtcag | gagttggaga | ccagcctggc | caacatggtg | aaacccatc | 21000 |
| tctactaaaa | atacagaaaa | ccagctgggc | gttgtggcac | atgcctgtag | tcccagctac | 21060 |
| tcaggaggtt | gagacagtag | aatcgcttga | acctgggagt | ggaggttgca | gtgagctgag | 21120 |
| atcgtgtcac | tgcactccag | cctgggcaac | agaacgagac | tccatctcaa | aaaaaaaaaa | 21180 |
| aaaaaaaaag | agagagagag | aaaggagctg | acattaggtt | tcgaggtctg | ggtgaggttt | 21240 |
| cccacaaaaa | agatgtcact | ggtttcactc | tgccttggta | ggatgacttg | ggtatctttc | 21300 |
| tactcctaag | aaggtattaa | gaataacata | aaacctagtg | agtttgcaag | gcttagcctc | 21360 |
| cgaagggtga | ctaagacagg | ctttcttttc | ctgtcttcag | aatgaatgga | ttacaaagac | 21420 |
| tagatacaac | tttaggtttt | ctttgtcttc | ttttttttta | atttaatttt | tattttcttt | 21480 |
| ttcttttttct | gtgagcctat | ggcttgtatt | gaaactttag | gttttcttga | gctgtggtgc | 21540 |
| tgagggcagg | aagaagacac | taacagcgaa | gcatgtgttt | gtggttgttg | gaggattcct | 21600 |
| gcagttcact | tgaggtggcg | gaatcttctg | gtggagggat | gccctccggc | gtgggtctgg | 21660 |
| ggttgtgtgc | tcctggtggt | cctagtggtt | ttctttgcct | gtggtccaga | tactgctgga | 21720 |
| tactggcagc | tcctgtggtt | gggccagttt | gtacacttgg | cgttaggctt | gatcagtgat | 21780 |
| gttgctgacc | ctcgcccatg | ctgggtaagt | gtccaggtgg | aagaggctaa | ctccccaggt | 21840 |
| gttgatggcc | accattacta | tcaccagtcc | aataacgttg | actcccaggc | cagctttcac | 21900 |
| ctgcaggaca | caaaccagca | caccctagtc | actctgacca | gcagcagcac | agatccccaa | 21960 |
| gtccccttc | tgttcctgca | gcctatgcct | tgtgcccag | attagttccc | agttgctgcc | 22020 |
| tggggtgctc | tagcattgcc | ttgtagggtg | cacaggactg | tggaaaggcg | ggaaagggac | 22080 |
| aattagagtc | atctccactt | catgcttaca | gcactctcac | tagatttcaa | gtggaagcct | 22140 |
| agaaggtatg | ttagttactt | ggaacaccca | ctctgtggaa | cgtgaagagg | tatttctgca | 22200 |
| gctcactgat | agggaaatgt | gctaaacaaa | actaaccaga | tctctgtaaa | gcaggaactt | 22260 |
| ctcagagccc | cgatgcgtta | atacagggaa | cttgtacgag | gggctatatt | acatgaagcc | 22320 |
| tttgctactg | ttacctttt | ttaaggaaca | gctcatggaa | atagtgtacc | ttgagttcac | 22380 |
| ttggggaaac | ggtttagctg | cctctgctca | gctcttcctc | aagaagggga | cacaggcatg | 22440 |
| ctagctggaa | tggagccttt | gcttctttcc | tctgagggaa | ttacacctca | gtgactgacc | 22500 |
| cttttcactt | ctgccttgac | attgacaccc | acaggctgaa | gtgggggatg | tgagagatgg | 22560 |
| tgggctggca | gagccagatg | gaaaaatgtg | tcctgtaagg | atagctggca | tcttcccaag | 22620 |
| gagtaaccag | gcatatagca | tgtagccaag | acaagtcact | agctggcatt | aagttgggaa | 22680 |
| aattgcaagg | ggaaagtgga | tgctgggaaa | ttgtttcaag | caaatggcta | gacgtgtcct | 22740 |
| ctctctcctg | ccgtctggtc | ggggcccct | gggcattttg | gcatggagga | cagcccatgt | 22800 |

```
ttccccacag gtgagagggc aggttctagc agggctaaat taaggagtgt tagagttgaa   22860
agggacccca tggagcatcc agctggaacc tcatcattta gcagatgagg aaattgaagt   22920
caaggtagtg cccaagctgg aatagtgcc  caagactggc tcacttcttg tcacctggta   22980
cctttgaaaa ttactgcctc tgatcatttg attccagtgt agaaagctag gggtcagtgg   23040
tgggggcaca cagcagagga agcgggagac aggagagctg gggtagagct cagcgtgagc   23100
agactgaggg ttacgcagta agatgggagg ggagagggat ggctgggaca ctccattcaa   23160
ggaagtatca cggatgactt agatgagcag ttcgaacagt cgaaaggacc tgaataggct   23220
gagagcagtg actcacacct gtaatgccag cactttggga ggccaaggca ggcagatcat   23280
ctgaagccag tagttcaaga ccagcctgac caacatggtg aaaccccatc tctactaaaa   23340
atacaaaaat tagctgggca tggaggcgca cacctgtagt ccaaggtact ctggaggttg   23400
aggcatgaga atcacttgaa cctgggaggc agaggttgca gtgagccgag atcgcaccac   23460
tgaactccag cctgggtgag agtgagattc tgtctcaaaa aaaaaaaaaa aaaaaaaaa    23520
aaaaggataa aaaaggacct gaatatctgc caccagcctg aaactttttc ttcctttcct   23580
ctatttgtta ctttacaggg ctgcccgaga acaaatttgg ctcccatgaa aaaaaattgt   23640
cagaccatca gtaattcgta tcagtgtttt ccatcctctc ccccccgct  cagccctgga   23700
tactaagtat agcagcaggt gtataggtag aggagtagaa ggtagatagg cccagtgcta   23760
aagtcagcag caaaatatct caaagccatc ttttgtgagc ccagctgaaa atgaaaatga   23820
atggtggacg cttcattttc cattgttgct tcagggtttt cttgcctggg ccggggtgga   23880
gggtgagttg agcagaagaa tcctgttttc tcaaaatacc tttcaccta  ggttcataca   23940
cttcctcatt ctcatcttct gtgaataaac cagtagcttt ctcaatgaat gtctccactg   24000
gcctaatgaa gaaacgaagg caaaacttgt ttgcacaggc tcatgccttc tggaactggg   24060
ccacagcctg tctgttccag cttctctac  ctaggtaccc acttccttcc agggaagggt   24120
tggggagagc acattcttgc tatccttggt gcttatagac caacaaaaac cttttatag    24180
gtgctattct tgctaccaca ctgggtttag cattgacagg ccaggacac  tgctacaaaa   24240
taagctttga aagaaggctg cagagctgtc atccctgtcc tcatggcagc tgggcctggc   24300
agggagaggg caccccaact caccatatct ttgatctggc agtgcccata gctgaagacg   24360
atggcattag ggggattgcc cacaggcagc atcactgcaa aggagatgca catggtgact   24420
gggatcaggg tgtagagggg gttaatgtgc agcgtttcag actagaagag agaattcaca   24480
gaaacattca cgagattagg cttgcatttc ctgtgcttaa tgtcaggagc atgctttaat   24540
gatgacttgg tgctggctaa ccttagcagg acactatgtg gaggggtagt taggtctctg   24600
ccctctgggg catgcagtcc cttgacaacc tgaataggct gatgctgctt acttgctcca   24660
catggaaata tggctttgag ttactcccta gaagggatgt ttgattttt  tggtgttatt   24720
ctaaggaatt ggttcctaaa ctttattctt tagctgagac ttccttttcct taaactcaaa  24780
tctcatgaat aggttgcttt gattgaagtg gggattcctc agtcttaggg tacagaacta   24840
aggtggtttt tttttttttt ttttcctagg gaagataatt gttttatatg ggatttgaat   24900
ccatggtcct gctctcaatg ttgccaagtt ttaactgcac tctgttgctc gcaggagcaa   24960
gatgacggaa gggagaagtt gggggtcatct gagcaatgag cagagagtat ggctctgggg  25020
ttagaaagag cagtaggaga ctatgttgct ggggtcagga ggggccttca tttcctggat   25080
tctgcctccc agaatgggac agatgaagca ttgggtcaga tgcatcacct ttccggctgc   25140
```

```
ttggccaggc taagatctgg ccgttgctcc cctcccttat tctattcaca acaaattggt   25200
ctgaggttgt ggagcaaagc tgaccttgct cccaatcctc agaacttccc ggaggacagt   25260
gaaactcagt ggaggctgtg atgattgtct gagttgtgag ctcagtcttt tcagctgtgt   25320
gtgttttacc tccattttct gtggctacct ctttggccct actcaggttt tatctcagga   25380
gagaaaggtt gataatgatt gcggggaatt gaaatgatag ggtttgaata ttattttgta   25440
tgttctttgg tttccactca gggctgcccc taaactaatc ctactctttt ggacaaaggt   25500
ttctagaact cttgctatga tttattagtg tatctttta tttactagtt gctatttgaa    25560
aaacttcatt tttcaaaata ggaattgaac accaattagt gaaggctgtg ggcagtaacc   25620
agaggagagc ctacagctac ggaagctgcc ctgagccagg cctgccactc caggcccctg   25680
ggacagcctg tctggatgtc tgggagctcc gcattactca ccaggctgca caggatgggc   25740
aggaagatgg tgatggttgc tgggttgctc acaaactcag tgacaatgga cacgaggatg   25800
catgccagca gggtgacagc ccacggtggg aggctgctca gggacaacat ctggttccca   25860
atccatgtag agaggccaga gctctgtagg aagaggtgtt acagtaagaa gaaaggagaa   25920
gaagcacatc ccagctagag atcttagact tcagaaggtc agggatgttg gaaggctgga   25980
cgaccaggga tcctctgatc tttagtctga ctggaaccag aggtgttcct gattttatg    26040 gttcgatcat ttttgtagtt cagaaaattg gtttttatga ttgcacaaca ttcagtgttt   26100
gggtttcgtc atgggacatg gagagccacc ctaattgcca tgatccttct taggactttg   26160
ccatgacaac ttgtcagagg ttggagatct ttgctcctca acttcagtct cgttacccctt  26220 tctctagcct ctgacatcct taccctgtgc attgattcga caatgccctt cacagagtgc   26280
caagtatagc catttaatct gcttttgaaa ccagtttatt ttgttaccta aaaaagggaa   26340
aaatttatca acatctgtgg atagtagcct ttcctgtgtt tttaaggaga tgaacaggca   26400
gggctgagca ctggaggttt tacaggagta ataaagtaga gggggataaa agtctatttc   26460
cacttagtgg agaaggtgcc tcttaagtgc catagaggct ggtcattcag ccccaacctg   26520
ttttaggttc aaatctcatc atggctgaca ttagttctac tatctgtcag gattttttt    26580 ttaattaaga ggagggtctt gctctattgc ccagggtcca ggatgagtgc agcagcatga   26640
tcacagctca ctgcagtctc aacctcctgg gttcaagcaa tcctcccacc tcagccttcc   26700
aagtagctgg gaccacaggc ataccatc acgccctgct ctttttattt gtagagacag     26760
agtctttcca tgttgcccag gcctgtctca aacagacctg ggcttaagcg attctcccac   26820
gttggtctcc caaagtgctg ggattatagg tgtgagccac cgcacctggc ctgccagtgc   26880 ttttttgaaga cacagatatg aaggcatatt gaccgtcctg aatttattcc actagcaaca  26940
gttacacaca tccacttaaa taatgaaca ttctggctgg gtgaggtagc tcacacctgt    27000
aataccagca ctttaggagg ctgaggaagg taggtcactt gaagtcagga gtttgagacc   27060
agcctggcca atgtggtgaa agcccacctt tactaaaaat acaaaaatta gctaggtgtg   27120
gtggcacgcg cctgtaatcc cagctattca ggaggcagag gcaggagaat tgcttgaacc   27180
cgggaggcag aggttgcagt gaaccgagat tgtgccattg cactccagcc tgggtgacag   27240
agtgagactc tgtctcaaaa aaataaaaaa taaatgaata aatattccca cttggaatga   27300
ttcatttggt tggaagatgt tcacctgcaa atagggaggg ctacctccct ctcctaaaaa   27360
atgaaaggta tcattgagtt ttgtattaaa aactccaggt tgccatatgc atcctgcctc   27420
ccttcctctc tctcttctat ggtgacaggc tctgcctttt cccatggtac cctagaaact   27480
gcgaatgcaa tgacaatatg gagagcaggg acagaaagga aggtgagaca tttatgattc   27540
```

```
ctcaagctct taagtcctgc tacacatgtt ttactattaa ataccgcctt ccctacactg    27600
ccagcatgtt acttttttctc ctctcttcca aattcatcaa aagctcattt catctctaca    27660
gtaccctggc cacctcctgg caagctcata gacaactgag gaccaaaggc cttcagaatt    27720
ctctctgttg tagccacttc accttgtaga acttttcttc cttttttttcc tctcaactca    27780 ctgagagctt acaaacccaa tatgtgcaga ctgcatcaat taatgcttgt ttcagagccc    27840
caaggcctcc aggaactctt taattgttcc ctctggtaac acattaaacc ttgctcattg    27900
gacagaggca ggggaggaac agcagttagt tgaatggaaa tggtacatta tataaagaga    27960
tggagtttta cttaacgtta tccaaatagt actggtaagt aaagtgaaat aattttttt    28020 ttcttttttga dacagagttg tgctctgtca cccaagctgg agtgcagtgg caccatctca    28080
gctcactgca acctctgcct cccgggtcca aatgattctc atgcctcagc ctcttggta    28140 gctgggatta caggcatgtg ccaccatccc cggctaaatt ttttttttt tttgagagga    28200 agtctcactc tgtcgcccag gctggagtgc agtggtgcga tctcggctca ccacaacctc    28260
tgcctcccag gttcaagcaa ttctctggcc tcagcctccc aagtagctgg gattacaggc    28320
gcgtgccacc acacccggct aattttttgta tttttagtag agacgaggtt tcaccatgtt    28380
ggccaggctg gtctcaaact cctgatctca ggtgatccac ccaccttggc ctccccaagt    28440
gctgggatta caggcatgat ccactgtgcc cagtccctgg agttttgctt ttgtcaccca    28500
ggctggaatg cagtggcacg atctcggctc actgcaacct cctcctcctg ggttcaagtg    28560
attctcctgc ctcagcctcc caagtagctg ggattaaaag tgtccgccac cacgcctaac    28620 taattttttgt attttttagta gagacaacgt ttcaccatgt tggccaggct agcctcaaac    28680
tcctggcctc aagtgatcct cctgcctcac cctccttaag tgctgggatt acaggcgtga    28740
gtcaccatgc ccggcctagt aaagtgaaat aatttattgg caattatttt tccagcagaa    28800
ctattttata ctatgatttg aaataaatta gacttcaaag ttagacaaaa acacaatcaa    28860
aggaagtctt aattctttaa actcttggta tgaaaacatt ttacaatgga ttttcttcac    28920
taatgtcaaa actgaaatta tttcaaactc tgtaggaatc acatatatgc tacctaaatt    28980
attattaaaa ttagtagagg cagtaggctt tacagaaata actgtactat ctctaatatg    29040
tgcacaattt tgttttttatt gttttttttt tgttttttgtt cttgtttttt gttttggtgg    29100
caggggatag ggtctccctc tgtctcccag gctggagtgc aatggtggga tcttggctca    29160
ctgcagcttt gaactcctgg gctcaagcga tcctctcact tcaacctcct gagtagctgg    29220
gactacaggt acgcaccacc acactgggct aactttgtt tttgtagaga taggatctta    29280
ctatgttgcc caggctagtc tcaaactcct ggactcaagc aatcctcccg ccatggcctc    29340
ccaaagtgct gggattacag acatgagcca ctgtgcccag cccaattttg gttaaaaaaa    29400
aaaataaaat cttgccaggc caatcttgtc agaggccaaa actaacaact gaaattcaat    29460
aaagataaat ataaatatcc cgaacttgga atgagaaata ttgatggcat atatatagga    29520
tggggtgaag gtccagtaat gatgaacagt taaaagaat gaagggttct aattgactgc    29580
agttttaata taattgttga catgagtgcc aaggatgctt tataaagct tccataaaaa    29640 tgcagggtgc tgcttgaatc agaggtgaga gatgggctt gggtaatata actactctac    29700
ttggcagtag actgaccacc ccatagacta tgtttgaata aggccaagtg tagtgagtcc    29760
tgaggagaga gaccagatgg tatgggtcac tactacttga ttttttcatg ttaataatta    29820
ttatctagga gagggtccca gagaacagag ctagagccaa cagtggacag acaacatgca    29880
```

```
gaagacctga gctgaaaata aggaacaatt attctttgtt ccctgcccag ggagtacctt    29940
gtcactggaa gtgtccaagc cagaagtgcc atggagggga atctcaccat gggcaggaga    30000
taggactcat tgttttctaa ggttctcctt agtggagtat tctgtgacct tattattaat    30060
aatgcagata gtattttggg ccatgaaaag tgaaccaagc cgggcacagt ggctcatgcc    30120
tgtaatccca gtactttggg aggccaaggt gggtggatca cttgaggcca ggagttcaag    30180
accagcctgg ccaacatggt gaaactccat ctctactaaa aatacaaaaa ttaagctggg    30240
tgtggtggcg tgtgcttgtg atcccagcta tttgggaggc tgaggcatga gaattgcttg    30300
aacctgggag gcaggggttg cagtgagcag agatggcgcc actgcactcc agcctaggtg    30360
acagagtgag actctgtctc aaaaaaaaaa aaaaaaaaa aaaaaagag aaccaagttt    30420
agcatgggat aatgcatgta gatgagatgg agggagaaat agtctgaacc ttaacctaat    30480
tcattcttaa gattgttttc tattttatgg agggctaaca ctttaggaaa ttcaatcatc    30540
ccctcacatc cccaccccac ttaaaagatc tcatccaaaa tcctcccagt cagaaaatca    30600
agaagcattt acatcagctt tagcctagat ttccaaagg gctcagtct atgtattgtg    30660
gacagacagt tcaccatgtg tcacttggag catctctggt cccttacaga gatcgcctat    30720
taccactcct attacctatt acctatgtct atctcctgtt accatctcct attgccactg    30780
tcaaatccca gaaggagatg gctgcaaact ccaataaacc ttttgcttgt agcagcatgg    30840
gccccataga tgaactatca atgcccatgt gtcatgactg tgtggcacag cccatctgtt    30900
cctctgttcc tagtagcgct gagaagctta gggcagcaga ggacatccat cctgctctat    30960
tgtttccctt cccagggact ctgtgaacat tctcagctgc tttgagtctt tcctcccatg    31020
cccataatga ctcattaggt aaagatgctg gaaaagtatt tgacccataa gaacagaatt    31080
caagccgggt gcagtggctc atgcctgtca tcccagcatt tgggaggcc gaggcaggtg    31140
gatcacttga ggtcaggagt ttgagactag cctggccaac atggtgaaac cgcgtctcta    31200
ctaaaaatac aaaaactagc tggcatcatg gtgcacgcct gtaatcccag ctacttggga    31260
ggctgaggca agagaatcgc ttgaacccag gaggcggagg ttgcagtgag ctgagattgt    31320
gccactgcac tccagcctgg gtgacagagc aagactgtct caaaaaaaaa aaccccaaaa    31380
aaacagaatt caagaattac cttgctacca gaagccagag catagcctcc cccaaccaga    31440
atgacaatct cccagggcat ggtcttctgg aagtccttcc acgtgatgat gggctcggtc    31500
cccagtgagt gctcctggtt ctctcctgga ttagagagag atgtaaagcc agataaaccc    31560
tgatggacgt gatttgtgga gacaggagcc taattggtga agtggatgat ttgggatact    31620
gctatttggg gcggggccg ggagggggt gggaatctga aggaccttgg taaatctctt    31680
tgggagtatt agtctgattt gggtattctt caactagagc tacccccagt ttcttccctt    31740
ctctcaccat cattcttttt cccaaagcag ggcttcttcg ctggaatgag gaagaggagg    31800
aagccaagga agacagagac tgtggcatca gtacggtagc ctttcctagt aaagagacaa    31860
gcatagctga ggagaagggt caggaatttt caggagtaac atgatgtctc ggagcagtct    31920
gtccgaacac agtgcctctt tttaggactt atctagaggt aacattaagc ttagttcttg    31980
ccagttgctg ccacgctatc cactttggat ttaatgggca atggcgaatg tctggaggca    32040
gggcctggct agagtagatg tcttaatgtg aatttgtgag cccgttaatt ggggcaagtc    32100
ctagatggag tgatcaggag tggagttggt tagataaagg agaatagaag aggatgagac    32160
ctctttccta tgaaggccac acctccagtg gcctcccttc tcaagtgaga agttgatttc    32220
ttctttacag ttggtacttt atagatgttt cctcctttaa ctttcataac cacctatgag    32280
```

```
gtaaccaagc ttccaagagc ttatgtaatg agactacatg cagcactgga ttccaacccc      32340
agaccgggac tccaaagagt gttttttcctt cctgatttca cactgcagcc tccctaaaaa      32400
gagtggattt cctggggaat gaaatcttcc tggcttcata tctgcccctg agagtctatg      32460
aagtcttgcc tgaagaattg gggtgagggg gttgttctta aggaggaaat gatatcactt      32520
acttttcaaa gaaagaatcc cagccaggga caaagccagg ctcccgggta aaccacagta      32580
cggtcatcag gatgaagaaa aatccagtca ccatttctgg gtagctataa aataaaacag      32640
aaagacccac tcaggaactg agaaatttct cctagctttt tcactttgct tctggaagct      32700
tctgtattta gagtttcaat accctagaca taaaacacac tcactgccta accactatga      32760
atggctgaca gtgagatgag gagaagactg agtggcccca gaaaacatga cattaaccat      32820
gttcctggag aaacttcagt agaaagggca agagaacaca gcactgtaca tttgtaaaat      32880
aatttcaaat acagcctaca aggagagtgc agtgaaatag gcagccccaa acactgtgct      32940 ggtggggagga ggaattgcta caacctttttt gaggccattt gatgatacac attagaagcc      33000
ttaaagttgg tcattccctg gctgggtgtg gtggcccacg cccgtaatcc cagcactttg      33060
ggaggccgag gtgggcggat catgaggtca ggagatggag accatcctgg ctaacacagt      33120
gaaaccccat ctctactaaa aatgcaaaaa attagctggg cgtggtgtca cgtgcctgta      33180
gtcccagtta ctcgggaggc tgaggcagga gaatcgcttg aacccaggag gtggaggttt      33240
cagcgagcca agattgtgcc actgcactcc agactgggca aaagggtgag actccatccc      33300
aaaaaaaaaa aaaaaaaaaa aaaaatagtt ggtcattccc atcatctaac cagaaatgca      33360
tactgagaca ttaattacct attaaaaaat ggaagcatcc tctatatcca atggtatttc      33420
atgacactga atacattttg atacaactct gtgttaaaat gagatgcatc cattgataat      33480
cccatttcca cagcagagtt aaggatgtgg aacatactgt actgagagta caaagttgag      33540
ttgagaaagg caaggtatac aacagtttca gtgtggactg aatttttacca aaaatacata      33600 agagttttgc acaaaaaagc atggaaagaa gtgttaacat ggggtgctaa gaatccagtc      33660 aatttttgatt ttttttctta tactgtcttg tatttttgaa atgttctaca atgaacatgt      33720 attccttttta taacttaaag ctttaaataa gacagtgtct acctggattg ttttatgcaa      33780
agttgtatgt gccaattgcc ataaaaggag aaatagcact aaataggaag ctgggtccct      33840
gtggaaaagc tgatggaagt ggctgagggt tggttagtga tttcttggac gctctctctc      33900
caagtctgtc tttgatactg ccttatacc taaatatagc acagagtctc ccatctccct      33960
gggagtgata accgcaccac tgtggtggcg cgtctgagca atgagaggtg gcctggcttt      34020
ggaaggaatt cacatttttcc aagagggtgg ctgtgctgtc tttcccttct tctgcctctg      34080
tctgctccat ggtcagcact ccacccccatg ccatggctat accctggact ctgaatagag      34140
caaaggggaa gggtggccac ctgaaatctg gccagcttg ctttg                       34186
```

<210> SEQ ID NO 13
<211> LENGTH: 13940
<212> TYPE: DNA
<213> ORGANISM: Homo sapiens

<400> SEQUENCE: 13

```
aagtcgacga ggggttccgc ccccccgcg catggggagg taggctcgga ccggcccgcg       60
gagctgctgc agtccttcgc gccctcctcg ccctccccac cgacatcatg ctccagttcc      120
tggtgagtgg agctgccgaa gagcggggcc cgctgcctgg ggcgtgcctc ggaccccatt      180
```

-continued

```
tcccccttga ggattgccga ccccgccgac ccggcctggg cgtgggtcca gcggtccctt    240 cgtccccgc gcctggtcgt cgcctcgcag ggcggccgtt ttcttcctgc ctccccagaa     300
aatccctttg ccaatatttt tctgcagcca tccaagtccc taaaactttg aggtgtcaga    360
gagtgtgcgt ttccagagct tcttattgtg tgccgcgccc cgcgctcatt gtgcaatctt    420
tgtattaaag cttgtgtggt ccttgatgac ttttcgtagt ccgcccccct ttctttctgc    480
gctcctgttc cattacatgg tcgccggccg gtccctgctg tggagccctg ctagttggct    540
tttctgagga ggtaggaagg ccaggaataa accgtaaatt agccacctca cgaagtccga    600
gaggctaagt cctcatcaga cctttcagag ttggaggaat gagtcagaca ctggtataca    660 agtaatttt cccaaaatgt gtaagcatga gtaagcagac tatttctctt ggctccttat     720
ttgagttaaa aacgagtttt ctggcaaaac tcggtatatt tcaaaaattg cttggtgaag    780
gttccaggag ttgctcatca aattttcaag tgaaagtttt tctgccaagc tattgtgcat    840
tcaaaacttg atgctttcaa cctctatttt tttttatttt ttatttttttt tgagacggag    900 tctcgctgtg tcgtcaggct ggagtgcagt ggcgcaatct gggctcactg gaacctccgc    960
ctcccgggtt caaccgattc tccctcctcg gcctccggag tagctgggat tacaggcgcg    1020
caccaggatg ctcagctaat ttttgtattt ttagtagaga cgggtttcac caagttggcc    1080
aggctggtct cgaactcctg acctcaagtg atcaacccac ctcagcctac gaaagtgctg    1140
ggattacagg cgtgagccac tgctcccggc tcaaatgctg tatcttttt tgttgtttgt     1200 tttaacggag tccgctctgt tcgccaggct ggagtgcagt agtgcgatct cggctcactg    1260
cagcctccgc ttcctgggtt taagcgattc tcctgcctca gcctcccgag tagctggtgc    1320
gcgccagcag gcccagttaa ttttgtatt tttagtagag acggggtttc accccgttgg     1380
ccgggatggt ctcgatctcc tgacctcggg atctgcctgc ctcagcctcc caaagtgctg    1440
ggattacagg cgtgagcctc gcgcccggc cccaaatgct gtatctttat caaagagatt     1500
aaaacacaaa atgcacccct tttgtccttt tgaaagatgg taatggattg ttaaatccaa    1560
ttagtcaaaa gagtgtcctt aatctgccca gctaagacag ggctgctcct ttgcctctag    1620
gagtttctgt agtgtcctaa ctagatgtta gtttaggagt tcagaataat gacagtcatt    1680
ttcttgtagt aaacactaga ttaaaagcgg tatcacttag ctccagagta tagaatgatg    1740
taattgagct gcttactata tctgttgctc attgataaac tgagaggaca tgattcaatt    1800
acagttaact ttctaagtgg ttttgcagaa tgagtctatt tggttttgca ataaactttt    1860
actgtgtgtt aattttttt tttttttttt tttttgaga caaggtttct ctttgtcacc      1920
taggctagag tccagtggca caatcatggc tcagtgcagt ctttaattcc tggcctcaag    1980
cagccttccc acctcagcct ctttagtagt agctaggact acaggcccgc actaccaccc    2040
gtgactaatt ttaaaatttt tttttgtag agacaggtct tgcctaggcc tcccacagtg     2100
ttgggattac aggcatgagc caccactgtg cctggtcaga ttctgatttg agaattcaga    2160
attctcagta tttaaggaga gatgctaaag ctgtcaatta tattcctagc tcagaagtaa    2220
ctgaacactg atgttctctc accctctggt cttccacctc attgcttttt tttttaaata    2280
agtggatagc attacttttc acattgattc cacctctgtc aaatgagcca ctgactctaa    2340
agttgagcaa gtatttctct ttgtgtgcag tcatttcatc tattaaaaaa tgaccatcat    2400
gttctagtgt ttaagagatt aaacttcaga gtcagacttc tcagtttgaa ctctgcctcc    2460
catcattttc aagctgtggt agcgtgggtg ggctattgaa attttctgtg ctcccatttc    2520
cacatctgaa aatgcaaacc cacctcacag ttttgttgtg aggattaaaa atgagttaac    2580
```

```
acattaaaga acttaaaaac aggagcactc aacaaggatt cagatagtgt tcagtttttc    2640
ttttgcaggg ttcatttgaa ccctgattga gtttcttctc aagtggggat tagcttctct    2700
cagaagggta ggtgatagga aaggtttaga agtgatgaaa cagtcacaag ttaagcagtg    2760
cgttgtcatt acacattttg gaaccgtcta agatgtttct cctacagttg tgatttgtgg    2820
acagtttgaa aaccactgca cttgcttgtg ttggtgataa cgtccttcca ttattcatat    2880
tcctcctcag attaaaatat tctcccttttg tccctatctt gaagagacct tgttcctgtg    2940
attttcccct tttcttttac tgcagttttt cccctttatt attactattt ttaatagtgg    3000
agatagggtc tcactatatt gcccaggctg gtcttgaact cccaggctga agcaatcctc    3060
ccacctcagt ctctcaaagt gttggattat gggcttgagc cactgctcct agacttttt    3120 tttttttttt aaatgcagtg cttcagaaat tgtgtgtcg tctttgcgca ggggccattc    3180
tgatctctgt atcattccag ttttagtgta tgtgctgcca aagtgagcac cccccttttct    3240 tttactgcag taaaagacac ctcttttgcag atagttacca acactacctg agggaagcta    3300
ctgcttcctt aatcgtaagg tttagctaga gttatttttaa ggatgctttt ggcgggaagc    3360
taacatgatg gcactgctgg gggctttgtg cacactgcct atgatgttgt tattgtgtta    3420
ttgtaatctg ttgctttttt tttttttgag acagaatctc actctgtcac ccaggctgga    3480
gtgcactggt gccatcttgg ctcactgcac cctccgcctc ctgggttcaa gcgattctcc    3540
tgcctcagcc tccgggttca gcgattctc ctgccttagc ctccgaagta gctgggatta    3600
caggcatatg ccaccacacc tggctaattt tatatttttt agtagagatg gggtttcacc    3660
acgttggcca gctggtcttt gaactcctga cctcaagtga tttacccacc tcggtctccc    3720
aaagtgctgg gattacaggc gtgagctcct gcacccggcc ggttttccct ttatcctttt    3780
tgccttccta aatactcttc aaggccccac tttgatcttt ttccatgagg ccctcctgat    3840
gacttatgct tctgaaacct ttacactatt atgtctttgt tttgttttgt ttttgagaca    3900
gcgtctcact ctgtcaccca ggctggaatg ctgtggtgca atctcggctc actgcaacct    3960
ctgcctcctt ggttcgagcg attctcgtgc cttaccttcc caagtagctg ggattacaga    4020
cgtgtgccac catccccggc taattttgt atttttagta gaaacagcca tgttggccag    4080
gctggtctca aactcctggc tcatgtgat ctgcccgcct ctgcctccca aagtgctggg    4140
attacaggtg tgagccactg tgcctggcct tacactatta cactattatg atccatttcc    4200
tcatttattt aggtctcatg tcttttcagt aacttctgaa taattatctt gcaccttgtt    4260
tgttatgttt atttctattt tgttaattat ttcaccagtt gatggacatt caagatgttt    4320 ccactttttgg ctatgatgag taatcctgct aggaatattt gtatacaggc ttttgtgtgg    4380
atatgtattt cagttctgtt gagtatatac cctaaagtgg gattgctgca ttatgtggta    4440
tctttatgct caacttttg aggaactttt ggactgtttt ccagagtagc tgcaccgttt    4500
tacattctca ctagtaatgt atgacggctt caatttctcc acatcctcgc caacatttcg    4560
tgtagctctt attgttttg ttaaagtaat tctagtgggt gtgatgtagt tcctcattat    4620
ggttttgctt tgcatttcct cagtgactaa tgttgagcat ctttcatat gcttgttgac    4680 tgtttgtagc tttggagaaa tcctttcaca tcatttgtcc atttttatttt ttgttttatt    4740 ttatttattt attttgaga cggagtctcg ctttgtcgcc caggctggag tgcagtggtg    4800
cagtctcggc tcactgcaac ctctgcttcc tgggttcaag tgattctcc tgcctcagcc    4860 tcccgagtag ctgggactac aggcgtccac caccatgcct ggctaatttt tgtattttta    4920
```

```
gtagaggcgg ggtttcacca gttggccag gctggtaatt gaactcctga cctcaggtga      4980
tcccccaacc ttggcctccc aaactgtggg attacaggtg tgaaccactg tgcctggcca      5040
atttgcccat ttttaaattg agttttttg tgtcactcag ttgtaagaat tatttatata      5100
ttctggatac acatcccttta tcagatatat atttgaaaat attttatctc attctgtgtg     5160
ttgtcttttg actttcttga tggtgttctc tgaaacacag atattttaa ttttgatgag      5220 gtccaatttt tttttttggt tacttgtact tttggtgtca tatctaagaa aactatttgc      5280
ccagccccac tcatgtgaaa cacagatatt tttaattttg atgaagtcca atttttttt      5340 ttggttactt gtactttgg tgtcatatct aagaaaacta tttgcccagc cccactcatg      5400
aaggtttacg cctatgattt ctttgaagag ttttatagtt ttagctctta catttaggtc      5460
tttaatccat tttgagttaa ttttttgtata tagtgtgaga taggagtcca cctttattct      5520
ttgcatgtgg atatcccatt gtcccagcac catttcttga aaagattatt cccagcacca     5580
tttcttggaa agactattct ttctatattg agttccttgg cactcttgtt gaaaatcact      5640
tgaccataag cctttatggt gtattcctgg gctctccact ttattccatt gatctttatt      5700
gatcaataga aacaattcag tcttctttcc ttgccaccac agtaatcggc ttttctctaa      5760
tgggtacttg gttttcttaa aaaaaaaatt acctttttaa attcctacat cttttcatca      5820
tctaataggt ccttgtttcc tcagcctttt ctgagtatag gtaccgggag agtgcttctc      5880
aggcagtgct ttcatcatgt tgctgagggc agagtagtca gtgtctccct accatgattg      5940
catgtgaagg aaactcccct gcctctgatg cccaggctgg agtgcagtgg catgatctca      6000
gctcactgta acctctactt cctgggctca agtgatcctc ccacctcagc ctccagagta      6060
gctgggacta cagatgtatg ccaccacatc cggctagttt tgcattttgt tggtagagat      6120
gtagtttcac catgatgccc aggctggtct caaactcttg ggctcaggcc atcctctcac      6180
cttgtcttcc caaagtactg ggattacaag cgtagccatt gtacctggct gccctacctg      6240
cttgttgaag cccaacatct agacctttcc agctttccat acttaattct ctccattctt      6300
taactcaaat tctctttttcc agtcaggcct gtttcttta tgccagtcat cacatgtcca      6360
ttcccatctc gtgccttgat tttccacatt cagttttctt cgcatttcct ttaccagttg      6420
tattagtcca ttttcacact gctgataaag acatacccga gactgggtaa tttacatggg      6480
aaaaagggtt taatggactt acagttccac atggctgggg aggcctcaat catggcagaa      6540
agcaaggagg agcaagtaac gtcttacatg gatggcagca gacaaagaga gagcttgtgc      6600
aggggaactc ctctttataa aaccatcaga tctcatgaga catattcact atcacgagaa      6660
cagcatggga aagacctgcc ctcatgattc agttacctcc cacttggtcc ctcccacaac      6720
gtgggaattc aagatgagat ttgggtggga acacagccaa accgtatcac cagttttaaat     6780 gtgaacactt agcatattta gagcctttaa tatcaacctg aggtatatat ttttcaagta      6840
tgatttctta aaagaatcac ttttgtgtca ttcattttgc cacttaatgc atggcctagt      6900
tctgatgttt ggagcatctg ttaacattga aaatcctgtg cagggtcctg ccttctgttg      6960
ttatataact attttaccta gcatttcttc ctattcatca tataagttct ctaagggcag      7020
agatcatttt taatcctttc atgggctaa atatgaggtt gattttagt ataaggtctg      7080 cagtccctta atcaaaatct ttaggggccg tatgtatttg ggaaatcaga tttctttcag      7140 atttagaaa agtaataagc tgcatcatgt acctcggtac ttaacacccc cagcagcatc      7200
tgggatagca ctttgtaatc taaatgtatt aaaattttg gtgtgagaca tattctccag      7260
cgaggaggtc taaggcagga tcctatattt aaagatttct atttctatag caaaaaatga     7320
```

| | | | | | |
|---|---|---|---|---|---|
| ttattcacac | taaagtgtga | taatgacata | aataggctcc | tgttagttca | ggtcagatat | 7380 |
| gcttttgcta | ccaaatgagt | tatgatgaaa | tgtagtttgg | attgagttgg | gtttcagaat | 7440 |
| tgtggataat | ggattgtgga | gcttcactga | ttcttagtgt | actctctatt | tatagagctg | 7500 |
| acaatgcgat | tcttctgttg | tgtactgctc | tgtgccagtc | tagacttctc | ttttgggggct | 7560 |
| cttagctcca | gtatcttctt | cccatctatt | tttcctgtac | actactttcc | tcatctcagt | 7620 |
| cctctgttct | caaacttcca | gtgttttacc | attaattgtc | cccaatgttt | ctgtgaaaag | 7680 |
| aagctacttt | ttcatacccc | taaagtctca | aaattattac | agagagggtg | tgatagtaat | 7740 |
| gcacttagtg | ttgagcttgg | gaagaaagca | ttgcattcct | tatgccacag | tcttctctac | 7800 |
| agggaatact | aaggggtgac | catgtgatat | ggggggaagca | gggcattgtg | atggcattca | 7860 |
| gctgacagaa | ctactgatga | ggtttccagg | tcttggcctg | gaagaagtta | ggcattcttg | 7920 |
| gcctgcaagg | aggtttcaga | ctcatccaag | acctcctata | atctgactcc | agtctaacct | 7980 |
| ctcagactga | gtcactgttc | ctcagattta | ggttttactt | ttttgtctaa | acttgcctac | 8040 |
| tgaccatccc | gtgaatgaca | tactgtatat | gcttttctgg | cttcatgcat | ttttcccaac | 8100 |
| atttctctta | gtgatatttt | tcttgtgtat | ttaatcttat | gatactccctt | tggtagatcc | 8160 |
| ggtagtattc | tgaaactgga | attgatatga | cttgtttaga | ggctcatggt | ttttgttttg | 8220 |
| tgttgtgttt | taaaataatc | atgagttttt | tatgtgccct | gataccctggc | aaagttgcca | 8280 |
| aaatgaagcc | acgttagaca | tgccacattt | atttagagac | acatttggta | agaactagga | 8340 |
| atcttagcat | gttggagctg | gacattacat | tgtgagtata | atgttttata | aatcaggaag | 8400 |
| ctcaaatcag | caaagctcca | gagaggttaa | gtgtcttgct | ttaggcacac | cgcttgatag | 8460 |
| tggtggaacc | agaactcgat | tatttttttt | gaaagttttt | aaatcccatg | ttttttcttt | 8520 |
| ttggtgttag | agctaatact | ttcatttgac | ttgttttctc | ttcttttaag | caaatttaat | 8580 |
| actccttctg | gatttggaaa | accatttcct | acctggtttc | aacccatagg | agaaaaaaat | 8640 |
| cattctcctt | caaggtgcaa | cactggtaaa | agtaggattt | tgcaggccat | atctgattaa | 8700 |
| tcaaatgatc | agaacggtct | atgattagag | ataagataga | ctcttctatg | attttttattg | 8760 |
| ctaacaacaa | accaatttaa | attatacttt | tggtgtttca | agcttagtaa | gtttaaagtg | 8820 |
| tactaaggac | ccagctgcat | tctgttcccc | tgtgtgcatc | tccaacttga | agagaaggtt | 8880 |
| cagtcatgcc | atgtgattga | tggtgttaag | tgccacattt | tatttttta | aacctctctg | 8940 |
| ctgtgtattg | attgaataaa | agcaacaatg | attaagaaa | atgatgaaaa | aaattgatgc | 9000 |
| tagtttgaat | ttataaaatg | agaaattaag | ctccagatgg | agcctcttag | ttaccagagg | 9060 |
| aaaacaggga | attattatca | ttaaaactca | aagctgagga | gccttggccc | ttttggatat | 9120 |
| atctaaattt | tcatgaacca | gttttttgtt | aggaaaatag | tcaccaaatg | agataaatat | 9180 |
| ttaaagttttt | ctaaaaattg | cacccgtctc | ttgtcactgt | gtttcccacc | ggccttaaat | 9240 |
| gtcctgcctg | ttagactgta | cctgtggcag | agtgctaagc | catatgtgct | ctcagtggtg | 9300 |
| tgtcagagtt | ttctcttctt | ttctgtaatc | acatatttta | gttttgagt | gtgaagctaa | 9360 |
| tgtagattgt | cctgtcctcc | ttgttgtgaa | tgtccttgga | gaagtcccctt | cccatcctgg | 9420 |
| gcctcaagtt | cctcttttga | actatgaaga | gattgtaaac | tgtgaagagt | cccttcattc | 9480 |
| tctgagatcc | tatgatttga | ctgaatattt | atttattttt | attttgagac | agtgtcttgc | 9540 |
| tctgtctccc | aggctggagt | gcagtggcac | aatctcagct | cactgtaacc | tctgcctccc | 9600 |
| ggtttcaagt | gattctcctg | cctcagcctc | ccgaatagct | gggattacag | atgtgagcca | 9660 |

```
ccacgcctgg ctaattttTg tattTTTagt agagacgagg tttcaccatg ttggccaggc    9720
tggtctgaaa ctcctgacct caagtgatct accactttgg cctcccaaag tgctgggata    9780
taggcgtgag cctctgtgcc cggccttgac tgaatacttt aaaaactgaa taattTTTat    9840
ttgatttaaa aaggaataac aatatccata accaaaaaaa gacaaaaaaa ttgcagcatg    9900
caacaagaaa atctgaact ttggcttgag tttccaggac ttgtagtcaa gtatttatgt    9960
gggttgtgag gggataagag aatttagggt agctttatac agtgttacca tttattcttt   10020
tttgttgttt tattTTTTTc ttatgtttgg ttggtgtcac catttattct tttgtatgct   10080
gtttagcctc tggagagggc atctctgtgt ttatagaaga aaaatgtgac tctcatgttg   10140
tacacagccc tagactggac atcaaggtct tctaactgtc ctaagcttct taggaagata   10200
ttgtctatgt attTTagttt ggaatcagac tggcacagga ctcggcatgc actataactc   10260
ttactgttct attTTTTcag cttggatTTa cactgggcaa cgtggttgga atgtatctgg   10320
ctcagaacta tgatgtaagt ggccatatcc atgacttcct tgattccatg taactgtttt   10380
agagtgactt ttctttgttt gaggtaaggt gtgacttcca gcataaatgt agtccatatg   10440
gctgaggcaa aactcctgaa tattgtagaa tggtttgcca ttgtttgaaa agtaatccA   10500
actcatgaaa cagctgtcct ccatatcacc acaagagggc aaaatccctt cagtttagct   10560
gggctcatga tcatcctcag ctgtggcttg ttagccgaga gtaatattaa gttgggctct   10620
taaaattctt tgggaaatca tgtgataagt gagaatttaa aaattaattg gataatattt   10680
tcagccccac tatccagtag tagagatgac ttagaatttt ggagatgcat ctgggtaggg   10740
ggactgaaaa atatagatct atattccatc tccaaaattc taagtgtagc acatttgggg   10800
acagagtttt gtgaagttgt attaacctca ctttataggt ggtgatgttg aaaaccaggt   10860
ggtgcagcag cctatgaatg gggattctgg acaggagttt gaaaaagaca agcaagggaa   10920
acatgatact aacttgatTT gttataaagc tTTTcatatg acaaagggaa ttccttTTgtc   10980
aaccttcgtt tgagtcatac agtTTTTctag gcaaaggcta cattatgtca catttattgt   11040
ttatatgtac aaccttTTact tggcaccaga tcgagcggaa gtgggtatac aaaagtagaa   11100
gtgggttTTca gagaaggagc atacttatct gacaactTTct gatatcttTc acatgcagtt   11160
ataaggctaa gaaataccac tattggccgg gtgcagtggc tcacgcctgt aatcctagca   11220
ctttgggagg ccgaggtggg cagattgctc aagctcagga gttcgagacc agcctgggca   11280
gtgtgacgaa agcccatctt tacaaaaaat acaaaaatta gccaggggtg gtggcatgtc   11340
cgtggtccca actacttgcg ggattgtggc gggaaggatc acttgagctc tggaggtcaa   11400
ggctgcagtg agctgtgttt gcaccattgc cctccagcct gagtgacaga gtgaaaccct   11460
atcttaaaaa agaaagcaaa agaaataac cactatTTTag cagatctctt ttggaggaag   11520
ataaaagctt gtaaaaccat ttatctttgg aggaagagaa gtacaagaat attgattagg   11580
tagatgcaaa attataataa cctTTTTTct cttcaaagat accaaacctg gctaaaaac    11640
ttgaagaaat taaaaaggac ttggatgcca agaagaaacc ccctagtgca tgagactgcc   11700
tccagcactg ccttcaggat atactgattc tactgctctt gagggcctcg tttactatct   11760
gaaccaaaag ctTTTgtttt cgtctccagc ctcagcactt ctcttctttg ctagaccctg   11820
tgttTTTTgc ttTaaagcaa gcaaatgggg ccccaatTT gagaactacc cgacattTcc    11880
aacatactca cctcttccca taatcccttt ccaactgcat gggaggttct aagactggaa   11940
ttatggtgct agattagtaa acatgacttt taatgagtag tgtcttcttt atcgtttgcg   12000
attTTTacta ccttTTTTtca aaagaaaaat tgatgagtTT tgtatagctg gtcagataca   12060
```

```
aataatagtg acttcacagt ttagtaatta taatgggtac ttgttaaaca tttggtacta   12120
aattatgttg ctgcaaagta attaaaatta gtatctagag ctagtttctg gtgaattatt   12180
catttatttt gtactgttgt taggcagctc tgtagttgct aatttaacca ataagtcaat   12240
ttgctattca tgaagaaacg attctgagaa tcctgtcagg aattggggaa tgaaaaaata   12300
cacaaaataa tggtctttgt cccagtagag ttcatagtct atttagtgtg catgttttc    12360 cttaatgatg tatttgatct gactttttc cttctcaaaa gaatcatact tgggattaca    12420
ggtacatttg atgttatatg atggataagt gaaaagtttt taaaggagat tttataccctt  12480 ttcacattaa aaaaggtatt tatattatta ctttgtagtg attgtcttaa gaaaaaatat   12540
agcccaaatg tatagtaaaa tcagcagctc aagaagaatt tctgcttctc tttgtagttg   12600
atgctttgtt ttttcctgca gtcagaaatt ccttgtattt gtcaaatgta taatcagctt   12660
gtattgtttt taaattaaaa aaaaatttga ataattaact tttgccatgg gacaagatac   12720
aaaagtaatt tcatataaag ggcctctccc acccctgttc tctggctcct ggctcctgtt   12780
tgacaagtta ctgttaccac ttcgccttat acttttgaga aagagtctgt gcctaaacaa   12840
acacgtgtaa cacaaatagt aactatacat ggaggtctag ccctcgcctt ttttttttct   12900
tttttctttt tttaatggag atcattctat accagcatgt aagtagcaag gaacctcatt   12960
cttttttggg ctgcctaaaa ttttttgaa tagatataac ataattgatt taatctgcta   13020
ctggtgaatg cttaggttgt tcttttgcta ttacagtgat aacttcaatc ctaatgttat   13080
taagcatatc gattcagggt atagctataa gatgaagtcc taaaagtata atttagacta   13140
aatacaaata cccatttcgc tagctgtttt gtttcagagg acttgttgag cagcttcact   13200
aataatgcca ttttgaaga catggcaggt tcagaatcaa taaactggaa gaattgttca    13260
gagcatcttt tttcagacag tgatgacatt gattctgtat atgataaagt gattctgctt   13320
ctctttgaca acttgcatct ctcctacatg gaagtaagtt ttattcctgt caatgttgtc   13380
tttgtgtgtg acagattagg attaaattat ggtttgactt ttcctagcag cgtgatcatg   13440
ggcaagtggc tttttttttt tttttttttt gagacagagt ctcactctgc tgcccaggct   13500
ggagtgcagt ggcacagtct tggctcactg caactcctgc ctcccggtcc aagtgattct   13560
cgtgctgcag cttctcaagt agctggcatc accaccacac ctggctaatt tttgtatttt   13620
tagtaacgac gaggtttcac catgttggca agctggtct caaattcctg gcctcaagtg    13680
atctgcccac ttcagcctcc caaagtgttg ggattacagg cgtgagccac tgcgcccagc   13740
ttttttaaac tttagattc atttaatagg taaattgcat gtcacgggtt tgtagcttat    13800
tctttcagaa actcttgcat tatctgtaga cgtggacgta aatatccacc tcatagggtt   13860
ttcataaaaa ataattgaga taatgtatgt aatgtttcac agtgctttgc agactatcta   13920
ataaatagta gctattagta                                                13940
```

<210> SEQ ID NO 14
<211> LENGTH: 2450
<212> TYPE: DNA
<213> ORGANISM: Homo sapiens

<400> SEQUENCE: 14

```
gaccggcccg cggagctgct gcagtccttc gcgccctcct cgcctcccc accgacatca     60 tgctccagtt cctgcttgga tttacactgg gcaacgtggt tggaatgtat ctggctcaga   120
actatgatat accaaacctg gctaaaaaac ttgaagaaat taaaaaggac ttggatgcca   180
```

```
agaagaaacc ccctagtgca tgagactgcc tccagcactg ccttcaggat atactgattc    240
tactgctctt gagggcctcg tttactatct gaaccaaaag cttttgtttt cgtctccagc    300
ctcagcactt ctcttctttg ctagaccctg tgttttttgc tttaaagcaa gcaaaatggg    360
gccccaattt gagaactacc cgacatttcc aacatactca cctcttccca taatcccttt    420
ccaactgcat gggaggttct aagactggaa ttatggtgct agattagtaa acatgacttt    480
taatgagtag tgtcttcttt atcgtttgcg attttttacta cctttttttca aaagaaaaat    540 tgatgagttt tgtatagctg gtcagataca aataatagtg acttcacagt ttagtaatta    600
taatgggtac ttgttaaaca tttggtacta aattatgttg ctgcaaagta attaaaatta    660
gtatctagag ctagtttctg gtgaattatt catttatttt gtactgttgt taggcagctc    720
tgtagttgct aatttaacca ataagtcaat ttgctattca tgaagaaacg attctgagaa    780
tcctgtcagg aattggggaa tgaaaaaata cacaaaataa tggtctttgt cccagtagag    840
ttcatagtct atttagtgtg catgtttttc cttaatgatg tatttgatct gacttttttc    900
cttctcaaaa gaatcatact tgggattaca ggtacatttg atgttatatg atggataagt    960
gaaaagtttt taaggagat tttatacctt tcacattaa aaaaggtatt tatattatta    1020
ctttgtagtg attgtcttaa gaaaaatat agcccaaatg tatagtaaaa tcagcagctc    1080
aagaagaatt tctgcttctc tttgtagttg atgctttgtt ttttcctgca gtcagaaatt    1140 ccttgtatt gtcaaatgta taatcagctt gtattgtttt taaattaaaa aaaaatttga    1200
ataattaact tttgccatgg gacaagatac aaaagtaatt tcatataaag ggcctctccc    1260 accccctgttc tctggctcct ggctcctgtt tgacaagtta ctgttaccac ttcgccttat    1320 actttttgaga aagagtctgt gcctaaacaa acacgtgtaa cacaaatagt aactatacat    1380
ggaggtctag ccctcgcctt ttttttttct tttttttcttt tttaatggag atcattctat    1440
accagcatgt aagtagcaag gaacctcatt cttttttttgg ctgcctaaaa tttttttgaa    1500
tagatataac ataattgatt taatctgcta ctggtgaatg cttaggttgt tcttttgcta    1560
ttacagtgat aacttcaatc ctaatgttat taagcatatc gattcagggt atagctataa    1620
gatgaagtcc taaagtata atttagacta aatacaaata cccatttcgc tagctgtttt    1680
gtttcagagg acttgttgag cagcttcact aataatgcca ttttttgaaga catggcaggt    1740 tcagaatcaa taaactggaa gaattgttca gagcatcttt tttcagacag tgatgacatt    1800
gattctgtat atgataaagt gattctgctt ctctttgaca acttgcatct ctcctacatg    1860
gaagtaagtt ttattcctgt caatgttgtc tttgtgtgtg acagattagg attaaattat    1920
ggtttgactt ttcctagcag cgtgatcatg ggcaagtggc tttttttttt tttttttttt    1980
gagacagagt ctcactctgc tgcccaggct ggagtgcagt ggcacagtct ggctcactg    2040 caactcctgc ctcccggtcc aagtgattct cgtgctgcag cttctcaagt agctggcatc    2100
accaccacac ctggctaatt tttgtatttt tagtaacgac gaggtttcac catgttggca    2160
aagctggtct caaattcctg gcctcaagtg atctgcccac ttcagcctcc caaagtgttg    2220
ggattacagg cgtgagccac tgcgcccagc ttttttaaac ttttagattc atttaatagg    2280
taaattgcat gtcacgggtt tgtagcttat tctttcagaa actcttgcat tatctgtaga    2340
cgtggacgta aatatccacc tcataggggtt ttcataaaaa ataattgaga taatgtatgt    2400
aatgtttcac agtgctttgc agactatcta ataaatagta gctattagta              2450
```

<210> SEQ ID NO 15
<211> LENGTH: 144

```
<212> TYPE: DNA
<213> ORGANISM: Homo sapiens

<400> SEQUENCE: 15
atgctccagt tcctgcttgg atttacactg ggcaacgtgg ttggaatgta tctggctcag      60
aactatgata taccaaacct ggctaaaaaa cttgaagaaa ttaaaaagga cttggatgcc     120
aagaagaaac cccctagtgc atga                                            144

<210> SEQ ID NO 16
<211> LENGTH: 59
<212> TYPE: DNA
<213> ORGANISM: Homo sapiens

<400> SEQUENCE: 16
gaccggcccg cggagctgct gcagtccttc gcgccctcct cgccctcccc accgacatc       59

<210> SEQ ID NO 17
<211> LENGTH: 2247
<212> TYPE: DNA
<213> ORGANISM: Homo sapiens

<400> SEQUENCE: 17
gactgcctcc agcactgcct tcaggatata ctgattctac tgctcttgag ggcctcgttt      60
actatctgaa ccaaaagctt tgttttcgt ctccagcctc agcacttctc ttctttgcta     120
gaccctgtgt ttttgcttt aaagcaagca aatggggcc ccaatttgag aactacccga      180
catttccaac atactcacct cttcccataa tccctttcca actgcatggg aggttctaag    240
actggaatta tggtgctaga ttagtaaaca tgacttttaa tgagtagtgt cttctttatc    300
gtttgcgatt tttactacct tttttcaaaa gaaaaattga tgagttttgt atagctggtc    360
agatacaaat aatagtgact tcacagttta gtaattataa tgggtacttg ttaaacattt    420
ggtactaaat tatgttgctg caaagtaatt aaaattagta tctagagcta gtttctggtg    480
aattattcat ttatttgta ctgttgttag gcagctctgt agttgctaat ttaaccaata    540
agtcaatttg ctattcatga agaaacgatt ctgagaatcc tgtcaggaat tggggaatga    600
aaaaatacac aaaataatgg tctttgtccc agtagagttc atagtctatt tagtgtgcat    660 gttttttcctt aatgatgtat ttgatctgac ttttttcctt ctcaaaagaa tcatacttgg    720
gattacaggt acatttgatg ttatatgatg gataagtgaa aagttttaa aggagatttt    780 ataccttttc acattaaaaa aggtatttat attattactt tgtagtgatt gtcttaagaa    840
aaaatatagc ccaaatgtat agtaaaatca gcagctcaag aagaatttct gcttctcttt    900
gtagttgatg ctttgttttt tcctgcagtc agaaattcct tgtatttgtc aaatgtataa    960
tcagcttgta ttgttttaa attaaaaaaa aatttgaata attaactttt gccatgggac   1020
aagatacaaa agtaatttca tataaagggc ctctcccacc cctgttctct ggctcctggc   1080
tcctgtttga caagttactg ttaccacttc gccttatact tttgagaaag agtctgtgcc   1140
taaacaaaca cgtgtaacac aaatagtaac tatacatgga ggtctagccc tcgcctttt    1200 tttttctttt tttcttttt aatggagatc attctatacc agcatgtaag tagcaaggaa   1260
cctcattctt tttttggctg cctaaaattt ttttgaatag atataacata attgatttaa   1320
tctgctactg gtgaatgctt aggttgttct tttgctatta cagtgataac ttcaatccta   1380
atgttattaa gcatatcgat tcagggtata gctataagat gaagtcctaa aagtataatt   1440
tagactaaat acaaatacc atttcgctag ctgttttgtt tcagaggact tgttgagcag   1500
```

```
cttcactaat aatgccattt ttgaagacat ggcaggttca gaatcaataa actggaagaa    1560
ttgttcagag catctttttt cagacagtga tgacattgat tctgtatatg ataaagtgat    1620
tctgcttctc tttgacaact tgcatctctc ctacatggaa gtaagtttta ttcctgtcaa    1680
tgttgtcttt gtgtgtgaca gattaggatt aaattatggt ttgactttc ctagcagcgt     1740 gatcatgggc aagtggcttt tttttttttt tttttttgag acagagtctc actctgctgc    1800
ccaggctgga gtgcagtggc acagtcttgg ctcactgcaa ctcctgcctc ccggtccaag    1860
tgattctcgt gctgcagctt ctcaagtagc tggcatcacc accacacctg gctaattttt    1920 gtattttag taacgacgag gtttcaccat gttggcaaag ctggtctcaa attcctggcc     1980
tcaagtgatc tgcccacttc agcctcccaa agtgttggga ttacaggcgt gagccactgc    2040
gcccagcttt tttaaacttt tagattcatt taataggtaa attgcatgtc acgggttgtt    2100
agcttattct ttcagaaact cttgcattat ctgtagacgt ggacgtaaat atccacctca    2160
tagggttttc ataaaaaata attgagataa tgtatgtaat gtttcacagt gctttgcaga    2220
ctatctaata aatagtagct attagta                                       2247
```

<210> SEQ ID NO 18
<211> LENGTH: 19
<212> TYPE: PRT
<213> ORGANISM: Homo sapiens

<400> SEQUENCE: 18

Met Leu Gln Phe Leu Leu Gly Phe Thr Leu Gly Asn Val Val Gly Met
1               5                   10                  15

Tyr Leu Ala

<210> SEQ ID NO 19
<211> LENGTH: 46
<212> TYPE: PRT
<213> ORGANISM: Artificial Sequence
<220> FEATURE:
<223> OTHER INFORMATION: Peptide sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:

```
<221> NAME/KEY: misc_feature
<222> LOCATION: (46)..(46)
<223> OTHER INFORMATION: Xaa can be any naturally occurring amino acid

<400> SEQUENCE: 19

Met Xaa Gln Phe Xaa Leu Gly Phe Thr Xaa Gly Asn Val Val Gly Met
1               5                   10                  15

Tyr Leu Ala Gln Asn Tyr Xaa Xaa Pro Asn Xaa Xaa Lys Lys Xaa Glu
            20                  25                  30

Xaa Xaa Lys Lys Asp Xaa Xaa Ala Lys Lys Pro Pro Xaa
        35                  40                  45

<210> SEQ ID NO 20
<211> LENGTH: 12
<212> TYPE: PRT
<213> ORGANISM: Artificial Sequence
<220> FEATURE:
<223> OTHER INFORMATION: Peptide sequence

<400> SEQUENCE: 20

Gly Asn Val Val Gly Met Tyr Leu Ala Gln Asn Tyr
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Peptide sequence

<400> SEQUENCE: 21

Ala Lys Lys Lys Pro Pro
1               5

<210> SEQ ID NO 22
<211> LENGTH: 17
<212> TYPE: PRT
<213> ORGANISM: Homo sapiens

<400> SEQUENCE: 22

Met Leu Gln Phe Leu Leu Gly Phe Thr Leu Gly Asn Val Val Gly Met
1               5                   10                  15

Tyr

<210> SEQ ID NO 23
<211> LENGTH: 28
<212> TYPE: PRT
<213> ORGANISM: Homo sapiens

<400> SEQUENCE: 23

Gln Asn Tyr Asp Ile Pro Asn Leu Ala Lys Lys Leu Glu Glu Ile Lys
1               5                   10                  15

Lys Asp Leu Asp Ala Lys Lys Lys Pro Pro Ser Ala
            20                  25

<210> SEQ ID NO 24
<211> LENGTH: 3
<212> TYPE: PRT
<213> ORGANISM: Homo sapiens

<400> SEQUENCE: 24

Asp Ile Pro
1
```

```
<210> SEQ ID NO 25
<211> LENGTH: 12
<212> TYPE: PRT
<213> ORGANISM: Homo sapiens

<400> SEQUENCE: 25

Lys Asp Leu Asp Ala Lys Lys Lys Pro Pro Ser Ala
1               5                   10

<210> SEQ ID NO 26
<211> LENGTH: 10
<212> TYPE: PRT
<213> ORGANISM: Homo sapiens

<400> SEQUENCE: 26

Met Leu Gln Phe Leu Leu Gly Phe Thr Leu
1               5                   10
```

POLYPEPTIDE AND RELATED PRODUCTS, METHODS AND USES

CROSS REFERENCE TO RELATED APPLICATIONS

This application is a 35 U.S.C. § 371 National Phase Entry Application of International Application No. PCT/SG2020/050069 filed Feb. 12, 2020, which designates the U.S. and claims benefit of foreign priority under 35 U.S.C. § 119 (b) of SG application Ser. No. 10201901195V filed Feb. 12, 2019, the contents of which are incorporated herein in their entireties by reference.

SEQUENCE LISTING

The instant application contains a Sequence Listing which has been submitted electronically in ASCII format and is hereby incorporated by reference in its entirety. Said ASCII copy, created on Nov. 4, 2024, is named 049595-190700US-PX_SL.tx and is 94,048 bytes in size.

TECHNICAL FIELD

The present disclosure relates broadly to a polypeptide and related products, methods and uses.

BACKGROUND

Heart failure (HF) remains a leading cause of death and one of the costliest healthcare burdens in modern society. In Singapore, heart disease accounted for 19.3% of all deaths in 2014 (http://www.myheart.org.sg/article/about-the-heart-and-heart-disease/statistics/singapore/75). Treatment for HF remains an inadequate stage-by-stage cumulative add-on therapy, and morbidity and mortality threaten to worsen as the world population rapidly ages.

The underlying cause of HF in most patients is a loss of cardiomyocytes, accompanied by functional derangements in contraction and relaxation. The regenerative capacity of the heart is limited by the inability of terminally differentiated cardiomyocytes to adequately undergo cell division after the first weeks of life.

While recent studies have found that very low rate of cardiomyocyte turnover occurs in adult mouse and human hearts mediated primarily by proliferation of pre-existing cardiomyocytes, the drivers of the proliferation remain elusive. Novel targets, especially novel peptidic targets that can be manipulated to drive proliferation of adult cardiomyocytes, are urgently needed for the HF drug discovery pipeline.

Thus, there is a need to provide a polypeptide and related products, methods and uses that address or at least ameliorate one or more of the above problems.

SUMMARY

In one aspect, there is provided an isolated polypeptide encoded by Sghrt.

In one embodiment, the polypeptide comprises a mitochondrial polypeptide.

In one embodiment, the polypeptide shares at least 75% sequence identity with any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 18, and SEQ ID NO: 22, SEQ ID NO: 23, SEQ ID NO: 24 and SEQ ID NO: 25.

In one embodiment, the polypeptide comprises a micropeptide.

In one embodiment, the polypeptide comprises a homo-oligomer.

In one aspect, there is provided a method of assessing heart function in a subject, the method comprising: determining an expression level of the polypeptide in a sample obtained from the subject; comparing the expression level to a reference expression level, wherein if the expression level exceeds the reference expression level, the subject is considered to have impaired or deteriorated heart function.

In one embodiment, the reference expression level comprises an expression level of the polypeptide in a healthy population.

In one embodiment, the reference expression level comprises an expression level of the polypeptide in an earlier sample obtained from the subject.

In one embodiment, the method further comprises administering to the subject an inhibitor of the polypeptide.

In one aspect, there is provided a method of treating impaired heart function in a subject, the method comprising: inhibiting an expression of the polypeptide in the subject.

In one aspect, there is provided a method of identifying a potential drug for treating impaired heart function, the method comprising: determining a first expression level of the polypeptide in a cell; exposing the cell to a drug candidate; and determining a second expression level of the polypeptide after the exposure, wherein if the second expression level is lower than the first expression level, then the drug candidate is identified as a potential drug for treating impaired heart function.

In one aspect, there is provided an inhibitor of the polypeptide.

In one aspect, there is provided the inhibitor for use in therapy.

In one aspect, there is provided the inhibitor for use in treating impaired heart function.

In one aspect, there is provided use of the inhibitor in the manufacture of a medicament for the treatment of impaired heart function.

In one embodiment, the impaired heart function is selected from the group consisting of: myocardial infarction, heart failure, coronary artery disease, narrowing of the arteries, heart attack, abnormal heart rhythms, arrhythmias, heart failure, heart valve disease, congenital heart disease, heart muscle disease, cardiomyopathy, pericardial disease, aorta disease, marfan syndrome, genetic cardiomyopathy, non-genetic cardiomyopathy, heart hypertrophy, pressure overload-induced heart dysfunction, and damaged heart tissue.

In one aspect, there is provided a pharmaceutical composition comprising the inhibitor and a suitable carrier, adjuvant, diluent and/or excipient.

In one aspect, there is provided a vector comprising a polynucleotide sequence encoding for the polypeptide or the inhibitor.

In one aspect, there is provided a host cell transfected with the vector.

In one aspect, there is provided a transgenic non-human subject comprising a polynucleotide construct encoding for the polypeptide.

In one aspect, there is provided the polypeptide coupled to a detectable label.

In one aspect, there is provided a method of dedifferentiating and/or proliferating a heart cell, the method comprising: inhibiting the expression of the polypeptide in the heart cell.

In one aspect, there is provided a cell produced by the method, or progenies or cell derivatives thereof.

In one aspect, there is provided an isolated polynucleotide encoding for the polypeptide.

Definitions

The term "polypeptide" as used herein broadly refers to a chain of amino acid residues connected via peptide bonds. Further, the term also encompasses an assembly or a complex of more than one polypeptide subunit, such as multimers or oligomers. In some embodiments, the multimers or oligomers are homo-multimers or homo-oligomers composed of identical subunits. The polypeptide may be naturally occurring or synthetic (e.g., generated by chemical synthesis or recombinant DNA technology). Examples of "polypeptide" include gene products, naturally-occurring peptide/proteins, homologs, orthologs, paralogs, fragments, and other equivalents, variants, analogs, multimeric or oligomeric forms of the foregoing. No particular size is implied by the term "polypeptide".

The term "isolated" as used herein in relation to a polypeptide refers to a polypeptide that is removed from its natural environment. A polypeptide may be "isolated" by separating it from some or all of the naturally occurring constituents with which it is associated in nature. Thus, an "isolated" polypeptide is typically at least partially purified.

The term "expression" as used herein in relation to a polypeptide is not limited to an amount of the polypeptide, but also includes the meaning of "functional expression" or an activity of the polypeptide to perform a native function. Accordingly, "determining an expression level" of a polypeptide includes measuring quantitatively, semi-quantitatively or qualitatively the amount of the polypeptide and/or an activity of the polypeptide.

The term "treatment", "treat" and "therapy", and synonyms thereof as used herein refer to both therapeutic treatment and prophylactic or preventative measures, wherein the object is to prevent or slow down (lessen) a medical condition, which includes but is not limited to diseases (such as heart diseases or impaired heart function), symptoms and disorders. A medical condition also includes a body's response to a disease or disorder, e.g. inflammation. Those in need of such treatment include those already with a medical condition as well as those prone to getting the medical condition or those in whom a medical condition is to be prevented.

The term "therapeutically effective amount" of an agent will be an amount of the active agent that is capable of preventing or at least slowing down (lessening) a medical condition, such as heart diseases or impaired heart function. Dosages and administration of agents, compounds, compositions and formulations of the present disclosure may be determined by one of ordinary skill in the art of clinical pharmacology or pharmacokinetics. See, for example, Mordenti and Rescigno, (1992) Pharmaceutical Research. 9:17-25; Morenti et al., (1991) Pharmaceutical Research. 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the active agent of the present disclosure to be employed therapeutically will depend, for example, upon the therapeutic objectives, the route of administration, and the condition of the patient. Accordingly, it may be necessary for the therapist to titer the dosage and modify the route of administration as required to obtain the optimal therapeutic effect.

The term "subject" as used herein includes patients and non-patients. The term "patient" refers to individuals suffering or are likely to suffer from a medical condition e.g. a heart condition/disorder and/or impaired heart function, while "non-patients" refer to individuals not suffering and are likely to not suffer from the medical condition. "Non-patients" include healthy individuals, non-diseased individuals and/or an individual free from the medical condition. The term "subject" includes humans and animals. Animals include murine and the like. "Murine" refers to any mammal from the family Muridae, such as mouse, rat, and the like.

The term "micro" as used herein is to be interpreted broadly to include dimensions from about 1 micron to about 1000 microns.

The term "nano" as used herein is to be interpreted broadly to include dimensions less than about 1000 nm.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object. The particle of the present disclosure may be spherical, substantially spherical, or non-spherical, such as irregularly shaped particles or ellipsoidally shaped particles. The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest length of the particle.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a polypeptide, and related products, methods and uses are disclosed hereinafter.

In various embodiments, there is provided a peptide encoded by Sghrt, or a part/fragment thereof. In some embodiments, the peptide comprises an isolated peptide. In some embodiments, the peptide comprises an oligopeptide. In some embodiments, the peptide comprises a polypeptide. In some embodiments therefore, there is provided an isolated polypeptide encoded by Sghrt. In various embodiments, Sghrt corresponds to the previously annotated 1810058i24Rik, or homologs or orthologs thereof.

In various embodiments, the peptide comprises a secretory peptide.

In various embodiments, the polypeptide comprises no more than about 150, no more than about 140, no more than about 130, no more than about 120, no more than about 110, no more than about 100, no more than about 90, no more than about 80, no more than about 70, no more than about 60, no more than about 55, no more than about 50, no more than about 49, no more than about 48, or no more than about 47 amino acids in length. In various embodiments, the polypeptide comprises from about 40 to about 50, or from about 45 to about 50 amino acids in length. In various embodiments, the polypeptide comprises about 45, about 46, about 47, about 48, about 49 or about 50 amino acids in length. In one embodiment, the polypeptide comprises about 47 amino acids in length. In some embodiments, the polypeptide comprises a short open reading frames-encoded (sORF-encoded) peptide. In some embodiments, the polypeptide comprises a micropeptide.

In various embodiments, the polypeptide is capable of oligomerization or capable of forming multimers or oligomers. In various embodiments, the polypeptide is capable of forming homo-multimers or homo-oligomers. In various embodiments therefore, the polypeptide comprises a multimer, an oligomer or a polypeptide assembly or complex. The polypeptide may be multimer or an oligomer composed of at least about two or at least about three polypeptide subunits or identical polypeptide subunits. In some examples, the polypeptide may be a dimer (e.g. a homodimer), a trimer (e.g. a homotrimer), and in some examples, the polypeptide may be monomer (e.g. composed of no more than one polypeptide subunit). The multimeric or oligomeric forms of the polypeptide may be substantially resistant to heat/high temperature and/or substantially resistant to treatment with ethylenediaminetetraacetic acid (EDTA). In various embodiments, the monomers or polypeptide subunits of the multimer or oligomer are not linked/joined by covalent bond.

In various embodiments, the polypeptide is located in, or localizes to, the mitochondria in a cell, optionally wherein the polypeptide is predominantly located in the mitochondria in a cell. In various embodiments, the polypeptide comprises a mitochondrial polypeptide. In various embodiments, the polypeptide comprises a sORF-encoded mitochondrial polypeptide. In various embodiments, the polypeptide comprises a mitochondria membrane protein. In some embodiments, the polypeptide comprises a mitochondrial targeting signal, optionally a mitochondrial membrane targeting signal.

The polypeptide may be located in, or may localize to, or may be found in the mitochondrial matrix or the intermembrane of mitochondria. The polypeptide may also be located in, or may localize to, or may be found in the cell cytoplasm, nucleus or extracellular region etc.

In some embodiments, the polypeptide is capable of entering a secretory pathway. In some embodiments, the polypeptide comprises a secretory signal sequence, optionally wherein the secretory signal sequence comprises "MLQFLLGFTLGNVVGMYLA (SEQ ID NO: 18)" or portions (e.g. linear portions) thereof, or a sequence having at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identity thereto. The secretory signal sequence may be from about 15 to about 25 amino acids long or from about 17 to about 23 amino acids long. The secretory signal sequence may be about 17, about 18, about 19, about 20, about 21, about 22 or about 23 amino acids long.

In some examples, based on a hydropathy analysis of the sequence "MLQFLLGFTLGNVVGMYLA (SEQ ID NO:

18)", the sequence more likely constitutes a secretory signal sequence than a mitochondrial signal sequence.

The mitochondrial targeting signal sequence and/or the secretory signal sequence of the polypeptide may be cleaved off to produce a C-terminal product that is from about 20 to about 30 amino acids long, or from about 25 to about 30 amino acids long. The C-terminal product may be about 25, about 26, about 27, about 28, about 29 or about 30 amino acids long. In various embodiments, the C-terminal product comprises the sequence "QNYDIPNLAKKLEEIK-KDLDAKKKPPSA (SEQ ID NO: 23)" or portions (e.g. linear portions) thereof or a sequence having at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78% or at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identity thereto.

In various embodiments, the polypeptide or a part/fragment thereof shares at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78% or at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity or about 100% identity with a sequence set forth in any one of:

```
SEQ ID NO: 1:
MLQFLLGFTLGNVVGMYLAQNYDIPNLAKKLEEIKKDLDAKKKPPSA;

SEQ ID NO: 2:
MLQFLLGFTLGNVVGMYLAQNYDIPNLAKKLEDIKKDLDAKKKPPSS;

SEQ ID NO: 3:
MLQFLLGFTLGNVVGMYLAQNYDIPNLAKKLEEIKKDLDAKKKPPSC;

SEQ ID NO: 4:
MLQFLLGFTLGNVVGMYLAQNYDMPNLAKKLEEIKKDLDAKKKPPSS;

SEQ ID NO: 5:
MLQFLLGFTWGNVVGMYLAQNYEMPNLAKKLEEIKKDLEAKKKPPSS;

SEQ ID NO: 6:
MLQFVLGFTLGNVVGMYLAQNYDIPNIAKKLEDFKKDVEAKKKPPSDKS;

SEQ ID NO: 7:
MMQFILGFTLGNVVGMYLAQNYEVPNISKKIEAFKKDVEAKKKPPE;

SEQ ID NO: 18:
MLQFLLGFTLGNVVGMYLA;

SEQ ID NO: 19:
MXQFXLGFTXGNVVGMYLAQNYXXPNXXKKXEXXKKDXXAKKKPPX,
wherein X represents any amino acid;

SEQ ID NO: 20:
GNVVGMYLAQNY

SEQ ID NO: 21:
AKKKPP;

SEQ ID NO: 22:
MLQFLLGFTLGNVVGMY;

SEQ ID NO: 23:
QNYDIPNLAKKLEEIKKDLDAKKKPPSA;

SEQ ID NO: 24:
DIP;

SEQ ID NO: 25:
KDLDAKKKPPSA;
``` and
the sequence of short transmembrane mitochondrial protein 1 precursor (STMP1) or
portions, optionally linear portions, thereof.

In some embodiments, the polypeptide shares at least 75% sequence identity with any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 18, SEQ ID NO: 22, SEQ ID NO: 23, SEQ ID NO: 24, SEQ ID NO: 25 and portions, optionally linear portions, thereof.

In some embodiments, the polypeptide or a part/fragment thereof comprises the sequence "MXQFXLGFTXGNVVG-MYLAQNYXXPNXXKKXEXXKKDXXAKKKPPX" (SEQ ID NO: 19), or potions, optionally linear portions, thereof, wherein X represents any amino acid. It will be appreciated that each of X may represent different amino acids. In some embodiments, each of X is independently selected from the group consisting of A, R, N, D, C, E, Q, G, H, I, L, K, M, F, P, S, T, W, Y and V. In some embodiments, each of X is independently selected from the group consisting of A, D, E, F, I, L, S, M, V and W. In some embodiments, the polypeptide or a part/fragment thereof comprises the sequence "GNVVGMYLAQNY" (SEQ ID NO: 20) and/or "AKKKPP" (SEQ ID NO: 21), or portions, optionally linear portions, thereof. In some embodiments, the polypeptide or a part/fragment thereof comprises the sequence "MLQFLLGFTLGNVVGMY" (SEQ ID NO: 22) or portions, optionally linear portions, thereof.

In some embodiments, the polypeptide or a part/fragment thereof is derived, isolated or purified from a mammal, optionally a mammal selected from human, pig, rat and mouse. In some examples, the presence of the polypeptide or a part/fragment thereof in human, pig, rat and mouse has been confirmed by mass spectrometry.

In various embodiments, the polypeptide is encoded by a polynucleotide or nucleic acid sequence (DNA/RNA) that shares at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or at least about 100% sequence identity with the sequences set forth in any one of SEQ ID No: 8 to SEQ ID No: 15.

In various embodiments, there is provided an isolated polynucleotide or nucleic acid sequence (DNA/RNA) encoding for the polypeptide or a part/fragment thereof. In various embodiments, there is provided an isolated polynucleotide or nucleic acid sequence encoded by Sghrt. In various embodiments, the polynucleotide or nucleic acid sequence shares at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or at least about 100% sequence identity with the sequences set forth in any one of SEQ ID No: 8 to SEQ ID No: 15.

In various embodiments, the isolated polynucleotide or nucleic acid sequence comprises a human Sghrt RNA sequence. In various embodiments, the human Sghrt RNA sequence comprises the sequence set forth in SEQ ID NO: 14: GACCGGCCCGCGGAGCTGCTGCAGTCCTTCGCGCCCTCCTCGCCCTCCCCACCGACATCATGCTCCAGTTCCTGCTTGGATTTACACTGGGCAAC GTGGTTGGAATGTATCTGGCTCAGAACTATGATATACCAAACCTGGCTAAA AAACTTGAAGAAATTAAAAAGGACTTGGATGCCAAGAAGAAACCCCCTAGT GCATGAGACTGCCTCCAGCACTGCCTTCAGGATATACTGATTCTACTGCTC TTGAGGGCCTCGTTTACTATCTGAACCAAAAGCTTTTGTTTCGTCTCCAG CCTCAGCACTTCTCTTCTTTGCTAGACCCTGTGTTTTTGCTTAAAGCAAG CAAAATGGGGCCCCAATTTGAGAACTACCCGACATTTCCAACATACTCACC TCTTCCCATAATCCCTTTCCAACTGCATGGGAGGTTCTAAGACTGGAATTA TGGTGCTAGATTAGTAAACATGACTTTTAATGAGTAGTGTCTTCTTTATCGT TTGCGATTTTTACTACCTTTTTTCAAAAGAAAAATTGATGAGTTTTGTATAGC TGGTCAGATACAAATAATAGTGACTTCACAGTTTAGTAATTATAATGGGTAC TTGTTAAACATTTGGTACTAAATTATGTTGCTGCAAAGTAATTAAAATTAGTA TCTAGAGCTAGTTTCTGGTGAATTATTCATTTATTTTGTACTGTTGTTAGGC AGCTCTGTAGTTGCTAATTTAACCAATAAGTCAATTTGCTATTCATGAAGAA ACGATTCTGAGAATCCTGTCAGGAATTGGGGAATGAAAAAATACACAAAAT AATGGTCTTTGTCCCAGTAGAGTTCATAGTCTATTTAGTGTGCATGTTTTTC CTTAATGATGTATTTGATCTGACTTTTTTCCTTCTCAAAAGAATCATACTTGG GATTACAGGTACATTTGATGTTATATGATGGATAAGTGAAAAGTTTTTAAAG GAGATTTTATACCTTTTCACATTAAAAAAGGTATTTATATTATTACTTTGTAG TGATTGTCTTAAGAAAAAATATAGCCCAAATGTATAGTAAAATCAGCAGCTC AAGAAGAATTTCTGCTTCTCTTTGTAGTTGATGCTTTGTTTTTTCCTGCAGT CAGAAATTCCTTGTATTTGTCAAATGTATAATCAGCTTGTATTGTTTTTAAAT TAAAAAAAAATTTGAATAATTAACTTTTGCCATGGGACAAGATACAAAAGTA ATTTCATATAAAGGGCCTCTCCCACCCCTGTTCTCTGGCTCCTGGCTCCTG TTTGACAAGTTACTGTTACCACTTCGCCTTATACTTTTGAGAAAGAGTCTGT GCCTAAACAAACACGTGTAACACAAATAGTAACTATACATGGAGGTCTAGC CCTCGCCTTTTTTTTTTCTTTTTTTCTTTTTTAATGGAGATCATTCTATACCA GCATGTAAGTAGCAAGGAACCTCATTCTTTTTTTGGCTGCCTAAAATTTTTT TGAATAGATATAACATAATTGATTTAATCTGCTACTGGTGAATGCTTAGGTT GTTCTTTTGCTATTACAGTGATAACTTCAATCCTAATGTTATTAAGCATATCG ATTCAGGGTATAGCTATAAGATGAAGTCCTAAAAGTATAATTTAGACTAAAT ACAAATACCCATTTCGCTAGCTGTTTTGTTTCAGAGGACTTGTTGAGCAGC TTCACTAATAATGCCATTTTTGAAGACATGGCAGGTTCAGAATCAATAAACT GGAAGAATTGTTCAGAGCATCTTTTTTCAGACAGTGATGACATTGATTCTGT ATATGATAAAGTGATTCTGCTTCTCTTTGACAACTTGCATCTCTCCTACATG GAAGTAAGTTTTATTCCTGTCAATGTTGTCTTTGTGTGTGACAGATTAGGAT TAAATTATGGTTTGACTTTTCCTAGCAGCGTGATCATGGGCAAGTGGCTTT TTTTTTTTTTTTTTTGAGACAGAGTCTCACTCTGCTGCCCAGGCTGGAGT GCAGTGGCACAGTCTTGGCTCACTGCAACTCCTGCCTCCGGTCCAAGTG ATTCTCGTGCTGCAGCTTCTCAAGTAGCTGGCATCACCACCACACCTGGCT AATTTTTGTATTTTAGTAACGACGAGGTTTCACCATGTTGGCAAAGCTGGT CTCAAATTCCTGGCCTCAAGTGATCTGCCCACTTCAGCCTCCCAAAGTGTT GGGATTACAGGCGTGAGCCACTGCGCCCAGCTTTTTAAACTTTTAGATTC ATTTAATAGGTAAATTGCATGTCACGGGTTTGTAGCTTATTCTTTCAGAAAC TCTTGCATTATCTGTAGACGTGGACGTAAATATCCACCTCATAGGGTTTTCA TAAAAAATAATTGAGATAATGTATGTAATGTTTCACAGTGCTTTGCAGACTA TCTAATAAATAGTAGCTATTAGTA. In some embodiments, the isolated polynucleotide or nucleic acid sequence comprises a coding region (or CDS) of a human Sghrt RNA sequence. In various embodiments, the CDS comprises the sequence set forth in SEQ ID NO: 15: ATGCTCCAGTTCCTGCTTGGATTTACA CTGGGCAACGTGGTTGGAATGTATCTGGCTCAGAACTATGATATACCAAAC CTGGCTAAAAAACTTGAAGAAATTAAAAAGGACTTGGATGCCAAGAAGAAA CCCCCTAGTGCATGA. In some embodiments, the isolated polynucleotide or nucleic acid sequence comprises a 5' untranslated region (5'UTR) of a human Sghrt RNA sequence. In various embodiments, the 5'UTR of the human Sghrt RNA sequence comprises the sequence set forth in SEQ ID NO: 16: GACCGG CCCGCGGAGCTGCTGCAGTCCTTCGCGCCCTCCTCGCCCTCCCACCGA CATC. In some embodiments, the isolated polynucleotide or nucleic acid sequence comprises a 3' untranslated region (3'UTR) of a human Sghrt RNA sequence. In various embodiments, the 3'UTR of the human Sghrt RNA sequence comprises the sequence set forth in SEQ ID NO:17: GACTGCCTCCAGCACTGCCTTCAGGATATACTGATTCTACTGCTCTTGAGG GCCTCGTT- TACTATCTGAAC-
CAAAAGCTTTTGTTTTCGTCTCCAGCCTCAG
CACTTCTCTTCTTTGCTA-
GACCCTGTGTTTTTGCTTTAAAGCAAGCAAAAT
GGGGCCCCAATTTGAGAACTACCCGACATTTCCAA-
CATACTCACCTCTTCC CATAATCCCTTTCCAACTG-
CATGGGAGGTTCTAAGACTGGAATTATGGTGC
TAGATTAGTAAACATGACTTTTAAT-
GAGTAGTGTCTTCTTTATCGTTTGCGA TTTTTAC-
TACCTTTTTTCAAAAGAAAAATTGAT-
GAGTTTTGTATAGCTGGTCA
GATACAAATAATAGTGACTTCACAGTTTAGTAAT-
TATAATGGGTACTTGTTA AACATTTGGTACTAAAT-
TATGTTGCTGCAAAGTAATTAAAATTAGTATCTAG
AGCTAGTTTCTGGTGAATTATTCATTTAT-
TTTGTACTGTTGTTAGGCAGCTC TGTAGTTGCTAAT-
TTAACCAATAAGTCAATTTGCTATTCAT-
GAAGAAACGAT
TCTGAGAATCCTGTCAGGAATTGGGGAAT-
GAAAAAATACACAAAATAATGG
TCTTTGTCCCAGTAGAGTTCATAGTCTATT-
TAGTGTGCATGTTTTTCCTTAA TGATGTATTT-
GATCTGACTTTTTTCCTTCTCAAAAGAATCAT-
ACTTGGGATTA
CAGGTACATTTGATGTTATATGATGGATAAGT-
GAAAAGTTTTTAAAGGAGAT TTTATACCTTTTCA-
CATTAAAAAAGGTATTTATATTATTACTTTGTAGT-
GATT
GTCTTAAGAAAAAATATAGCC-
CAAATGTATAGTAAAATCAGCAGCTCAAGAA GAAT-
TTCTGCTTCTCTTTGTAGTT-
GATGCTTTGTTTTTCCTGCAGTCAGAA
ATTCCTTGTATTTGTCAAATGTATAATCAGCTTGTAT-
TGTTTTAAATTAAAA AAAAATTTGAATAAT-
TAACTTTTGCCATGGGACAAGATACAAAAGTAAT-
TTC
ATATAAAGGGCCTCTCC-
CACCCCTGTTCTCTGGCTCCTGGCTCCTGTTTGA
CAAGTTACTGTTACCACTTCGCCTTATACTTTT-
GAGAAAGAGTCTGTGCCTA
AACAAACACGTGTAACACAAATAGTAACTATA-
CATGGAGGTCTAGCCCTCG
CCTTTTTTTTTTCTTTTTTTCTTTTTTAATGGAGAT-
CATTCTATACCAGCATGT AAGTAGCAAGGAACCT-
CATTCTTTTTTTGGCTGCCTAAAATTTTTTTGAATA
GATATAACATAATTGATTTAATCTGCTACTGGT-
GAATGCTTAGGTTGTTCTT TTGCTATTACAGTGA-
TAACTTCAATCCTAATGTTATTAAGCATATCGATTCA
GGGTATAGCTATAAGATGAAGTCCTAAAAGTATAAT-
TTAGACTAAATACAAA TACCCAT-
TTCGCTAGCTGTTTTGTTTCAGAGGACTTGTT-
GAGCAGCTTCAC
TAATAATGCCATTTTTGAAGA-
CATGGCAGGTTCAGAATCAATAAACTGGAA GAAT-
TGTTCAGAGCATCTTTTTTCAGACAGTGATGACAT-
TGATTCTGTATAT
GATAAAGTGATTCTGCTTCTCTTTGACAACTTG-
CATCTCTCCTACATGGAAG TAAGTTTTATTCCTGT-
CAATGTTGTCTTTGTGTGTGACAGATTAGGATTAAA
TTATGGTTTGACTTTTCCTAGCAGCGTGAT-
CATGGGCAAGTGGCTTTTTTT TTTTTTTTTTTGA-
GACAGAGTCTCACTCTGCTGCCCAGGCTG-
GAGTGCAG
TGGCACAGTCTTGGCT-
CACTGCAACTCCTGCCTCCCGGTCCAAGTGATTC
TCGTGCTGCAGCTTCTCAAGTAGCTGGCATCAC-
CACCACACCTGGCTAATT TTTGTATTTT-
TAGTAACGACGAGGTTTCAC-
CATGTTGGCAAAGCTGGTCTC
AAATTCCTGGCCTCAAGTGATCTGCC-
CACTTCAGCCTCCCAAAGTGTTGGG ATTA-
CAGGCGTGAGCCACTGCGCCCAGCTTTTT-
TAAACTTTTAGATTCATTT
AATAGGTAAATTGCATGTCACGGGTTTGTAGCTTAT-
TCTTTCAGAAACTCTT GCATTATCTGTA-
GACGTGGACGTAAATATCCACCTCATAGGGTTTT-
CATAA
AAAATAATTGAGATAATGTATGTAATGTTT-
CACAGTGCTTTGCAGACTATCT AATAAATAGTAGC-
TATTAGTA.

In various embodiments, the polypeptide comprises a human Sghrt secreted peptide or a part/fragment thereof. In various embodiments, the human Sghrt secreted peptide comprises the sequence set forth in SEQ ID NO: 18: MLQFLLGFTLGNVVGMYLA or SEQ ID NO: 22: MLQFLLGFTLGNVVGMY or portions, optionally linear portions, thereof.

In various embodiments, the polypeptide, the polynucleotide or the nucleic acid sequence or a part/fragment thereof shares at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or at least about 100% sequence identity with the sequences indicated in Table 1 below, or portions, optionally linear portions, thereof.

TABLE 1

| SEQ ID NO | |
|---|---|
| 1 | Human Sghrt peptide sequence/*Homo sapien* Sghrt peptide sequence/Chimpanzee Sghrt peptide sequence/*Pan troglodytes* Sghrt peptide sequence/Bonobo Sghrt peptide sequence/*Pan paniscus* Sghrt peptide sequence |
| 2 | Pig Sghrt peptide sequence/*Sus scrofa* Sghrt peptide sequence |
| 3 | Cow Sghrt peptide sequence/*Bos taurus* Sghrt peptide sequence |
| 4 | Rat Sghrt peptide sequence/*Rattus norvegiscus* peptide sequence |
| 5 | Mouse Sghrt peptide sequence/*Mus musculus* peptide sequence |
| 6 | Chicken Sghrt peptide sequence/*Gallus gallus* peptide sequence |
| 7 | Zebrafish Sghrt peptide sequence/*Danio rerio* peptide sequence |
| 8 | Mouse Sghrt RNA (ENSMUST00000152147) |
| 9 | Mouse Sghrt RNA sequence (ENSMUST00000136110) |

TABLE 1-continued

| SEQ ID NO | |
|---|---|
| 10 | Mouse Sghrt RNA sequence (ENSMUST00000130875) |
| 11 | Mouse Sghrt DNA sequence |
| 12 | Human Sghrt DNA sequence |
| 13 | Human Sghrt RNA sequence |
| 14 | Human Sghrt RNA sequence (5'UTR-CDS-3'UTR) |
| 15 | Human Sghrt RNA sequence (CDS only) |
| 16 | Human Sghrt RNA sequence (5'UTR only) |
| 17 | Human Sghrt RNA sequence (3'UTR only) |
| 18 | Human Sghrt peptide sequence 2 |
| 19 | Shared Sghrt peptide sequence 1: MXQFXLGFTXGNVVGMYLAQNYXXPNXXKKXEXXKKD XXAKKKPPX |
| 20 | Shared Sghrt peptide sequence 2: GNVVGMYLAQNY |
| 21 | Shared Sghrt peptide sequence 3: AKKKPP |
| 22 | Human Sghrt peptide sequence 3: MLQFLLGFTLGNVVGMY |
| 23 | Predicted C-terminal product: QNYDIPNLAKKLEEIKKDLDAKKKPPSA |
| 24 | Predicted antigenic residue 1: DIP |
| 25 | Predicted antigenic residue 2: KDLDAKKKPPSA |

In various embodiments, the size/molecular weight/molecular mass of the polypeptide or a part/fragment thereof is from about 1 KDa to about 30 KDa, from about 5 KDa to about 20 KDa, from about 5 KDa to about 15 KDa, from about 5 KDa to about 12 KDa or from about 15 KDa to about 20 KDa. In some embodiments, the size/molecular weight/ molecular mass of the polypeptide is from about 5 KDa to about 6 KDa, or about 5 kDa, about 5.8 KDa or about 6 KDa. In some embodiments, the size/molecular weight/molecular mass of the polypeptide in its monomeric form is from about 5 KDa to about 6 KDa, or about 5 KDa, about 5.8 KDa or about 6 KDa. In some embodiments, the size/molecular weight/molecular mass of the polypeptide or a part/fragment thereof is from about 7 KDa to about 9 KDa, or about 7 KDa, about 8 KDa or about 9 KDa. In some embodiments, the size/molecular weight/molecular mass of the polypeptide in its dimeric form is from about 7 KDa to about 9 KDa, or about 7 KDa, about 8 KDa or about 9 KDa. In some embodiments, the size/molecular weight/molecular mass of the polypeptide or a part/fragment thereof is from about 11 KDa to about 13 KDa, or about 11 KDa, about 12 KDa or about 13 KDa. In some embodiments, the size/molecular weight/molecular mass of the polypeptide in its trimeric form is from about 11 KDa to about 13 KDa, or about 11 KDa, about 12 KDa or about 13 KDa. In some embodiments, the size/molecular weight/molecular mass of the polypeptide or polypeptide oligomer or a part/fragment thereof is about 15 KDa, about 16 KDa, about 17 KDa, about 18 KDa, about 19 KDa or about 20 KDa.

In some embodiments, the polypeptide or the polypeptide in its monomeric form or a part/fragment thereof has a size/molecular weight/molecular mass of no more than about 6000 Da. In some embodiments, the polypeptide or the polypeptide in its monomeric form or a part/fragment thereof has a size/molecular weight/molecular mass of from about 5000 Da to about 6000 Da or from about 5200 Da to about 5600 Da. In various embodiments, the polypeptide or the polypeptide in its monomeric form or a part/fragment thereof has a size/molecular weight/molecular mass of about 5240 Da, about 5250 Da, about 5260 Da, about 5270 Da, about 5280 Da, about 5290 Da, about 5300 Da, about 5310 Da, about 5320 Da, about 5380 Da, about 5390 Da, about 5400 Da, about 5520 Da, about 5530 Da, about 5265 Da, about 5267 Da, about 5283 Da, about 5313 Da, about 5246 Da, about 5264.87 Da, about 5266.85 Da, about 5282.83 Da, about 5312.84 Da, about 5399.85 Da, about 5529.94 Da or about 5245.78 Da.

In some examples, the polypeptide (or a part/fragment thereof) acts as a ligand or a signaling molecule. In some examples, the polypeptide (or a part/fragment thereof) exerts its biological functions by engaging with and/or modulating one or more regulatory proteins, including but not limited to those larger than itself. In some examples, the polypeptide (or a part/fragment thereof) interacts with or binds to subunit 9 of mitochondrial respiratory complex III.

In some examples, the polypeptide (or a part/fragment thereof) and/or its RNA transcript is implicated in or capable of regulating cell division, cell proliferation and/or cell dedifferentiation of a heart cell.

In some examples, ATG-mutated embryonic stem (ES) cell clones generated using CRISPR gene editing technique, which disrupts the formation of the polypeptide while still keeping its RNA transcript, fails to use fatty acid to generate adenosine triphosphate (ATP). In some examples therefore, the polypeptide (or a part/fragment thereof) allows for fatty acid utilization in a heart cell. In some examples, this capability is not demonstrated by the RNA transcript of the polypeptide.

Mouse cardiomyocytes (CMs) exit cell cycle at the end of the proliferation window at approximately the seventh postnatal day (P7). In some examples, expression of the polypeptide (or a part/fragment thereof) and/or its RNA transcript transiently spikes at P7 and increases progressively from P10 onwards with age in mouse hearts, indicating its potential role at regulating CM cell cycle exit during this stage of development.

In some examples, the polypeptide (or a part/fragment thereof) and/or its RNA transcript regulates cell proliferation by regulating cell cycle re-entry. In some examples, the polypeptide (or a part/fragment thereof) and/or its RNA transcript regulates cell cycle re-entry by regulating cell-cycle checkpoints regulators. In some examples, the polypeptide (or a part/fragment thereof) and/or its RNA transcript regulates one or more of the following cell-cycle checkpoints regulators: activators, inhibitors, G1/S and/or G2/M phase regulators.

In some examples, the polypeptide (or a part/fragment thereof) and/or its RNA transcript regulates one or more of the following G1/S phase regulators: Cdk4, Cdk6, Ccne1 and Ccnd2. In some examples, the polypeptide (or a part/fragment thereof) and/or its RNA transcript regulates one or more of the following G1/S phase regulators: Cdk6 and Ccnd2. In some examples, the polypeptide (or a part/fragment thereof) and/or its RNA transcript regulates one or more of the following G2/M phase regulators: Ccng1, Cdk1 and Cdc25a.

In some examples, the polypeptide (or a part/fragment thereof) and/or its RNA transcript regulates cyclin-dependent kinase inhibitor 1 (p21), which is a G1/S and G2/M phase cell cycle inhibitor. In some examples, the polypeptide (or a part/fragment thereof) and/or its RNA transcript regulates p21 through regulating upstream Calreticulin (CALR). In some examples, the polypeptide (or a part/fragment thereof) and/or its RNA transcript regulates CALR to regulate cell cycle re-entry.

In some examples, a reduced/abolished expression, or inhibition of the polypeptide (or a part/fragment thereof) and/or its RNA transcript downregulates Ccnd2. In some examples, a reduced/abolished expression, or inhibition of the polypeptide (or a part/fragment thereof) and/or its RNA transcript upregulates Ccng1. In some examples, a reduced/abolished expression, or inhibition of the polypeptide (or a part/fragment thereof) and/or its RNA transcript does not significantly change the expression of Nppa and/or Dstn.

In some examples, a reduced/abolished expression, or inhibition of the polypeptide (or a part/fragment thereof) and/or its RNA transcript upregulates the G1/S phase activator Cdk6. In some examples, a reduced/abolished expression, or inhibition of the polypeptide (or a part/fragment thereof) and/or its RNA transcript upregulates the G2/M phase activators Cdk1 and Cdc25a. In some examples, a reduced/abolished expression, or inhibition of the polypeptide (or a part/fragment thereof) and/or its RNA transcript induces or promotes S phase entry. In some examples, a reduced/abolished expression, or inhibition of the polypeptide (or a part/fragment thereof) and/or its RNA transcript induces or promotes M phase entry. In some examples, a reduced/abolished expression, or inhibition of the polypeptide (or a part/fragment thereof) and/or its RNA transcript significantly increases Aurora B which is a marker for cytokinesis. In some examples, a reduced/abolished expression, or inhibition of the polypeptide (or a part/fragment thereof) and/or its RNA transcript induces or promotes cytokinesis.

In some examples, a reduced/abolished expression, or inhibition of the polypeptide (or a part/fragment thereof) and/or its RNA transcript downregulates the G1/S and G2/M phase inhibitor p21 and/or upregulates CALR. In some examples, a reduced/abolished expression, or inhibition of the polypeptide (or a part/fragment thereof) and/or its RNA transcript upregulates CALR which blocks p21 translation. In some examples, the effects of a reduced/abolished expression, or inhibition of the polypeptide (or a part/fragment thereof) and/or its RNA transcript is not recapitulated by loss of p21 alone.

In some examples, a reduced/abolished expression, or inhibition of the polypeptide (or a part/fragment thereof) and/or its RNA transcript decreases a cross-sectional area of a cell e.g. a CM cell or decreases a cell size.

Thus, in various examples, a reduced/abolished expression, or inhibition of the polypeptide (or a part/fragment thereof) and/or its RNA transcript induces or promotes cell cycle re-entry in vitro and in vivo.

In some examples, a reduced/abolished expression, or inhibition of the polypeptide (or a part/fragment thereof) and/or its RNA transcript does not significantly change the levels of one or more of the following G1/S phase activators: Ccne2, Ccnd1 and Cdk2. In some examples, a reduced/abolished expression, or inhibition of the polypeptide (or a part/fragment thereof) and/or its RNA transcript does not significantly change the levels of one or more of the following G2/M phase activators: Ccnb1 and Cdc25b. In some examples, a reduced/abolished expression, or inhibition of the polypeptide (or a part/fragment thereof) and/or its RNA transcript does not significantly increase or induce apoptosis or cell death.

In some examples, a reduced/abolished expression, or inhibition of the polypeptide (or a part/fragment thereof) and/or its RNA transcript increases the expression of a dedifferentiation marker such as DAB2. In some examples, a reduced/abolished expression, or inhibition of the polypeptide (or a part/fragment thereof) and/or its RNA transcript results in a dedifferentiated profile such as a DAB2+ profile.

In various examples, a reduced/abolished expression, or inhibition of the polypeptide (or a part/fragment thereof) and/or its RNA transcript, e.g. in a heart cell, leads to the heart cell acquiring cardiac progenitor-like characteristics (e.g. cell appears rounder, smaller, and/or with higher nucleus/cytoplasm ratio compared to a wild-type cardiomyocyte, and/or cell shows increased DAB2+ profile and/or there is a loss of tissue structure).

Thus, in various examples, a reduced/abolished expression, or inhibition of the polypeptide (or a part/fragment thereof) and/or its RNA transcript, e.g. in a heart cell, induces or promotes dedifferentiation e.g. of the heart cell.

In some examples, the polypeptide (or a part/fragment thereof) and/or its RNA transcript is upregulated in a Transverse Aortic Constriction (TAC) stress mouse model. In some examples, the polypeptide (or a part/fragment thereof) and/or its RNA transcript is upregulated in diseased hearts such as those of end-stage heart failure patients suffering from dilated cardiomyopathy, hypertrophic cardiomyopathy and/or ischaemic cardiomyopathy.

In some examples, a reduced/abolished expression, or inhibition of the polypeptide (or a part/fragment thereof) and/or its RNA transcript results in a partial and significant rescue of ejection fraction (EF %) and left ventricular (LV) wall thickness in a TAC stress mouse model. In some examples, a reduced/abolished expression, or inhibition of the polypeptide (or a part/fragment thereof) and/or its RNA transcript in a TAC stress mouse model induces dedifferentiation of heart cells. In some examples, a reduced/abolished expression, or inhibition of the polypeptide (or a part/fragment thereof) and/or its RNA transcript in a TAC stress mouse model leads to more DAB2+ cardiomyocytes (which may be smaller and predominantly mononucleated as compared to DAB2- cardiomyocytes) per heart section as compared to a control mouse.

Accordingly, it may be desirable to manipulate the polypeptide (or a part/fragment thereof) to disrupt or inhibit its native functions to achieve heart cell proliferation or dedifferentiation. For example, one or more mutations may be introduced in the polypeptide (or a part/fragment thereof) to partially or wholly inactivate its native functions. For example, one or more of a loss-of-function mutation, a null mutation, an inactivating mutation, a recessive mutation and a dominant negative mutation may be introduced in the polypeptide (or a part/fragment thereof). In various embodiments therefore, there is provided the polypeptide (or a part/fragment thereof) as described herein comprising one or more mutation(s).

Further, the native biological effects exerted by the polypeptide (or a part/fragment thereof) may also be blocked or inhibited through use of an agent. In various embodiments, there is provided an agent that is capable of interacting with the polypeptide (or a part/fragment thereof); capable of interfering with or blocking an interaction of the polypeptide (or a part/fragment thereof) with biomolecule(s) such as a cell-cycle checkpoints regulator(s) and/or CALR; capable of interfering with or blocking an oligomerisation of the polypeptide (or a part/fragment thereof); capable of inhibiting/blocking a translation of a RNA to produce the polypeptide (or a part/fragment thereof); and/or capable of interacting with or inhibiting a polynucleotide encoding for the polypeptide (or a part/fragment thereof); so to regulate cell division, cell proliferation and/or cell dedifferentiation of a heart cell. In various embodiments, said interacting with the polypeptide (or a part/fragment thereof) comprises binding at least partially to the polypeptide (or a part/fragment thereof) and/or at least partially cleaving/degrading/digesting/hydrolyzing the polypeptide (or a part/fragment thereof) such that the polypeptide (or a part/fragment thereof) no longer has biological activity or has reduced biological activity.

In various embodiments, the agent comprises an inhibitor targeted at the polypeptide (or a part/fragment thereof). In various embodiments, there is provided an inhibitor of the polypeptide (or a part/fragment thereof). In various embodiments, the agent or the inhibitor comprises a pharmaceutically effective compound, a drug, a small molecule, a nanoparticle, a peptide, a peptide corresponding substantially to the polypeptide (or a part/fragment thereof) and further comprising mutation(s), a protein, a protease, a nucleic acid, an antibody and fragments e.g. an antigen-binding fragment and combinations thereof.

Methods of identifying an agent or inhibitor having the desired biological activity are known to the skilled person. For example, screening or high-throughout screening of compound libraries may be employed to identify lead compounds that display desirable biological activity e.g. binding affinity for the polypeptide (or a part/fragment thereof) and/or inhibitory/antagonistic activity against the polypeptide (or a part/fragment thereof). Cell-based screening or cell-based assays, e.g. using a heart cell or human ES-derived CMs or Engineering Heart Tissue (EHT) system, may be used. Multicellular, co-culture, 3D spheroid, or more specifically heart tissue and heart organoid may also be used as platforms for drug discovery. Other routine techniques such as rational design, substrate or ligand modelling and fragment screening may also be employed in combination, or independently. Antibodies may also be generated by immunizing animals with the polypeptide (or a part/fragment thereof) and engineering the antibodies so obtained to prevent an unintended immune response in the subject e.g. a human subject through strategies such as chimerization or replacement of the constant regions of the animal antibodies with those of a human antibody etc.

In various embodiments, the agent or inhibitor is capable of penetrating, translocating to or being taken up by a mitochondria, optionally wherein the agent or inhibitor is capable of selectively penetrating, translocating to or being taken up by a mitochondria, further optionally wherein the agent or inhibitor comprises a mitochondrial targeting signal, optionally a mitochondrial membrane targeting signal. In various embodiments, the agent or inhibitor is coupled/conjugated to a carrier capable of penetrating, translocating to or being taken up by a mitochondria, optionally wherein the carrier is capable of selectively penetrating, translocating to or being taken up by a mitochondria. For example, carriers that may penetrate the mitochondria include short peptide sequences with alternating cationic and hydrophobic residues, oligomeric carbohydrate scaffold, vesicle-based transporter system, cationic liposome etc.

In various embodiments, there is provided the agent or the inhibitor for use in therapy. In various embodiments, there is provided the agent or the inhibitor for use in treating impaired heart function. In various embodiments, there is provided use of the agent or the inhibitor or its pharmaceutically acceptable salt/derivatives thereof in the manufacture of a medicament for the treatment of impaired heart function.

In various embodiments, there is provided a composition, optionally a pharmaceutical composition, comprising the inhibitor or the agent and a suitable carrier, adjuvant, diluent and/or excipient.

In various embodiments, the agent, the inhibitor or the composition is capable of at least partially rescuing or improving heart function. In various embodiments, the agent, the inhibitor or the composition is capable of at least partially reducing or improving heart function after onset of hypertrophy. In various embodiments, said rescuing or improving heart function comprises at least partially rescuing or improving one or more of the following selected from the group consisting of: ejection fraction, left ventricle wall thickness, right ventricle wall thickness, left ventricular wall stress, right ventricular wall stress, ventricular mass, contractile function, cardiac hypertrophy, end diastolic volume, end systolic volume, cardiac output, cardiac index, pulmonary capillary wedge pressure and pulmonary artery pressure. In various embodiments, the agent, the inhibitor or the composition is capable of stimulating cardiomyocyte repair. In various embodiments, the agent, the inhibitor or the composition is capable of stimulating cardiac regeneration and/or proliferation.

In various embodiments, there is provided the agent, the inhibitor or the composition for use as a cardiac regenerative agent, a cardiac proliferative agent and/or a cardiac protective agent.

In various embodiments, the agent, the inhibitor or the composition is capable of inducing proliferation of heart cell in the subject. In various embodiments, the agent, the inhibitor or the composition is capable of inducing dedifferentiation of heart cell in the subject.

In various embodiments, the agent, the inhibitor or the composition comprises a first agent, inhibitor or composition targeted at the polypeptide (or a part/fragment thereof) and a second agent, inhibitor or composition targeted at the polynucleotide encoding for the polypeptide (or a part/fragment thereof).

In various embodiments, there is provided a method of treating impaired heart function in a subject, the method comprising: administering the agent, the inhibitor or the composition to the subject. In various embodiments, there is provided a method of treating impaired heart function in a subject, the method comprising: inhibiting the polypeptide (or a part/fragment thereof) in the subject.

In various embodiments, there is provided a method of treating or preventing a heart disorder or impaired heart function in a subject in need thereof, the method comprising reducing/suppressing/blocking/inhibiting/downregulating/modulating an expression of the polypeptide (or a part/fragment thereof) or an expression of a biomolecule downstream or upstream of the polypeptide (or a part/fragment thereof). In various embodiments, there is provided a method of treating or preventing a heart disorder or impaired heart function in a subject in need thereof, the method comprising administering to said subject a therapeutically effective amount of an agent or an inhibitor that is capable of binding to or interacting with the polypeptide (or a part/fragment thereof) to reduce/suppress/block/inhibit/downregulate/modulate an expression of the polypeptide (or a part/fragment thereof) or an expression of a biomolecule downstream or upstream of the polypeptide (or a part/ fragment thereof). In various embodiments, there is provided a method of treating or preventing a heart disorder or impaired heart function in a subject in need thereof, the method comprising reducing/suppressing/blocking/inhibiting an oligomerisation of the polypeptide (or a part/fragment thereof). In some embodiments, reducing/suppressing/blocking/inhibiting/downregulating/modulating an expression (e.g. a functional expression) of the polypeptide (or a part/fragment thereof) comprises reducing/suppressing/blocking/inhibiting an oligomerisation of the polypeptide (or a part/fragment thereof).

In various embodiments, the heart disorder or the impaired heart function is selected from the group consisting of: myocardial infarction, heart failure, coronary artery disease, narrowing of the arteries, heart attack, abnormal heart rhythms, arrhythmias, heart failure, heart valve disease, congenital heart disease, heart muscle disease, cardiomyopathy (including dilated cardiomyopathy, hypertrophic cardiomyopathy, ischaemic cardiomyopathy and idiopathic cardiomyopathy), pericardial disease, aorta disease, marfan syndrome, genetic cardiomyopathy, non-genetic cardiomyopathy, heart hypertrophy, pressure overload-induced heart dysfunction, and damaged heart tissue.

In various embodiments, there is provided a method of assessing heart function in a subject, the method comprising: determining an expression level of the polypeptide (or a part/fragment thereof) in a sample obtained from the subject; comparing the expression level to a reference expression level, wherein if the expression level deviates from or exceeds the reference expression level, the subject is considered to have impaired or deteriorated heart function. In some embodiments, if the expression level in the sample deviates from or exceeds the reference expression level, it is indicative of a heart disorder/impaired heart function or a predisposition to develop a heart disorder/impaired heart function in the subject.

In some embodiments, the reference expression level comprises an expression level of the polypeptide (or a part/fragment thereof) in a healthy population. For example, the reference expression level may be the average expression level/range of the polypeptide (or a part/fragment thereof) in a healthy population. In some embodiments, the reference expression level comprises an expression level of the polypeptide (or a part/fragment thereof) in an earlier sample obtained from the subject.

In various embodiments, there is provided a method of monitoring heart function in a subject, the method comprising: determining a first expression level of the polypeptide (or a part/fragment thereof) in a first sample obtained from the subject at a first time point; determining a second expression level of the polypeptide (or a part/fragment thereof) in a second sample obtained from the subject at a second time point occurring after the first time point; and comparing the first expression level with the second expression level, wherein if the second expression level is higher than the first expression level, then the heart function is considered to have deteriorated in the subject, wherein if the second expression level is lower than the first expression level, then the heart function is considered to have improved in the subject, and wherein if the second expression level is substantially the same as the first expression level, then the heart function is considered to have stabilised in the subject. In some embodiments, if the second expression level is lower than the first expression level, it is indicative of a favourable prognosis of the subject.

In various embodiments, determining an expression level of the polypeptide (or a part/fragment thereof) comprises assaying for the concentration and/or functional activity of said polypeptide (or a part/fragment thereof), including use of a competitive binding assay for said polypeptide (or a part/fragment thereof).

In various embodiments, determining an expression level of the polypeptide (or a part/fragment thereof) comprises contacting the sample with a reagent specific to the polypeptide for ascertaining or measuring quantitatively, semi-quantitatively or qualitatively the amount of polypeptide (or a part/fragment thereof). The agent may be capable of detecting and/or binding directly or indirectly to the polypeptide (or a part/fragment thereof). Examples of reagents include but are not limited to proteins/probes (for example antigen binding proteins such as antibodies or fragments thereof, enzymes such as horseradish peroxides and alkaline phosphatase, and the like), polynucleotides (for example aptamers), and small molecules (for example metallic nanoparticles). An expression level of the polypeptide (or a part/fragment thereof) may be determined by a number of routine techniques including immunohistochemistry, ELISA, Western blot, dot blot, immunoprecipation, mass spectrometry and the like. For example, a reagent such as an antibody (e.g. a labeled antibody) that specifically binds the polypeptide (or a part/fragment thereof) may be added to the sample to permit a relative or absolute ascertaining of the amount of polypeptide (or a part/fragment thereof).

The sample may comprise a heart tissue, optionally a mitochondrion from a heart tissue. In various embodiments therefore, the method further comprises extracting a mitochondrion from a heart tissue. In various embodiments, the heart tissue comprises a left ventricular heart issue. In various embodiments, the heart tissue comprises a cardiomyocyte.

In various embodiments, the subject comprises a human subject.

In some embodiments, the method comprises a prognosis method. In some embodiments, the method comprises a diagnosis method.

In various embodiments, there is provided a prognostic or diagnostic method to assess the regenerative or proliferative capacity of heart tissue before, after or during a cardiac treatment regimen comprising: determining the presence or amount of the polypeptide (or a part/fragment thereof) in a cardiac sample of said heart tissue; and where the polypeptide (or a part/fragment thereof) is present concluding the proliferative capacity of said heart tissue is poor; and where the polypeptide (or a part/fragment thereof) is absent concluding the proliferative capacity of said heart tissue is good. In some embodiments, the determining step involves assaying for the functional activity of said polypeptide (or a part/fragment thereof), including use of a competitive binding assay for said polypeptide (or a part/fragment thereof).

In various embodiments, the method further comprises administering to the subject an inhibitor of the polypeptide (or a part/fragment thereof). In various embodiments, the method further comprises administering to the subject an agent, an inhibitor or a composition as described herein. In various embodiments, the method further comprises administering to the subject a therapeutically effective amount of the inhibitor, the agent, or the composition.

In various embodiments, there is provided a method of identifying or screening for a potential drug or therapeutic agent for treating impaired heart function or heart disorder, the method comprising: analyzing an expression level of the polypeptide (or a part/fragment thereof) in the presence and in the absence of the candidate drug or therapeutic agent; and determining if the candidate drug or therapeutic agent is a useful drug or therapeutic agent for treating or preventing an impaired heart function or heart disorder based on the differences in the expression of the polypeptide (or a part/fragment thereof) in the presence of the candidate drug or therapeutic agent and in the absence of the candidate drug or therapeutic agent.

In various embodiments, the candidate drug or therapeutic agent is identified as a useful drug or therapeutic agent for treating or preventing an impaired heart function or a heart disorder if the expression of the polypeptide (or a part/fragment thereof) is reduced in the presence of the candidate drug or therapeutic agent as compared to in the absence of the candidate drug or therapeutic agent.

In various embodiments, there is provided a method of identifying a potential drug for treating impaired heart function, the method comprising: determining a first expression level of the polypeptide (or a part/fragment thereof) in a cell; exposing the cell to a drug candidate; and determining a second expression level of the polypeptide (or a part/fragment thereof) after the exposure, wherein if the second expression level is lower than the first expression level, then the drug candidate is identified as a potential drug for treating impaired heart function.

In various embodiments, there is provided a vector comprising a polynucleotide sequence e.g. a DNA/cDNA sequence encoding for the polypeptide (or a part/fragment thereof) or the agent, the inhibitor or the composition as described herein. The vector may be selected from the group consisting of a plasmid, a viral particle, a phage, a baculovirus, a yeast plasmid, a lipid based vehicle, a polymer microsphere, a liposome, and a cell based vehicle, a colloidal gold particle, lipopolysaccharide, polypeptide (or a part/fragment thereof), polysaccharide, a viral vehicle, an adenovirus, a retrovirus, a lentivirus, an adeno-associated viruses, a herpesvirus, a vaccinia virus, a foamy virus, a cytomegalovirus, a Semliki forest virus, a poxvirus, a pseudorabies virus, an RNA virus vector, a DNA virus vector and a vector derived from a combination of a plasmid and a phage DNA. The polynucleotide may be operatively linked to an expression control sequence(s) to direct peptide synthesis. The vector may also comprise one or more selectable marker genes to provide a phenotypic trait for selection of transformed host cells.

In various embodiments, there is provided a host cell transfected with or comprising the vector.

In various embodiments, there is provided a method for producing the polypeptide (or a part/fragment thereof), the agent, the inhibitor or the composition, the method comprising: culturing the host cell under suitable conditions to permit production of the polypeptide (or a part/fragment thereof), the agent, the inhibitor or the composition; and recovering the polypeptide (or a part/fragment thereof), the agent, the inhibitor or the composition so produced.

The vector and/or the host cell may be used in a method of therapy.

In various embodiments, there is provided a transgenic non-human subject comprising a nucleic acid construct or a polynucleotide construct (e.g. DNA/cDNA sequences) encoding for the polypeptide (or a part/fragment thereof), optionally wherein the transgenic non-human subject overexpresses the polypeptide (or a part/fragment thereof). The transgenic non-human subject may comprise a non-human mammal selected from the group consisting of a non-human primate, a rodent, a mouse, a rabbit, a sheep, a cow and a pig.

In various embodiments, there is provided the polypeptide (or a part/fragment thereof) coupled to a detectable label. The polypeptide (or a part/fragment thereof) may act as a biomarker for identifying impaired heart function.

In various embodiments, there is provided a kit comprising the detectable label or the agent. The detectable label may be selected from the group consisting of fluorescent label, radioactive label, enzymatic label, chemiluminescent label, oligonucleotide, dye, colloidal particle, oxidant, reductant and combinations thereof. The kit may be a kit for assessing heart function in a subject, or for assessing whether a subject has a heart disorder or is predisposed to developing a heart disorder. The kit may further comprise instructions for use.

In various embodiments, there is provided a method for proliferation, dedifferentiation or regeneration, or promoting proliferation, dedifferentiation or regeneration of a heart cell, the method comprising contacting the heart cell with one or more of the agent, the inhibitor, the composition or the vector. In various embodiments, there is provided a method of dedifferentiating and/or proliferating a heart cell, the method comprising: inhibiting the expression of the polypeptide (or a part/fragment thereof) in the heart cell.

In various embodiments, there is provided a cell, optionally a heart cell, produced by the method, or progenies or cell derivatives thereof. In various embodiments, there is provided the heart cell, or progenies or cell derivatives thereof, for use in therapy in a subject in need thereof.

In various embodiments, the heart cell comprises a cardiomyocyte, further optionally wherein the cardiomyocyte comprises an adult cardiomyocyte.

In various embodiments, the method described herein is in vitro or in vivo.

In various embodiments, there is provided a product, a method or a use as described herein.

EXAMPLES

Figure 1:
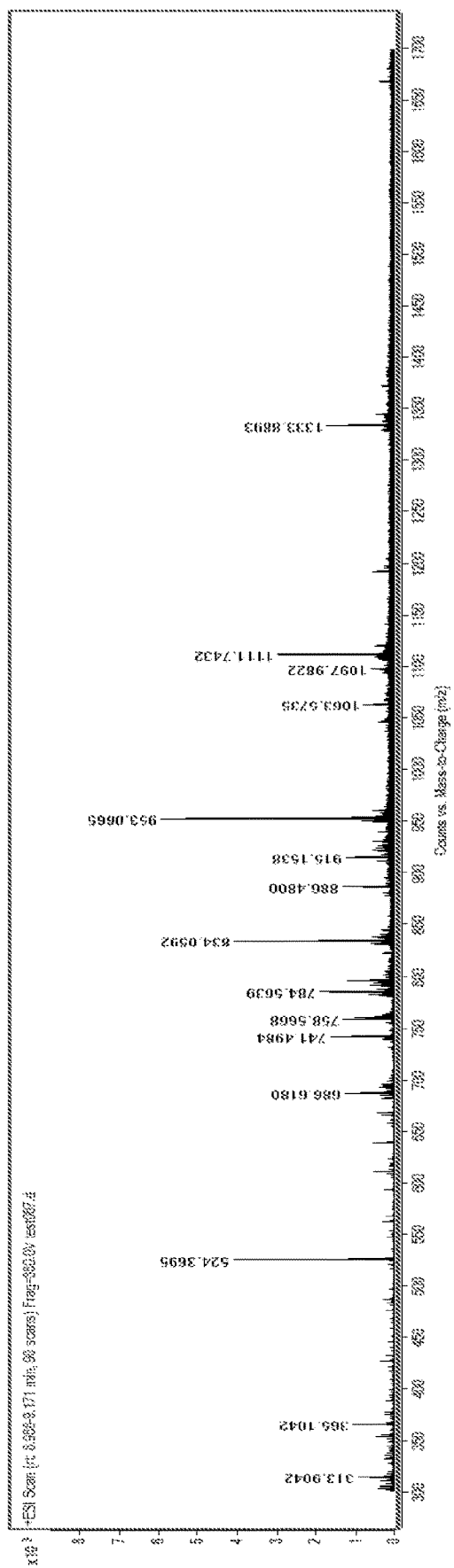
FIG. 1 is a mass spectrum result of the membrane proteins extracted from the mitochondria of a rat heart tissue.

Example embodiments of the disclosure will be better understood and readily apparent to one of ordinary skill in the art from the following discussions and if applicable, in conjunction with the figures. It should be appreciated that other modifications related to structural, electrical and optical changes may be made without deviating from the scope of the invention. Example embodiments are not necessarily mutually exclusive as some may be combined with one or more embodiments to form new exemplary embodiments.

Key Regulators of the Cardiomyocytes Dedifferentiation and Proliferation

The neonatal mammalian heart possesses a robust but transient regenerative ability that is rapidly lost after the first few days of life. The cardiac regeneration is likely due to dedifferentiation and subsequent proliferation of pre-existing CMs. Dedifferentiation of cardiomyocytes is characterized by the disassembly of sarcomeric structure, extrusion of mitochondria, electrical uncoupling and expression of regulators of cell cycle progression. Understanding the biology of CM dedifferentiation and proliferation could be of great clinical significance for treating heart failure.

Signaling pathways, transcription factors, cell cycle regulators, epigenetic modifiers, environmental factors and extracellular matrix have been identified to control mammalian CM dedifferentiation and proliferation. Manipulating these pathways reactivates CM proliferation and regenerates the injured adult mammalian hearts. In human HF, the limited functional recovery clearly demonstrates insufficient regeneration of human adult CMs. The evidence of human CM renewal suggests that the development of pharmacological strategies to stimulate this process may be a rational alternative or complement to cell transplantation strategies for CM replacement. Therefore, it is important to understand the biology and uncover novel gene regulatory pathways/drivers mediating CM dedifferentiation and proliferation in normal and failing hearts.

Long Non-Coding RNA-Derived Micropeptides in Cardiomyopathy

Long noncoding RNAs (lncRNAs) has been recently identified as a new layer of complexity to the regulation of the biological processes underlying normal cardiac development and myocardial remodeling during disease. Dysregulation in lncRNA regulatory circuits have been associated with cardiac pathological hypertrophy and heart failure. LncRNAs represent potential targets for novel therapeutic strategies for cardiovascular diseases. Interestingly, recent emerging evidence indicates that several LncRNAs have been mis-annotated as noncoding and in fact contains short open reading frames (sORFs) that encode functional peptides. sORF-encoded peptides (SEPs) or micropeptides, have been shown to have important roles in fundamental biological processes and in the maintenance of cellular homeostasis. These small proteins can act independently as ligands or signaling molecules, or they can exert their biological functions by engaging with and modulating larger regulatory proteins. Biological roles have been discovered to a small fraction of the total putative micropeptides and a huge amount of work remains to be done to prove their existence and elucidate their functions.

Single nuclear RNA-seq was previously performed on left ventricular (LV) CMs isolated from healthy and failing adult mouse and human hearts. This was followed by a mapping out of gene regulatory networks that contained key nodal lincRNAs (Sghrt and Gas5) that regulate dedifferentiation and cell cycle gene expression in CM subpopulations. This was also described in International Application No. PCT/SG2017/050620, the contents of which are fully incorporated herein by reference.

Mass spectrometry to profile small peptides in mitochondrial extract of bovine hearts identified that Sghrt is also potentially a micropeptide that has 100% homology with "Short transmembrane mitochondrial protein 1 precursor"

(STMP1) and was co-purified with subunit 9 of mitochondrial respiratory complex III. Multiple sequence alignment demonstrated that the STMP1 micropeptide sequence is also highly conserved across vertebrates. Because there is no experimental evidence yet confirming the presence of Sghrt micropeptide in human and other mammals, it was proposed to perform Mass Spectrometry analysis on mitochondrial membrane proteins isolated from mouse, rat, pig and human heart as well as human pluripotent stem cell-derived cardiomyocytes.

Identification Sghrt-Encoded Micropeptides in Mitochondria Membrane Proteins Isolated from Rat Hearts Predicted mass-to-charge ratios (m/z) of peptides of interest were generated using an online tool (http://prospector.ucsf.edu/prospector/cgi-bin/msform.cgi?form=msisotope) (see sequences in Zhang D et al., Functional prediction and physiological characterization of a novel short trans-membrane protein 1 as a subunit of mitochondrial respiratory complexes. Physiol Genomics. 2012; 44:1133-1140. doi: 10.1152/physiolgenomics.00079.2012). The m/z ratios allow for identification of the right peak of mass in a mass spectrum and consequently, the identification of the peptide sequence of that peak. The results are shown in Table 2 below.

Mitochondrial membrane proteins were extracted from rat heart tissue and subjected to liquid chromatography-mass spectrometry (LC-MS). Presence of the predicted m/z was determined by using the extracted ion chromatogram (EIC) function of Agilent Mass Hunter B08 software. The mass spectrum obtained is shown in FIG. 1. A prominent molecular feature 886.48 m/z eluting at around 9 minutes was identified.

Figure 2:
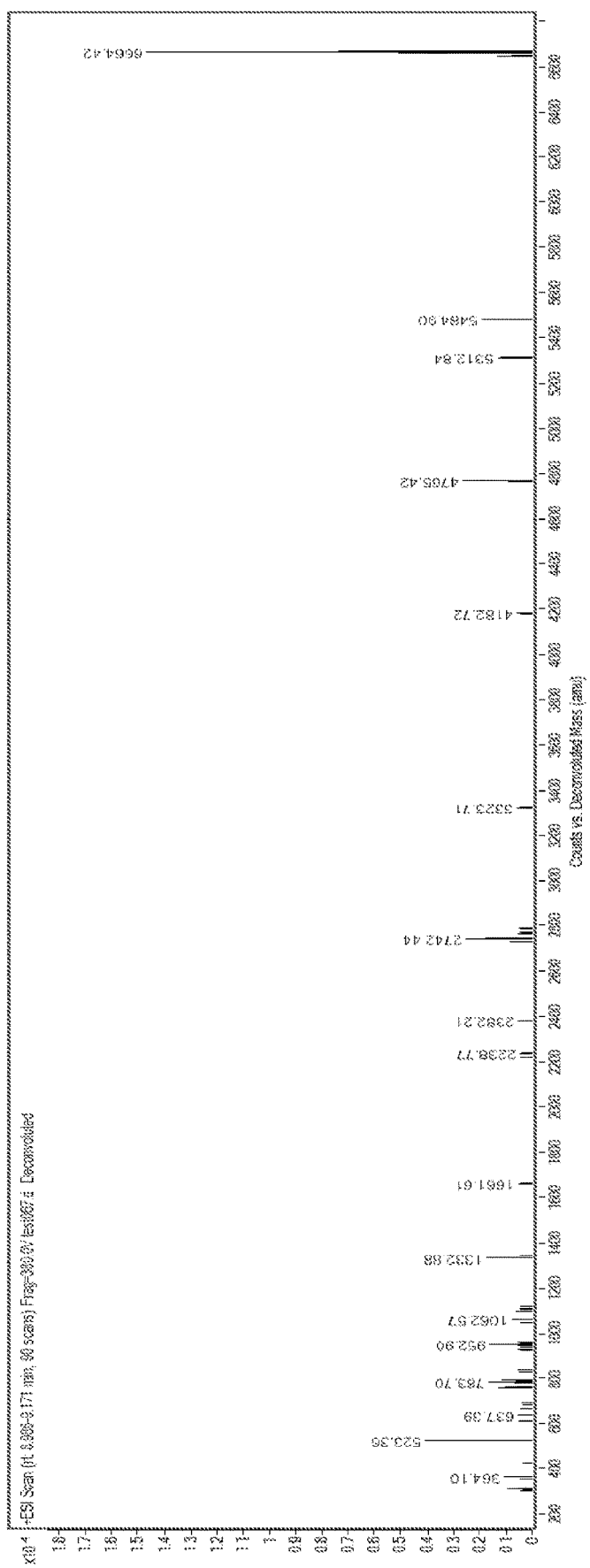
FIG. 2 is a deconvolution of the mass spectrum of FIG. 1.

The mass spectrum was then deconvoluted to obtain estimates of original molecular mass (FIG. 2). The prominent molecular feature 886.48 m/z was estimated to be of mass 5321.84, which is suggestive of the rat STMP1 peptide.

Figure 3:
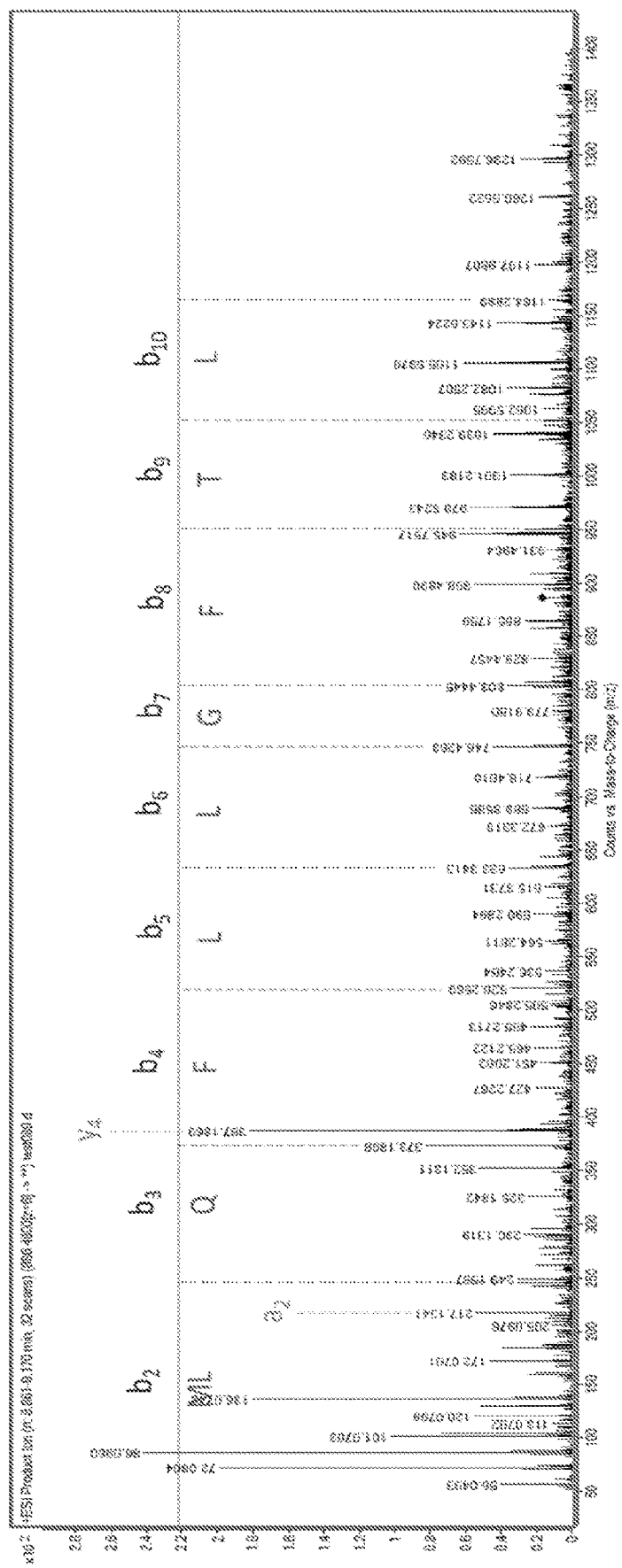
FIG. 3 is a sequencing result of the peptide, with a peak at 886.48 m/z, using tandem mass spectrometry (ms/ms).

For confirmation of peptide identity, amino acid sequencing was done using tandem mass spectrometry (ms/ms). The sample was rerun on the LC-MS, with the collision-induced dissociation (CID) cell configured to fragment the molecular feature at various fragmentation energies, and the resulting mass spectrum was collected. Amino acid sequences were then confirmed by manually matching the ms/ms spectrum to predicted a, b, and y-series ions obtained from http://prospector.ucsf.edu/prospector/cgi-bin/msform.cgi?form=msproduct (FIG. 3). Several different fragments were identified, including for example, a fragment comprising the sequence "MLQFLLGFTL (SEQ ID NO: 26)". Based on the 40 Substitute Specification-Clean identified fragments, the full sequence of Sghrt is predicted to be "MLQFLLGFTLGNVVGMYLAQNYDIPNLAKKLEEIK-KDLDAKKKPPSA (SEQ ID NO: 1)". The ms/ms spectrum is in agreement with b ions generated from the N-terminus of rat Sghrt (see predicted N-terminal amino acids of rat Sghrt in Table 2). Strong signal of a2 and y4 ions were also noted.

TABLE 2

Predicted mass and m/z of the membrane peptide SGHRT in various animal species

| Species | Predicted Sequence | Mass | M + 7 | M + 6 | M + 5 | SEQ ID NO: |
|---|---|---|---|---|---|---|
| Homo sapien (Human) | MLQFLLGFTLGNVVGMYLAQ NYDIPNLAKKLEEIKKDLDA KKKPPSA | 5264.87 | 753.13 | 878.49 | 1053.98 | 1 |
| Pan troglodytes (Chimpanzee) | Conserved | | | | | |
| Pan paniscus (Bonobo) | Conserved | | | | | |
| Sus scrofa (pig) | MLQFLLGFTLGNVVGMYLAQ NYDIPNLAKKLEDIKKDLDA KKKPPSS | 5266.85 | 753.41 | 878.82 | 1054.38 | 2 |
| Bos taurus (cow) | MLQFLLGFTLGNVVGMYLAQ NYDIPNLAKKLEEIKKDLDA KKKPPSC | 5282.83 | 755.70 | 881.48 | 1057.57 | 3 |
| Rattus norvegicus (rat) | MLQFLLGFTLGNVVGMYLAQ NYDMPNLAKKLEEIKKDLDA KKKPPSS | 5312.84 | 759.98 | 886.48 | 1063.57 | 4 |
| Mus musculus (mouse) | MLQFLLGFTWGNVVGMYLAQ NYEMPNLAKKLEEIKKDLEA KKKPPSS | 5399.85 | 772.41 | 900.98 | 1080.98 | 5 |
| Gallus gallus (chicken) | MLQFVLGFTLGNVVGMYLAQ NYDIPNIAKKLEDFKKDVEA KKKPPSDKS | 5529.94 | 791.00 | 922.66 | 1106.99 | 6 |
| Danio rerio (zebrafish) | MLQFILGFTLGNVVGMYLAQ NYEVPNISKKIEAFKKDVEA KKKPPE | 5245.78 | 750.40 | 875.30 | 1050.16 | 7 |

Figure 4:
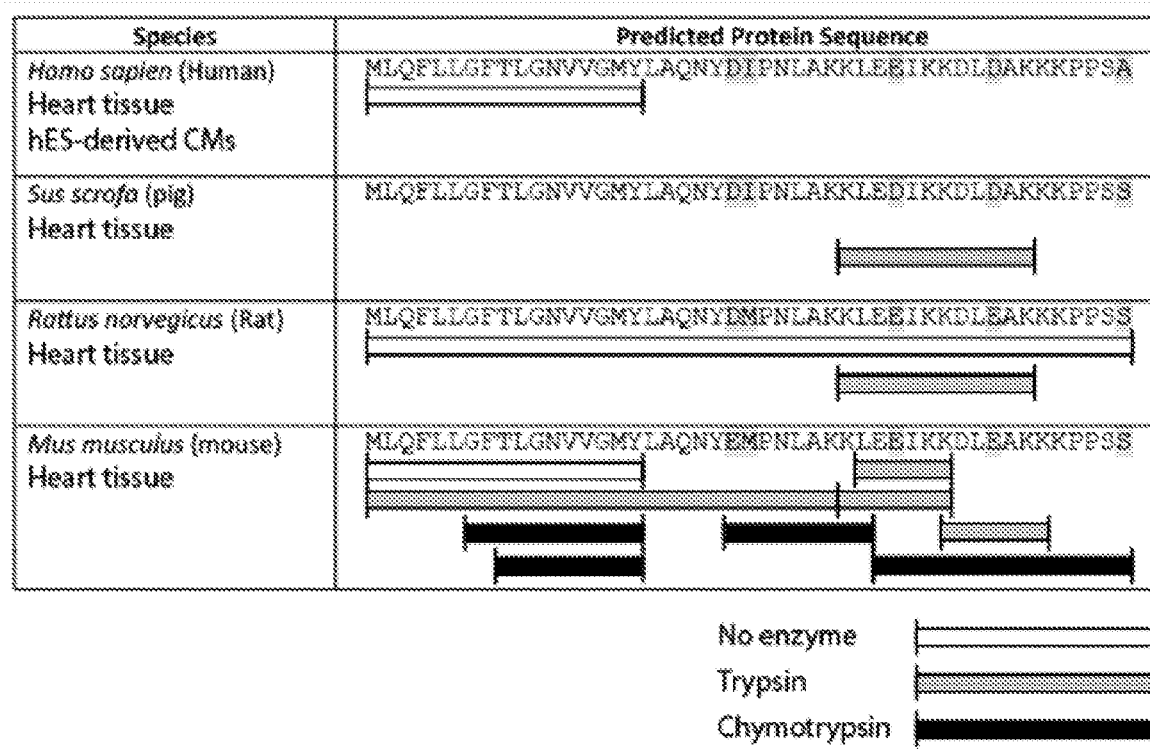
FIG. 4. Peptide mapping and coverage of STMP1 in mammalian mitochondria samples.

Mass spectrometry analysis was performed in a further experiment to confirm and resolve the protein sequence for SGHRT in mouse, rat, pig and human. Samples were prepared for proteomics analysis using a gel-assisted sample preparation (GASP) strategy (Fischer, R. & Kessler, B. M. Gel-aided sample preparation (GASP)—a simplified method for gel-assisted proteomic sample generation from protein extracts and intact cells. Proteomics 15, 1224-1229, doi: 10.1002/pmic.201400436 (2015)). Peptide mapping was done in mitochondria enriched heart samples and hES-derived CM. To increase protein coverage, LC-MS/MS was done in undigested, trypsin digested, as well as chymotrypsin digested samples. Fragments of human SGHRT peptides were detected and confirmed in limited human heart cadaver samples available, and full coverage was achieved in rat and mouse samples (FIG. 4).

Sghrt locus is therefore found to harbour a sORF and encode for a 47-amino acid mitochondrial micropeptide (derived from a mitochondrial long noncoding RNA) that may account for Sghrt therapeutic and biomarker potential/value. The micropeptide is named Short transmembrane mitochondrial protein 1 precursor, or STMP1. A peptide sequence with 100% homology has been isolated in a proteome screen of bovine cardiac mitochondrial fractions, and co-purified with subunit 9 of mitochondrial respiratory complex III. Moreover, multiple sequence alignment demonstrates that the STMP1 micropeptide sequence is highly conserved across vertebrates and targeting this sequence by morpholinos in zebrafish produced a phenotype including cardiac edema. In the present disclosure, Sghrt peptide sequence and fragments thereof were identified from the heart tissue extracts of mouse, rat, pig and humans. The results showed that Sghrt peptide sequence is highly conserved among different species, including among mammalian species.

Evidence Indicates Oligomerization of SGHRT Micropeptides

Figure 5:
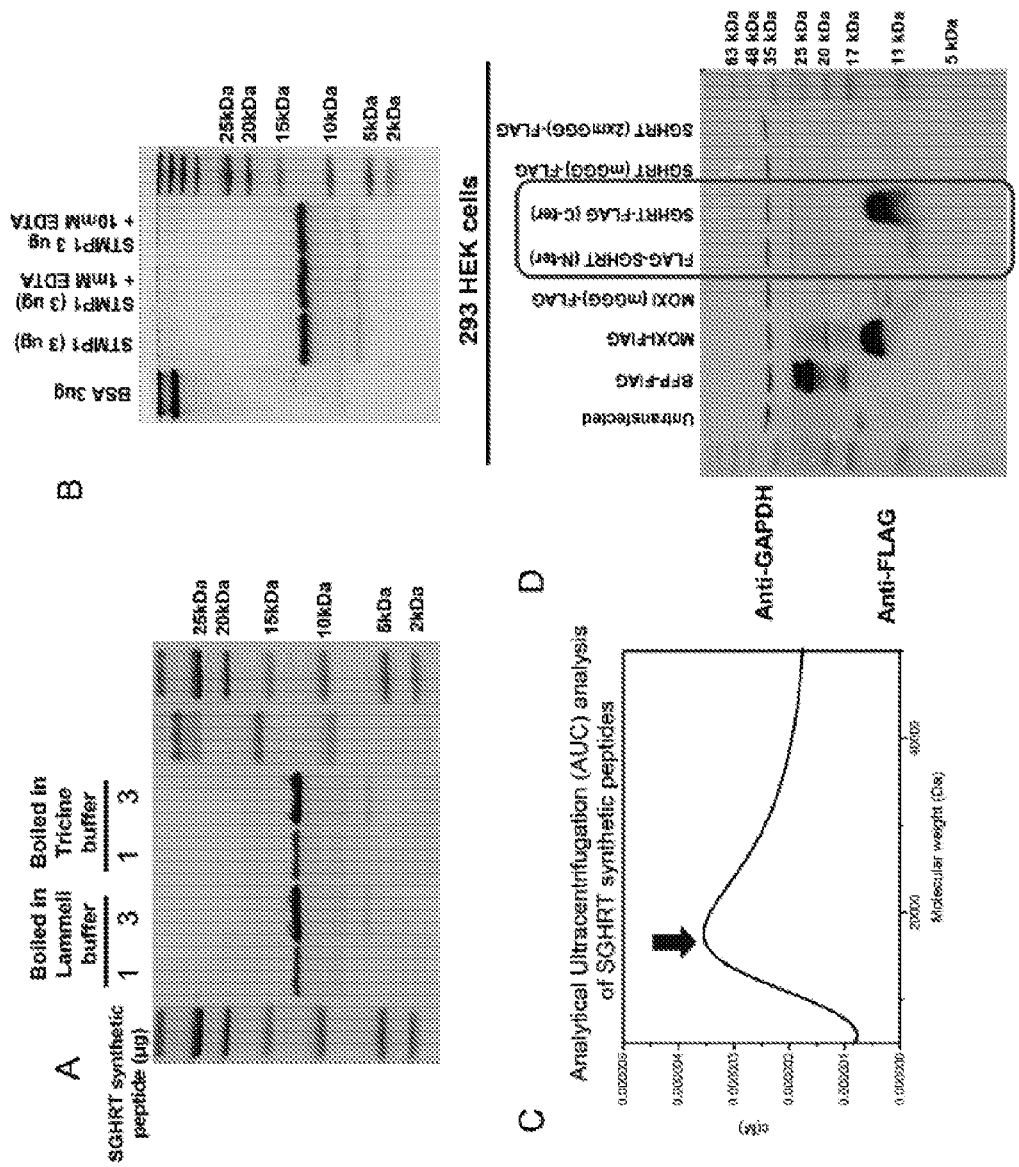
FIG. 5. Preliminary evidence indicates SGHRT micropeptide oligomerisation. A, 1 ug and 3 ug of SGHRT synthesised peptides were boiled for 10 mins and run in 16.5% Tricine gel and the Gel was stained with Coomassie Blue solution. B, 3 ug of SGHRT synthesised peptides were treated with 1 mM and 10 mM EDTA for 30 mins and then run in 16.5% Tricine gel and the Gel was stained with Coomassie Blue solution. C, Analytical Ultracentrifugation (AUC) analysis of SGHRT synthesised peptides suggested that molecular weight of SGHRT peptides is in the range of 15-20 KDa, and the highest peak is at ~17 KDa. D, Western blot with FLAG antibody showing a 12 KDa band in protein lysates of HEK cells transfected with SGHRT-FLAG vector in which SGHRT was C-terminal FLAG tagged, but not in lysates from cells transfected with FLAG-SGHRT vector in which SGHRT was N-terminal FLAG-tagged or with ATG-mutated SGHRT-FLAG.

The expected size of SGHRT micropeptide is ~5.8 KDa. However, when SGHRT synthesized peptides were run in 16.5% Tricine SDS gel, three bands were observed at ~5.8 KDa, ~8 KDa and ~12 KDa, with the 12 KDa band being most abundant (FIG. 5A). This result suggests that SGHRT presents in an oligomer, which could be a dimer or trimer. The SGHRT oligomer was also resistant to heat (FIG. 5A) and EDTA treatment (FIG. 5B), suggesting that a covalent bond is not responsible for the oligomerisation. To analyze the molecular weight of SGHRT peptides quantitatively in solution, Analytical Ultracentrifugation (AUC) analysis of SGHRT synthetic peptides was performed. The result indicated that the molecular weight of SGHRT peptide is in the range of 15-20 KDa and the highest peak was again at ~17 KDa (FIG. 5C). To validate that SGHRT oligomerisation also occurs in vivo, HEK cells were transfected with SGHRT-FLAG or FLAG-SGHRT vectors in which SGHRT was FLAG-tagged at the C- or the N-terminus, respectively. Interestingly, a strong band was consistently identified at ~12 KDa when SGHRT-FLAG was C-terminal tagged, but not N-terminal. As additional control, this band was absent in HEK cells transfected with mutated SGHRT in which the ATG was replaced by GGG (FIG. 5D). Taken together, the results were consistent with the conclusion that SGHRT micropeptides form oligomers, which could be dimers or trimers.

Figure 6:
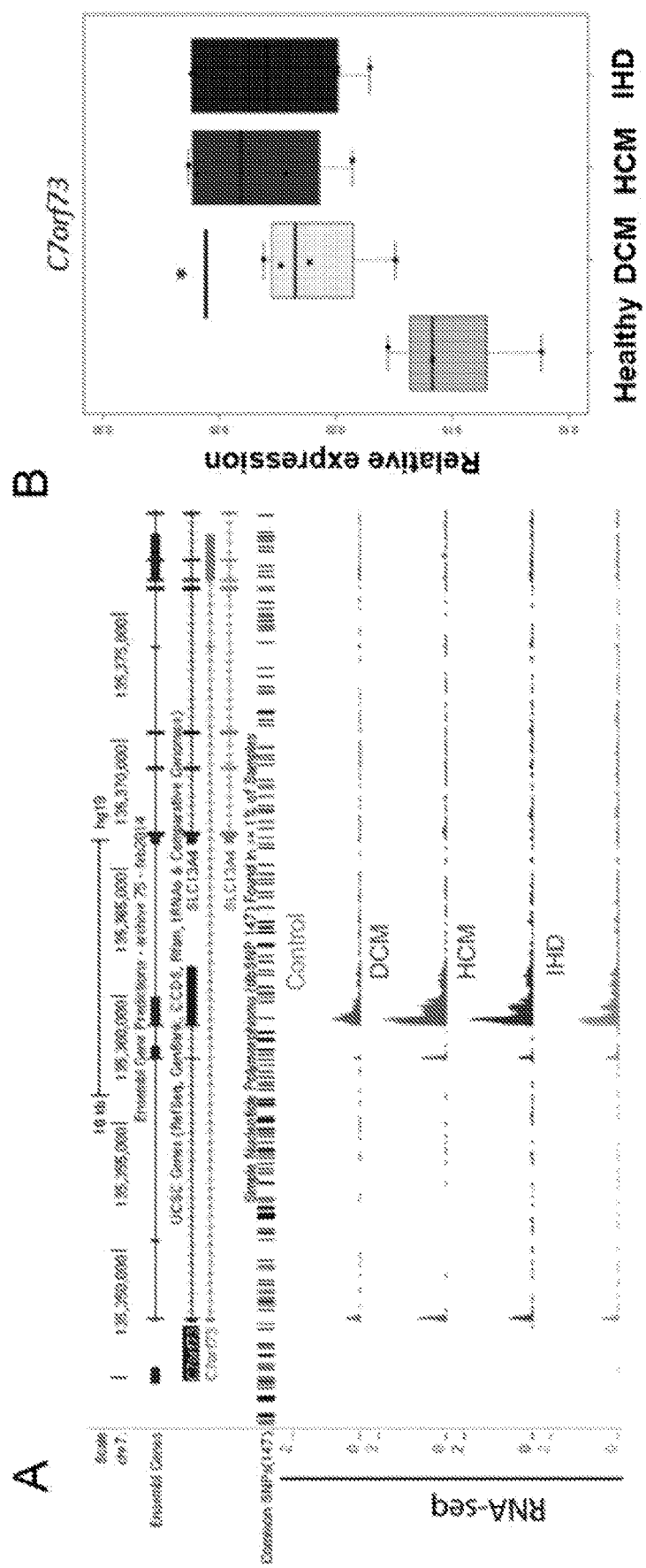
FIG. 6. Upregulation of SGHRT in human hearts with End-stage HF. A, RNA-seq tracks showing higher expression of SGHRT in Dilated Cardiomyopathy (DCM), Hypertrophic cardiomyopathy (HCM) and Ischemic Cardiomyopathy (IHD) patients compared to heathy hearts. B, RT-qPCR validation of SGHRT upregulation in cardiac tissue from patients with end-stage HF.

SGHRT mRNA Expression is Upregulated in the Left Ventricles of End-Stage HF Patients Human LV samples harvested with an ongoing protocol approved by the Papworth (Cambridge) Hospital Tissue Bank Review Board and the Cambridgeshire Research Ethics Committee (UK) were available. These samples were from patients undergoing cardiac transplantation for end-stage ischemic and idiopathic cardiomyopathy. Based on >50 of these samples, and a continuous constant supply every month, a genome-wide mapping of differential DNA methylation and H3K36me3 enrichment profiles, a landscape of DNA repeats and circular RNAs in human end-stage HF was done. Relevant to this Gap proposal, RNA-seq and RT-qPCR validation using the human LV samples showed that SGHRT mRNA levels were upregulated in a range of diseased HF hearts (FIG. 6, DCM: dilated cardiomyopathy; HCM: hypertrophic cardiomyopathy; IHD: ischaemic cardiomyopathy).

Increased Dedifferentiated CMs in SGHRT-KO hES Differentiation and Engineered Heart Tissue (EHT)

To validate whether SGHRT regulates differentiation of human CM, a SGHRT knockout hES cell-line was generated using CRISPR/CAS9 technology to specifically delete the promoter and first exon of the SGHRT gene. The efficient and precise genome edited in SGHRT-KO hESCs, with a complete loss of SGHRT mRNA expression, was validated. By RT-qPCR, immunostaining, and Western blot, it was proven that that there was no change to OCT4 mRNA/protein and NANOG mRNA, showing that SGHRT-KO hESCs maintained their pluripotency, and stemness was not affected by SGHRT KO.

Figure 7:
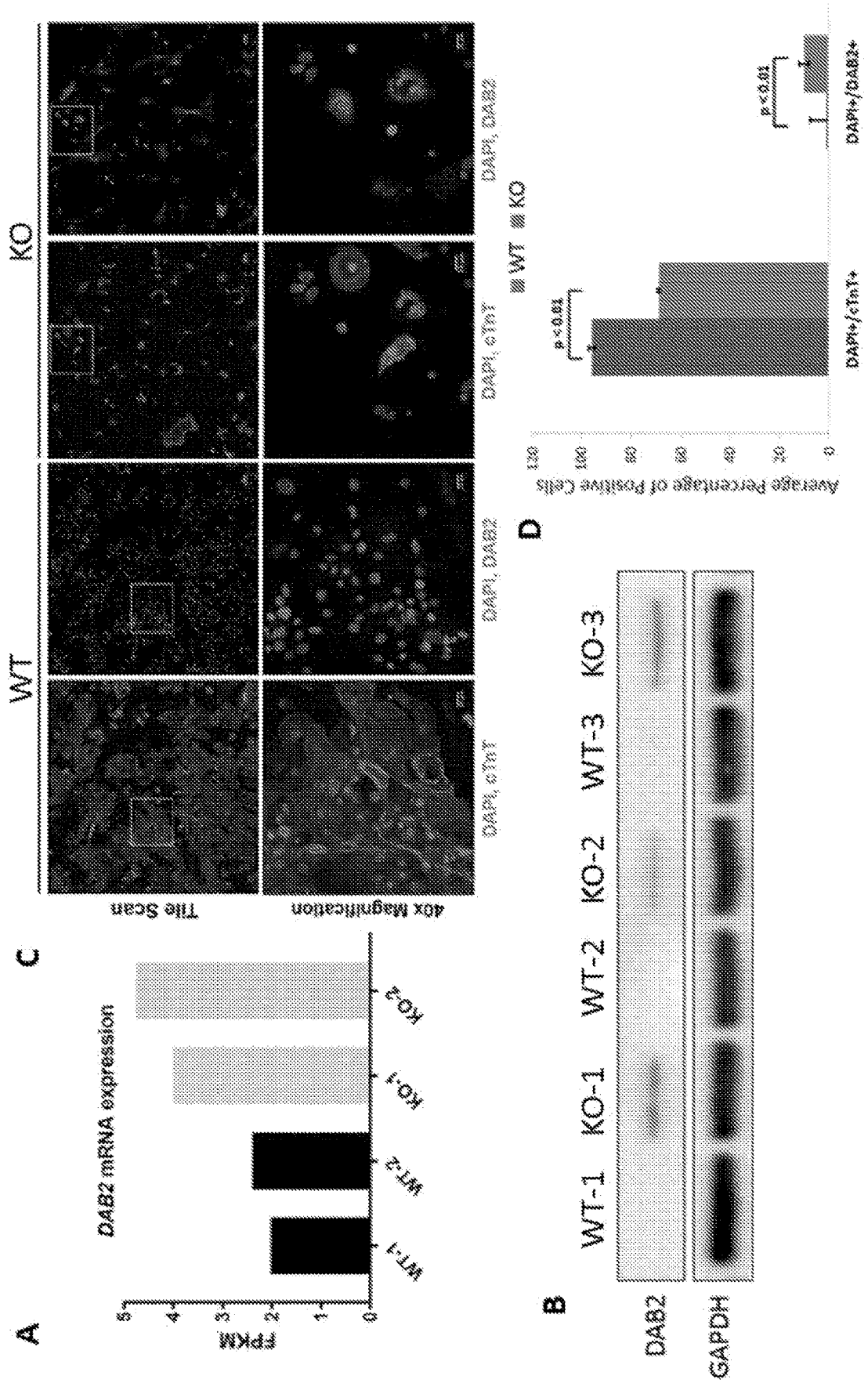
FIG. 7. SGHRT knockout in hESC-CMs results in increased DAB2+ CMs. A, RNA-seq data showing increased mRNA expression of DAB2 in D58 SGHRT KO hESC-CMs. B, Western blot result showing increased DAB2 protein expression in D58 SGHRT KO hESC-CMs. GAPDH was used as loading control. C, Representative microscope images showing an increase in DAB2+hESC-CMs and a decrease in cTnT+hESC-CMs after SGHRT knockout at D58. White boxed areas are magnified to 40×. D, SGHRT knockout resulted in increased DAB2+ CMs at D58 time points.
Figure 8:
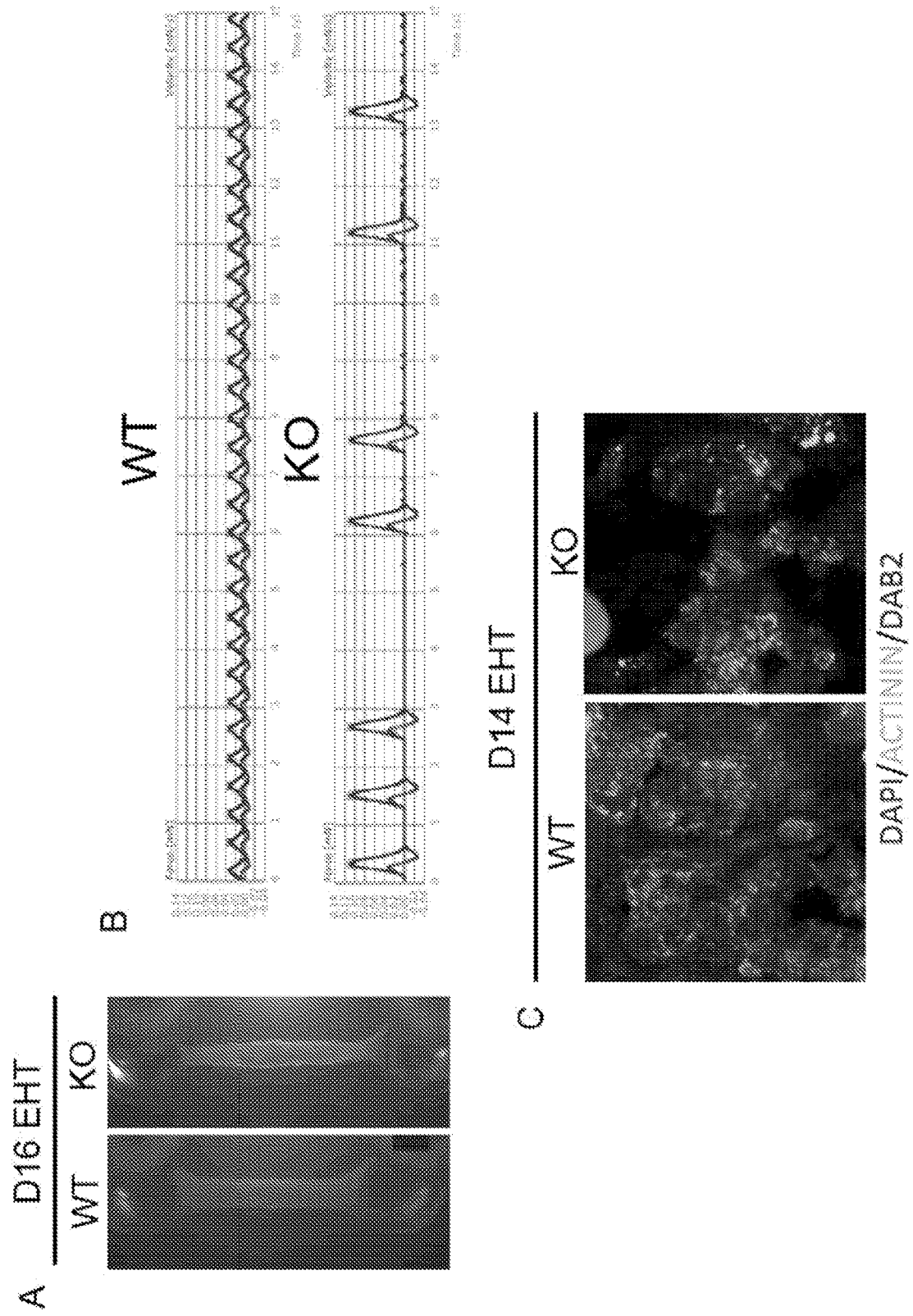
FIG. 8. SGHRT KO EHT show poorly formed EHT profile and increased dedifferentiated DAB2+ CMs. A, Representative pictures of EHT generated from wildtype and SGHRT knockout hESC-CMs at D16. B, Contractility profile of SGHRT WT and KO of D16 EHT. C, Representative microscope images showing an increase in DAB2+ CMs in SGHRT KO D14 EHT.

Next, CM differentiation was performed using SGHRT-KO hESCs and harvested CM cultures at D58. SGHRT-KO CMs (MYH6-GFP reporter positive) appeared rounder, smaller, and with higher nucleus/cytoplasm ratio compared to the WT CMs (data not shown), suggesting that these cells may be acquiring cardiac progenitor-like characteristics. DAB2 mRNA and protein increase was also proven with RNA-seq and Western blot (FIG. 7A-B). There was significant increase in DAB2$^+$ cells in SGHRT-KO (<1% in the WT compared to 11.2% DAB2$^+$ CMs in D58 SGHRT KO, FIG. 1C-D). Consistently, there was also a significant decrease in cTnT$^+$ (96.0% in WT cultures compared to 71.3% in D58 SGHRT-KO). These results lend further suggestion that dedifferentiated CMs lose CM characteristics and take on more progenitor-like characteristics. Moreover, using an EHT system that the lab has now robustly established (http://foo-lab.com/video/EHT.html) in collaboration with Thomas Eschenhagen (Hamburg), constructed EHT using WT and KO D14 hES-CM showed a loss in tissue structure (FIG. 8A-B) and increased DAB2$^+$ CMs (FIG. 8C). Taken all together, the results thus far showed that the loss of SGHRT increases dedifferentiation of mature CMs both in vivo and in vitro.

Sghrt KD induces dedifferentiation of neonatal mouse cardiomyocytes in vivo

Figure 9:
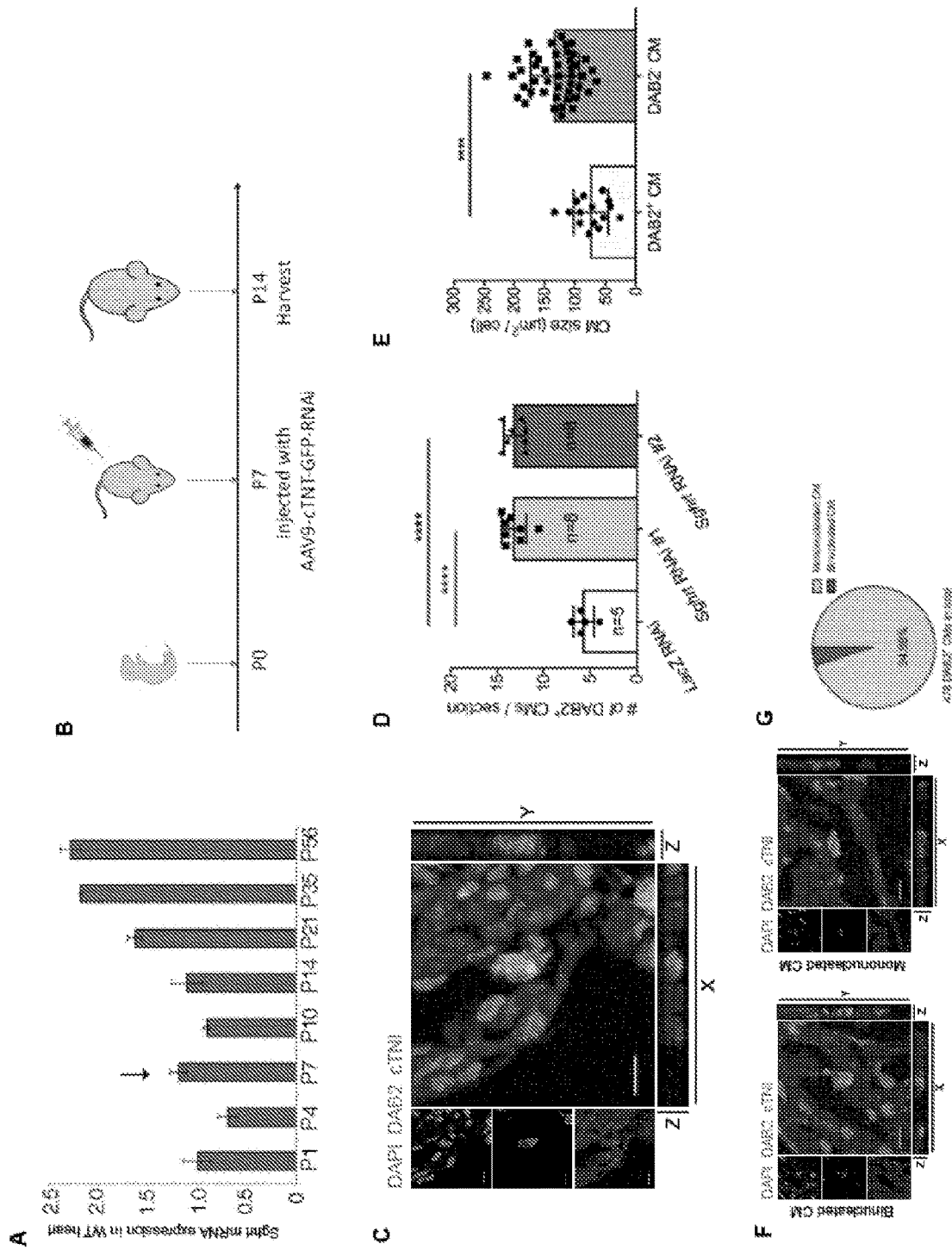
FIG. 9. Sghrt knockdown resulted in CM dedifferentiation in neonatal (P7) mouse. A, Expression of Sghrt in whole hearts from P1 to P56 mice. B, Injection of AAV9-cTNT-GFP-RNAi to knockdown Sghrt in P7 WT mice. C, Representative pictures of a typical DAB2+ and cTNI+ cardiomyocytes, confocal images with z-stacking showing co-localization of DAB2 and cTNI signals. D, Quantification of DAB2+ CMs per heart section from control mice and mice with Sghrt KD (2 sections from each heart were analysed). E, Cell sizes of DAB2+ CMs and their neighbouring DAB2-CMs. F, Representative pictures of a binucleated DAB2+CM (left, the two nuclei are indicated by the white arrows) and a mononucleated DAB2+CM (right). G, Graph showing the percentage of binucleated and mononucleated DAB2+ CMs. ****$P<0.0001$ (Student's t-test).

Mouse CMs enter cell cycle arrest at the end of their proliferation window at the 7th postnatal day (P7). Hence, Sghrt transcript levels during normal mouse heart development across this proliferation time-course window were assessed. It was found that Sghrt expression increased progressively from P10 onwards with age (FIG. 9A). The end of the proliferation window at P7 coincided with a small but statistically significant expression spike in Sghrt. To test if Sghrt regulates CM dedifferentiation in vivo and assess the validity of the in vitro KD results, CM-specific in vivo KD in P7 mice was targeted (FIG. 9B) using the AAV9-TNNT2-eGFP RNAi delivery system. Following injection of either AAV9-TNNT2-eGFP-Sghrt KD in P7 mice, hearts were harvested at P14. Sghrt-KD hearts indeed bore significantly more dedifferentiated CMs (DAB2$^+$) (FIG. 9C,D).

Next, it was confirmed that DAB2+ CMs possessed the typical properties of dedifferentiated CMs with cell size and number of nuclei. DAB2+ CMs (n=15) were smaller than their neighbouring DAB2-CMs (n=45) (FIG. 9E). Among all 478 DAB2+ CMs, 94.98% were mononucleated (FIG. 9F, right panel and FIG. 9G) and only very few of them were binucleated (FIG. 9F, left panel). These results indicated that KD of Sghrt resulted in CM dedifferentiation in neonatal mouse.

Figure 10:
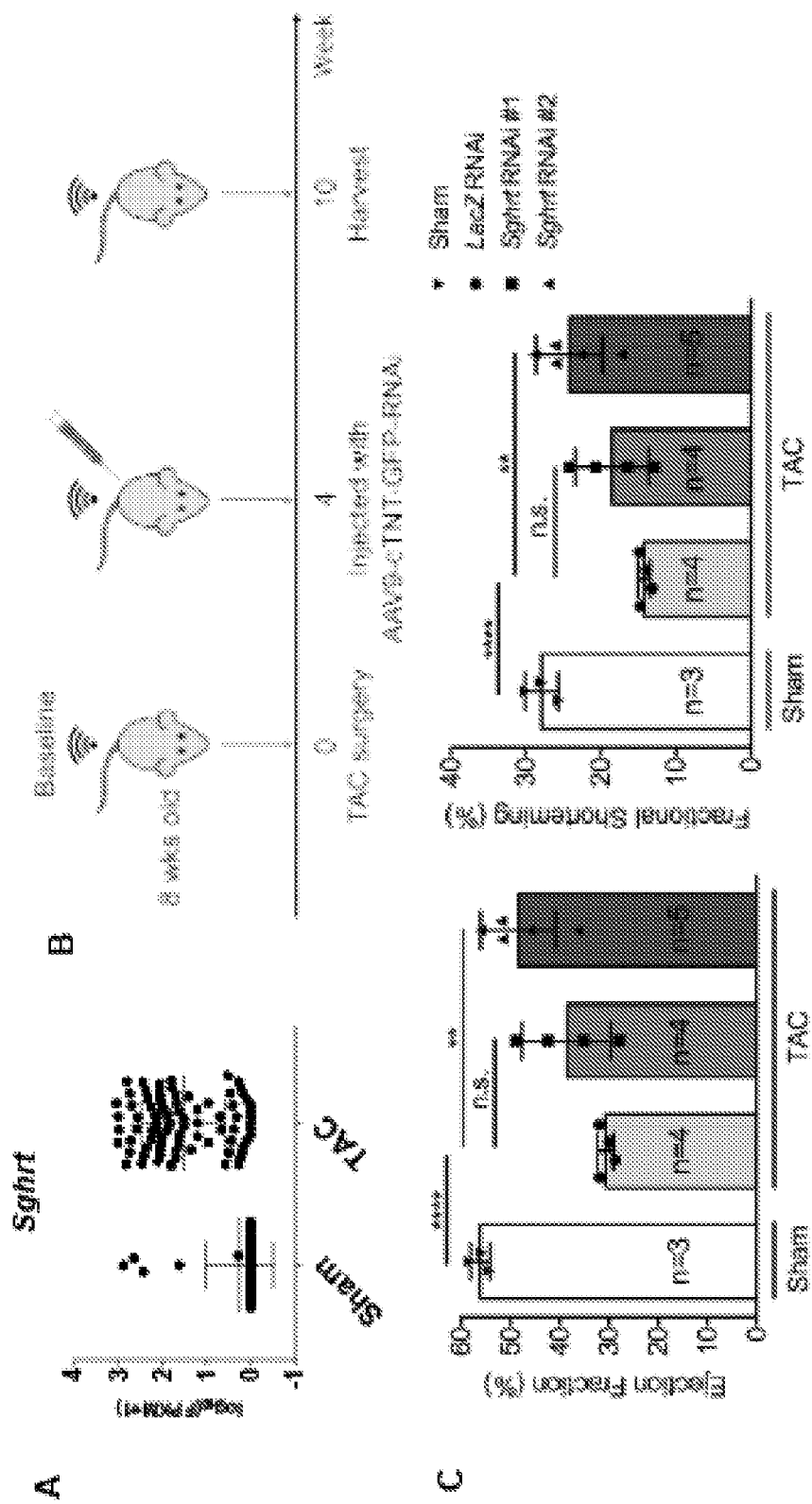
FIG. 10. KD of Sghrt rescued cardiac function and induced CM dedifferentiation in TAC mouse model within 6 weeks. A, Single nuclear RNA-seq show an upregulation of Sghrt mRNA expression in single nucleus isolated from TAC CMs compared to those from Sham CMs. Each dot represents a single CM nucleus. B, Diagram showing the timeline of TAC surgery on 8-week-old WT mice, followed by AAV9 injection and harvesting. C, Graphs showing EF and FS of Sham mice, control mice with TAC and Sghrt KD mice with TAC, 6 weeks after AAV9 injection. D, Representative pictures of a typical DAB2+ and cTNI+ cell. E, Quantification of DAB2+ CMs per heart section (3 sections from each heart were analysed). F, The cell size of DAB2+ CMs and their neighbouring DAB2-CMs. G, Representative pictures of a binucleated DAB2+CM (top panel) and a mononucleated pH3+CM (bottom panel). (I) Graph showing the percentage of binucleated and mononucleated DAB2+ CMs. n.s. $P>0.05$, $P<0.01$, **$P<0.0001$ (Student's t-test).
Figure 10:
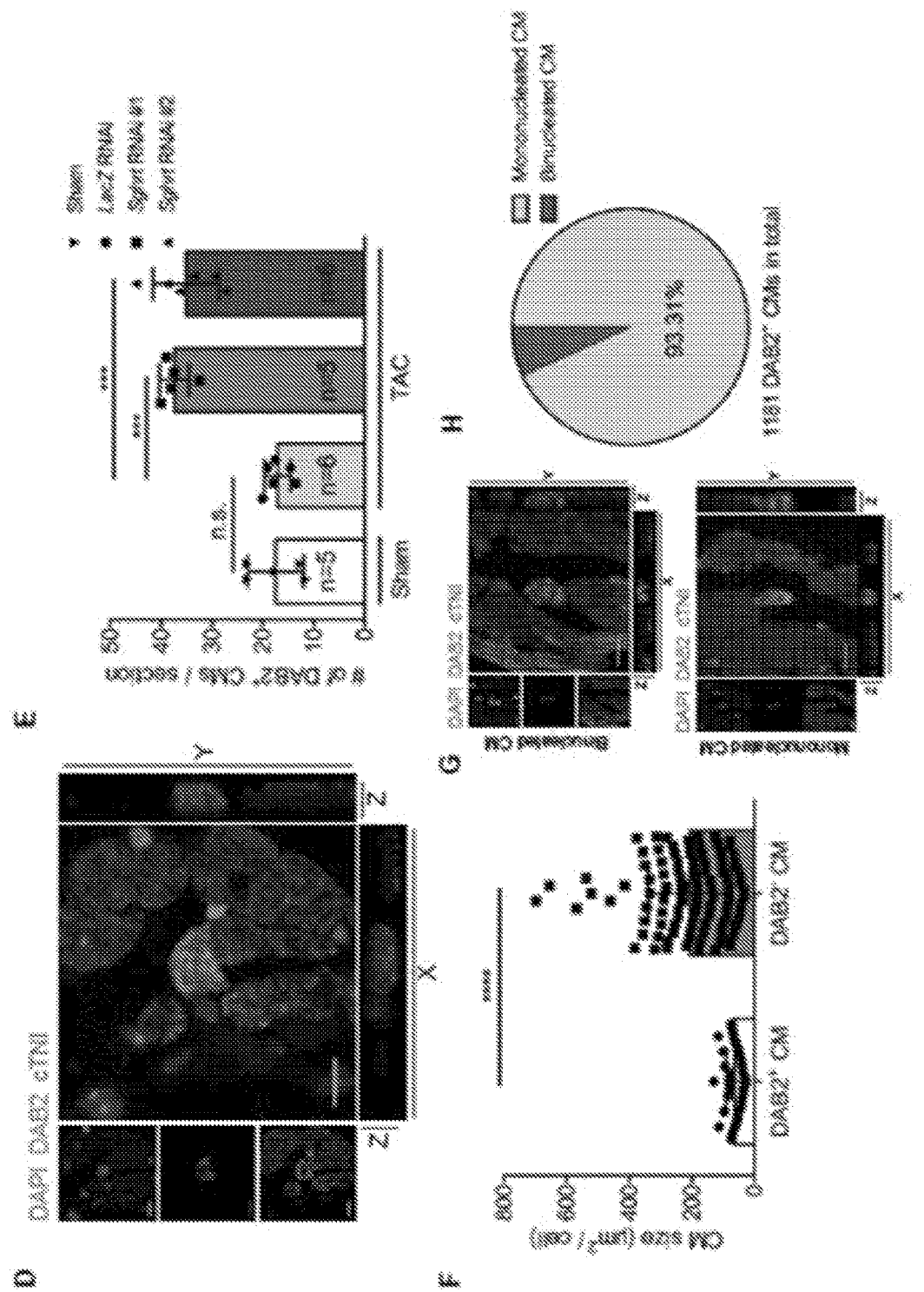

Sghrt Knockdown Results in Increased Dedifferentiation of Adult Mouse Cardiomyocytes and Functional Recovery after TAC Pressure Overload Single nuclear RNA-seq on cardiomyocytes isolated from healthy and failing adult mouse left ventricles revealed Sghrt to be highly upregulated in a subpopulation of cardiomyocytes (FIG. 10A). This subpopulation of cardiomyocytes was unique because of their expression pattern in the genes encoding for cell cycle activators and inhibitors. Through gene network analysis, Sghrt stood out as a putative key regulator for the cardiomyocyte stress gene programme. Therefore, it was decided to carry out Sghrt knockdown in the TAC pressure overload HF model.

Four weeks after TAC surgery, mice were injected with AAV9 to deliver 2 unique Sghrt RNAi reagents of either Sghrt-RNAi-#1, Sghrt-RNAi-#2, or the control LacZ sequence. Six weeks after AAV9 injection, mice were assessed by echocardiography before their hearts were harvested and assessed for CM dedifferentiation by immunofluorescence staining (FIG. 10B). Mice receiving LacZ as control (n=4) showed the expected significant deterioration in cardiac function (EF % and FS %) from TAC-surgery, compared to Sham-operated mice (n=3). Cardiac function of mice from Sghrt-RNAi-#2 group was significantly rescued. No significant difference was found between the EF % and FS % of Sghrt-RNAi-#1 and control groups (FIG. 10C), possibly due to the larger variation within groups and small sample size.

Importantly, more DAB2+ cardiomyocytes (FIG. 10D) per heart section were found, 6 weeks after Sghrt KD, compared to control mice (FIG. 10E), where DAB2 has been proposed as a bona fide marker of cardiomyocyte dedifferentiation. Consistent with the hallmark of cardiomyocyte dedifferentiation in DAB2-positive cells, DAB2+ CMs (n=36 CMs) were overall smaller than the DAB2-CMs (n=108 CMs) (FIG. 10F), and they were also predominantly mononucleated (FIG. 10G-H). The results thus suggest that Sghrt KD improves heart function of failing mouse heart, associated with enhanced dedifferentiation of adult mouse cardiomyocytes in Sghrt-inhibited hearts.

SGHRT Micropeptide is Required for Fatty Acid Utilization in Cardiomyocytes

Figure 11:
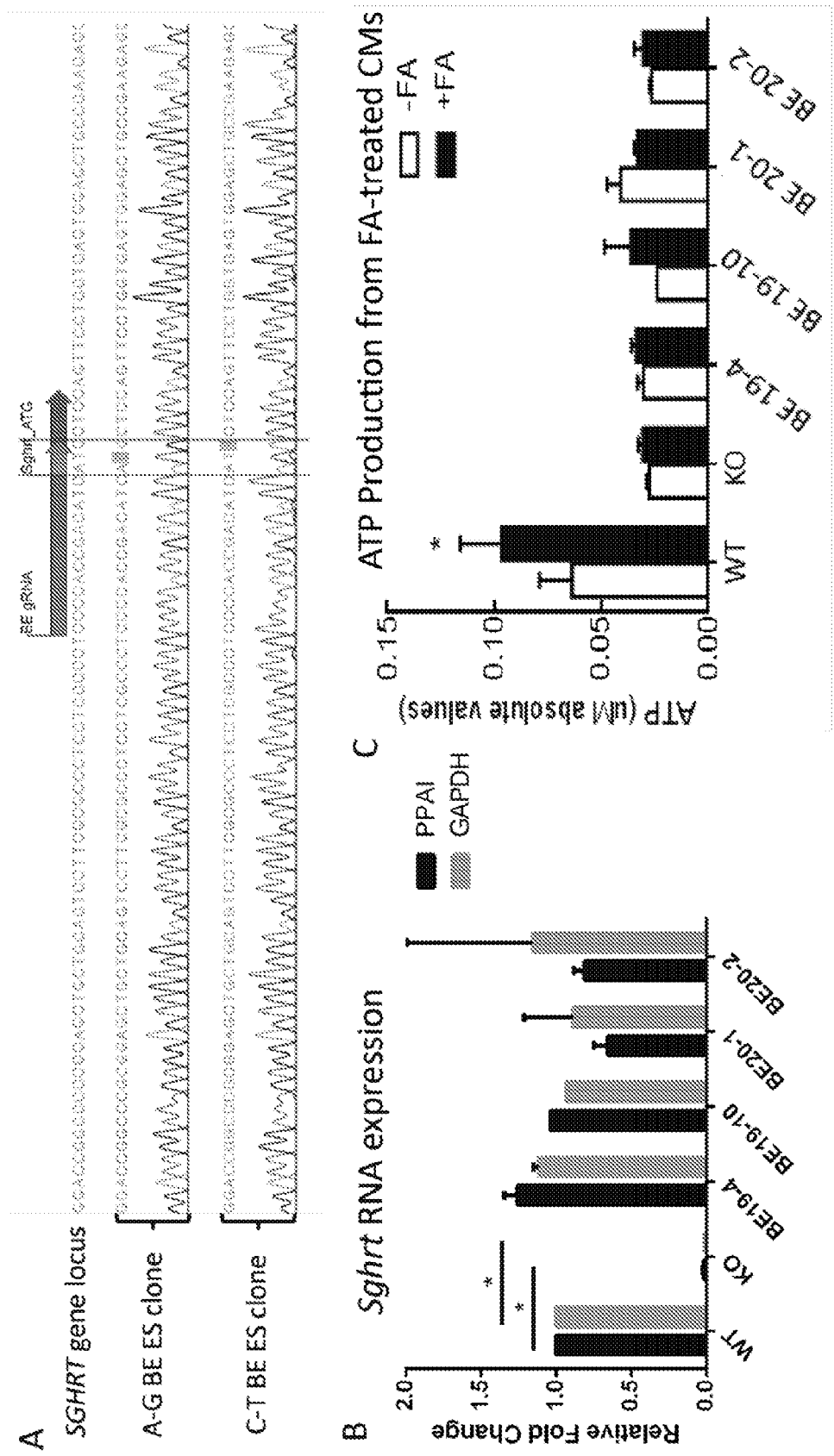
FIG. 11. A, Representative DNA sequencing result confirmed that 2 A-to-G (BE19-4 and BE19-10) and 2 C-to-T (BE20-1 and BE20-2) based editing ES clones were successfully generated. B, Q-PCR results showed no change in SGHRT RNA expression in BE ES clones. C, Quantification of ATP production in WT, KO and BE ES-derived CM clones with and without Fatty Acid treatment.

To study function of SGHRT micropeptide in cardiomyocytes, ATG (TCG in reverse strand)-mutated human embryonic stem (ES) cell clones were generated using CRISPR-CAS based editing technology to change A or C into G or T (Komor, A. C., Kim, Y. B., Packer, M. S., Zuris, J. A. & Liu, D. R. Programmable editing of a target base in genomic DNA without double-stranded DNA cleavage. Nature 533, 420-424, doi: 10.1038/nature17946 (2016); Gaudelli, N. M. et al. Programmable base editing of A*T to G*C in genomic DNA without DNA cleavage. Nature 551, 464-471, doi: 10.1038/nature24644 (2017).) DNA sequencing confirmed that 2 A-to-G (BE19-4 and BE19-10) and 2 C-to-T (BE20-1 and BE20-2) based editing ES clones were successfully generated (FIG. 11A). The Q-PCR data indicated there was no significant change in SGHRT RNAs in BE ES clones compared to WT ES (FIG. 11B), suggesting that changing ATG site in SGHRT DNA did not affect RNA expression. These BE ES clones were then differentiated into cardiomyoctes (CMs) and ATP measurement was performed on these cardiomyocytes treated with or without Fatty Acid (FA). It was found that WT CMs produce more ATP when treated with FA compared to non-treated condition whereas KO and BE CM clones did not produce more ATP in response to FA treatment (FIG. 11C). Taken together, these results suggested that SGHRT is a mitochondria micropeptide required for FA utilization in cardiomyocytes.

Experimental Procedures

Tissue and Cell Samples

Human heart (Left Ventricle) samples were collected with an ongoing protocol approved by the Papworth (Cambridge) Hospital Tissue Bank Review Board and the Cambridgeshire Research Ethics Committee (UK). Samples were from patients undergoing cardiac transplantation for end-stage ischemic and idiopathic cardiomyopathy. The tissues were frozen and kept in −80° C. freezer until being used for mitochondria extraction.

Pig, rat and mouse heart (Left Ventricles) samples were collected from pig, rat and mouse respectively, snapped frozen and kept in −80° C. freezer until being used for mitochondria extraction.

Human ES-derived cardiomyocytes were collected from cell culture, snapped frozen and kept in −80° C. freezer until being used for extraction.

Extraction of Mitochondria from Tissue

Tissue was cut into small pieces using tweezer and scissors, then homogenised with a mechanical blender in hypotonic buffer (NaCl 10 mM, MgCl2 1.5 mM, Tris 10 mM, adjusted with HCl to pH 7.5). Cells were then ruptured by douncing until approximately 80% of cell nucleus was naked. The cell lysate was then rendered isotonic by adding a concentrated mannitol solution to final concentration of 210 mM mannitol, 70 mM sucrose, 5 mM Tris, 1 mM EDTA, adjusted with HCl to pH 7.5.

Intact cells and nucleus were then depleted from the lysate by centrifuging at 1300 g for 5 minutes at 4° C. and discarding the pellet for three cycles. Mitochondria were then harvested from the supernatant as a pellet by centrifuging at 8000 g for 15 minutes at 4° C., discarding the supernatant, and then resuspending in isotonic mannitol solution for two cycles.

Extraction of Membrane Protein from Mitochondria

Organic cell lysis buffer [2-propanol: acetonitrile: hexafluoro-isopropanol: water (70:25:0.56:4.44, by vol) containing 20 mM ammonium formate, pH 3.7] was added to the mitochondria pellet at approximately 9:1 volumetric ratio. The lysate was then vortexed for 1 minute and sonicated for 15 minutes in ice water bath. The supernatant obtained after centrifuging at 21,000 g for 10 minutes at 4° C. was then used for LC-MS.

LC-MS

An Agilent Infinity II 6550B UPLC-QTOF system was used for LC-MS. Mobile phases for UPLC chromatography were water with 0.1% formic acid and acetonitrile with 0.1% formic acid. Reverse phase separation was performed using a Phenomenex Luna Omega 1.6 um Polar C18 100 A LC Column 100×2.1 mm, with linear gradient of 20% to 80% over 20 minutes. The eluent was connected online to the mass spectrometer to acquire mass spectrum over time.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

Stem Cell Maintenance and Differentiation

Human embryonic stem cell line H1 was maintained using m TeSR medium (Stemcell Technologies, 85850) on 1:200 growth factor-reduced Geltrex (Thermo fisher, A1413202) coated tissue culture plates and passaged regularly as cell aggregates every 4-5 days using ReLeSR (Stemcell Technologies, 05872), an enzyme-free dissociation reagent specific for human pluripotent stem cells). Two days prior to starting differentiation, cells were dissociated using Accutase (Stemcell Technologies, 07922) and seeded as single cells in Geltrex-coated 12-well plates (passage ratio 1:2, between 500'000-600'000 cells). Differentiation was performed following the published protocol by Lian et al. (Lian et al. Directed cardiomyocyte differentiation from human pluripotent stem cells by modulating Wnt/beta-catenin signaling under fully defined conditions. *Nature protocols* 8, 162-175, doi: 10.1038/nprot.2012.150 (2013)) with modifications as follows. 10 UM of CHIR99021 (Stemcell Technologies, 72054) was added on day 0 and left for 24 hours followed by medium change. On day 3, 5 uM IWP2 (Sigma Aldrich, 10536) was added using 50/50 mix of new fresh medium and conditioned medium collected from each well and left for 48 hours. Culture medium from day 0 until day 7 was RPMI1640 (HyClone, SH30027.01) plus B-27 serum-free supplement without insulin (Gibco, A1895601). From day 7 and onwards, RPMI1640 with B-27 serum free supplement with insulin (Gibco, 17504044) was used and changed every 2-3 days.

Generation of MYH6-GFP Reporter Line

EGFP cassette with kanamycin selection was inserted into BACs for MYH6 (RP11-834J17, BacPac) immediately before the initiating Methionine (ATG) using recombineering (Quick & Easy BAC Modification Kit, KD-001, Gene Bridges GmbH). The Tol2 transposon cassette with Ampicilin selection mark was inserted into the loxp site of the BAC in the backbone using recombineering. Ten million H1 cells were cultured in CF1 conditioned medium (20% KO serum replacement, 1 mMI-glutamine, 1% non-essential amino acids, 0.1 mM 2-mercaptoethanol and 8 ng ml-1 of basic fibroblast growth factor in DMEM: F12) for 6 days and dissociated into single cells with TrypLET Express (Life Technologies) and electroporated with 20 micrograms of Tol2 transposes and 100 micrograms of Tol2/EGFP modified Transposon-BACs. After electroporation, cells were re-suspended in conditioned medium with 10 UM ROCK inhibitor Y276329 (Y27632 (Stemcell technology, 72302). ROCK inhibitor was added for the first 48 hours after electroporation. Fifty ug/ml geneticin (Gibco, 10131035) was added for selection of positive clones 72 hours post-electroporation. Fourteen days later after drug selection, single colonies were picked into 24 well plates for expansion. Fluorescent in situ hybridyzation (FISH) using non-modified BACs as probes was carried out to validate the incorporation of BAC construct into genome of ES cells (Cytogenetics Services, Genome Institute of Singapore). Karyotyping was performed to confirm a normal chromosome pattern.

Generation of SGHRT Knockout ESC Lines Using CRISPR/Cas9 Knockout

Plasmid pMIA3 (Addgene plasmid #109399; http://n2t.net/addgene: 109399; RRID: Addgene_109399) was used for CRISPR/Cas9 mediated KO. Two KO hESC lines were generated using dual single guide RNA (sgRNAs) to remove part of SGHRT. Single guide RNA sequence was designed using cloud based software tools for digital DNA sequence editing Benchling and CRISPOR. 10 UM sense and anti-sense oligonucleotides were ordered and annealed to generate the 20 nucleotide spacer that defines the genomic target to be modified (VHRT 5'end and 3'end). pMIA3 was digested with BsmBI and sgRNA spacers cloned after human U6 promoter with T4 DNA ligase (New England Biolabs) following manufacturer's instruction. Ligated constructs underwent transformation using RapidTrans™ Chemically Competent Cells (Active motif). Plasmid was extracted from bacterial culture, purified and Sanger sequenced to confirm successful cloning. Prior to hESC targeting, cutting efficiency of pMIA3-sgRNAs plasmids were tested on HEK293T using the EGxxFP plasmid (pCAG-EGxxFP was a gift from Masahito Ikawa, Addgene plasmid #50716). Best combination of sgRNAs was then used for final targeting of hESCs. The best pair of guides were cloned into a single pMIA3 plasmid digested with NheI & XbaI, using NEBuilder isothermal assembly (New England Biolabs), according to manufacturer's instructions to make the final pMIA3 dual sgRNA plasmid. Human ESCs were dissociated with Accutase (Stemcell Technologies, 07922) and ~1.5×10$^6$ cells were re-suspended in 100 µl P3 Primary Cell kit solution from Lonza (V4XP-3024) and mixed with 10 µg pMIA3dual sgRNA plasmid. To transfect hESC, nucleofection was performed using program CM-113 on the 4D-Nucleofector System (Lonza). Cells were then plated into Geltrex coated 6-well plate with mTeSR medium (Stemcell Technologies, 85850) containing 5 UM Y-27632. After 2 days in culture, cells were dissociated, FACS sorted for RFP positive cells and collected into a tube containing mTeSR medium (Stemcell Technologies, 85850) with 5 UM Y-27632. 500 to 2000 cells were plated into wells of 6-well plate containing the above media. Single cell clones were monitored and upon sizeable growth, colonies were picked and passaged. Genomic DNA was extracted for genotyping and screened for successful KO. RT-qPCR was performed to validate KD of SGHRT transcript.

Generation CRISPR/CAS9 Based Editing

Plasmid pMIA19-CBE4 and pMIA20-ABE7 were used for CRISPR/Cas9 mediated Based Editing (BE) to change from ATG to ATA and from ATG to ACG respectively. BE hESC lines were generated using single guide RNA (sgRNAs) to edit from ATG to ATA site or from ATG to ACG of SGHRT. Single guide RNA sequence was designed using cloud based software tools for digital DNA sequence editing Benchling and CRISPOR. 10 UM sense and anti-sense oligonucleotides were ordered and annealed to generate the 20 nucleotide spacer that defines the genomic target to be modified (VHRT 5'end and 3'end). pMIA19-CBE4 and pMIA20-ABE7 were digested with AarI and spacers cloned after human U6 promoter with T4 DNA ligase (New England Biolabs) following manufacturer's instruction. Ligated constructs underwent transformation using RapidTrans™ Chemically Competent Cells (Active motif). Plasmid was extracted from bacterial culture, purified and Sanger sequenced to confirm successful cloning. Human ESCs were dissociated with Accutase (Stemcell Technologies, 07922) and ~1.5×10$^6$ cells were re-suspended in 100 µl P3 Primary Cell kit solution from Lonza (V4XP-3024) and mixed with 10 µg plasmid. To transfect hESC, nucleofection was performed using program CM-113 on the 4D-Nucleofector System (Lonza). Cells were then plated into Geltrex coated 6-well plate with mTeSR medium (Stemcell Technologies, 85850) containing 5 UM Y-27632. After 2 days in culture, cells were dissociated, FACS sorted for RFP positive cells and collected into a tube containing mTeSR medium (Stemcell Technologies, 85850) with 5 UM Y-27632. 500 to 2000 cells were plated into wells of 6-well plate containing the above media. Single cell clones were monitored and upon sizeable growth, colonies were picked and passaged. Genomic DNA was extracted for genotyping and screened for successful base editing. RT-qPCR was performed to validate if there is any change in the expression of SGHRT transcript.

Immunostaining

Cells were fixed in 3.7% formaldehyde for 15 min at room temperature and stored in DPBS. They were permeabilized in 0.2% Triton X-100 for 15 min followed by a pre-blocking step with 2% BSA for 20 min. Primary antibody incubation was performed in DPBS+10% goat serum (except for Nkx2.5 for which donkey serum was used) overnight at 4 degree and secondary antibody incubation for 2 hours at room temperature. DAPI was included during the final washing step. Antibodies used were cardiac troponin T (Lab Vision, ms-295-P0, mouse, 1:500 dilution), α-DAB2 (Santa Cruz, rabbit, 1:200 dilution), alexa fluor 594 goat-anti-mouse, alexa fluor 546 goat-anti-rabbit (Life Technology, A-11071), alexa fluor 568 donkey-anti-goat (Life Technologies, A11057).

RNA and DNA Isolation

RNA was extracted using Direct-zol™ RNA MiniPrep Kit (Zymo, R2060). Cells were directly lysed using Trizol reagent (Thermo Fisher, 15596026). DNA was purified using PureLink Genomic DNA Mini Kit (Thermo Fisher, K182001). All experiments were performed following the manufacturer's instructions.

PCR and Reverse Transcription Quantitative PCR (RT-qPCR)

DNA or plasmid vector were PCR amplified using Q5 High-Fidelity 2×Master Mix (Bio Labs, M0492S) and target specific primers (IDT) following manufacturer's instructions.

RNA (50-500 ng) was reverse transcribed to cDNA using qScript Flex cDNA Kit (Quantabio, 95049-025) with a combination of random primers and oligo (dT). Subsequently, 1 µl of cDNA (1:10) was used to PCR amplify only specific SGHRT transcripts. The remaining cDNA (1:10) was mixed with PerfeCTa SYBR Green FastMix, low ROX (Quantabio, 95074-05K) and specific primers on a 384-well plate. Real time qPCR was run using ViiA 7 Real-Time PCR System (Applied biosystems). Average Cq was recorded and ΔΔCq method was used to calculate relative gene expression changes. Expression levels of genes were normalized against two housekeeping genes, GAPDH and PPIA.

Transverse Aortic Constriction (TAC) Model

In this disclosure, transverse aortic constriction (TAC) in adult mouse was used as the model of heart failure. TAC in mouse is an experimental model for cardiac hypertrophy and heart failure induced by LV pressure overload. In this model, the constriction at aortic arch between left common carotid artery and right common carotid artery initially obstructs the blood pumped from left ventricle (LV), leading to compensated hypertrophy of the heart and a temporary enhancement of cardiac contractility. However, this response to the chronic LV overload becomes maladaptive overtime, which eventually results in cardiac dilatation and HF, accompanied by fibrosis formation within myocardium. Compared to MI model, TAC provides a more gradual time course in the development of heart failure.

Evaluating Cardiac Function in Diseased Models of Heart Failure by Echocardiography Echocardiography (echo) detects the cavity and chamber wall of hearts by sound waves to produce live images, and is an important non-invasive experimental method to visualize the cardiovascular structures and evaluate cardiac function in mice and rats. Improved echo instrumentation can provide accurate assessment of LV systolic/diastolic function, chamber size and wall thickness in various mouse models of cardiovascular diseases. In this disclosure, echo was used to track the structural and functional changes in TAC and MI mouse models.

Quantification and Characterisation of Dedifferentiated CMs by Immunofluorescence Staining and Confocal Microscopy The method of characterising CM dedifferentiation is not as well-established as that of CM proliferation, which can be indicated by markers of different cell-cycle stages. Based on all the existing publications related to CM dedifferentiation, the following criteria has been used to identify it: 1) loss of contractility and electrophysiological properties; 2) disassembled sarcomere or decreased expression level of sarcomeric genes; 3) expression of stem/cardiac progenitor cell markers, among which disabled homolog 2 (DAB2) is most commonly used. The first criterion is usually used to judge in vitro dedifferentiation of single CM, rather than CMs from heart tissue sections, while the last criterion is quite controversial. DAB2 is a target of GATA transcription factors and its increase may reflect increased expression of GATA4/6, a reported regulator of cardiac hypertrophy. Quantitative proteomics of human embryonic stem cells (hESCs), cardiac progenitor cells (CPCs), and cardiomyocytes also identified DAB2 as crucial cardiac developmental regulator. However, there is no direct evidence showing the change of DAB2 expression level in CMs over heart development, nor is its role in the dedifferentiation of other cell types. The first publication using DAB2 to indicate CM dedifferentiation also didn't provide detailed rationale of choosing it as a marker. Therefore, in this disclosure, immunofluorescence (IF) staining and confocal microscopy were used to identify CMs that are immune-positive of DAB2, of which the sarcomere would be judged as well-assembled or not based on IF staining of CM sarcomeric gene. Besides, the cell size of DAB2$^+$ CMs were measured, and the number of nuclei within these CMs were counted, as dedifferentiated cells are generally smaller and have fewer organelles compared to matured cells.

In Vivo Knockdown (KD) of Sghrt in CMs Via Adeno-Associated Virus Serotype 9 (AAV9) Containing CM-Targeting RNA Interference System RNA interference (RNAi) is an approach to silencing target genes by degrading the mRNA, achieved by introducing small double-stranded interfering RNAs (siRNA) into the cytoplasm. Adeno-associated virus (AAV) is an ideal vector for gene or siRNA delivery due to its low immunogenicity and stable gene expression, and AAV serotype 9 (AAV9) provides global cardiac gene transfer in mouse and rat, which is superior to other serotypes. To achieve knockdown (KD) of Sghrt in CMs in mouse, AAV9 containing cardiac troponin T (cTnT)-promoted and GFP-tagged siRNA targeting Sghrt (AAV9-cTNT-eGFP-RNAi) were injected into chest cavity of the mice in the dose of $5 \times 10^{13}$ vector genomes (vg)/kg.

Studying the Effect of Sghrt KD on CM Dedifferentiation and Heart Function in TAC and MI Mouse Model To investigate whether in vivo KD of Sghrt induces CM dedifferentiation and rescues cardiac function in diseased models of HF, the mice were given injection of AAV9- cTNT-eGFP-RNAi 4 weeks after TAC surgery and immediately after MI surgery, respectively. AAV9-cTNT-eGFP-LacZ was injected into TAC or MI mice as control. Weekly echo was applied afterwards to track the cardiac function of the mice, including the LV ejection fraction (EF) and fraction shortening (FS). 10 and 14 weeks after TAC surgery, the hearts were harvested and sectioned for histological study and immunofluorescence staining of DAB2, cardiac troponin I (cTNI) and wheat germ agglutinin (WGA) to distinguish cell membrane. The co-localization of DAB2 and cTNI signals were assessed by z-stacking function of confocal microscopy. The number of DAB2$^+$ and cTNI+ cells in each heart section were counted, and the size of the DAB2$^+$ CMs and 3 neighbouring DAB2 CMs were measured and analysed using ImageJ. Similarly, 4 weeks after MI surgery, the hearts were harvested for the same analysis above. Further, to study the effect of Sghrt KD on CM dedifferentiation in postnatal mouse, 7-day-old (P7) mice were given injection of AAV9-cTNT-eGFP-RNAi or AAV9-cTNT-eGFP-LacZ, followed by harvesting and downstream analysis 7 days after injection.

ATP Quantification

ATP quantification in human ES-CMs were perform using ATP Determination Kit (A22066) following instructions provided in the kit.

REFERENCES

1 Malliaras, K. et al. Cardiomyocyte proliferation and progenitor cell recruitment underlie therapeutic regeneration after myocardial infarction in the adult mouse heart. *EMBO molecular medicine* 5, 191-209, doi: 10.1002/emmm.201201737 (2013).

2 Bergmann, O. et al. Evidence for cardiomyocyte renewal in humans. *Science* (New York, N.Y.) 324, 98-102, doi: 10.1126/science. 1164680 (2009).

3 Ali, S. R. et al. Existing cardiomyocytes generate cardiomyocytes at a low rate after birth in mice. *Proceedings of the National Academy of Sciences of the United States of America* 111, 8850-8855, doi: 10.1073/pnas. 1408233111 (2014).

4 Porrello, E. R. et al. Transient regenerative potential of the neonatal mouse heart. *Science* (New York, N.Y.) 331, 1078-1080, doi: 10.1126/science. 1200708 (2011).

5 Senyo, S. E. et al. Mammalian heart renewal by pre-existing cardiomyocytes. *Nature* 493, 433-436, doi: 10.1038/nature11682 (2013).

6 Wang, W. E. et al. Dedifferentiation, Proliferation, and Redifferentiation of Adult Mammalian Cardiomyocytes After Ischemic Injury. *Circulation* 136, 834-848, doi: 10.1161/circulationaha.116.024307 (2017).

7 Jopling, C. et al. Zebrafish heart regeneration occurs by cardiomyocyte dedifferentiation and proliferation. *Nature* 464, 606-609, doi: 10.1038/nature08899 (2010).

8 Engel, F. B. et al. p38 MAP kinase inhibition enables proliferation of adult mammalian cardiomyocytes. *Genes & development* 19, 1175-1187, doi: 10.1101/gad.1306705 (2005).

9 Engel, F. B., Hsieh, P. C., Lee, R. T. & Keating, M. T. FGF1/p38 MAP kinase inhibitor therapy induces cardiomyocyte mitosis, reduces scarring, and rescues function after myocardial infarction. *Proceedings of the National Academy of Sciences of the United States of America* 103, 15546-15551, doi: 10.1073/pnas.0607382103 (2006).

10 Kuhn, B. et al. Periostin induces proliferation of differentiated cardiomyocytes and promotes cardiac repair. *Nature medicine* 13, 962-969, doi: 10.1038/nm1619 (2007).

11 Xin, M. et al. Hippo pathway effector Yap promotes cardiac regeneration. *Proceedings of the National Academy of Sciences of the United States of America* 110, 13839-13844, doi: 10.1073/pnas.1313192110 (2013).

12 Tao, G. et al. Pitx2 promotes heart repair by activating the antioxidant response after cardiac injury. *Nature* 534, 119-123, doi: 10.1038/nature17959 (2016).

13 Leach, J. P. et al. Hippo pathway deficiency reverses systolic heart failure after infarction. *Nature* 550, 260-264, doi: 10.1038/nature24045 (2017).

14 Heallen, T. et al. Hippo signaling impedes adult heart regeneration. *Development* (Cambridge, England) 140, 4683-4690, doi: 10.1242/dev.102798 (2013).

15 Eulalio, A. et al. Functional screening identifies miRNAs inducing cardiac regeneration. *Nature* 492, 376-381, doi: 10.1038/nature11739 (2012).

16 Chen, J. et al. mir-17-92 cluster is required for and sufficient to induce cardiomyocyte proliferation in postnatal and adult hearts. *Circulation research* 112, 1557-1566, doi: 10.1161/circresaha.112.300658 (2013).

17 Yang, Y. et al. MicroRNA-34a Plays a Key Role in Cardiac Repair and Regeneration Following Myocardial Infarction. *Circulation research* 117, 450-459, doi: 10.1161/circresaha.117.305962 (2015).

18 Porrello, E. R. et al. Regulation of neonatal and adult mammalian heart regeneration by the miR-15 family. *Proceedings of the National Academy of Sciences of the United States of America* 110, 187-192, doi: 10.1073/pnas.1208863110 (2013).

19 Aguirre, A. et al. In vivo activation of a conserved microRNA program induces mammalian heart regeneration. *Cell stem cell* 15, 589-604, doi: 10.1016/j.stem.2014.10.003 (2014).

20 Mahmoud, A. I. et al. Meis1 regulates postnatal cardiomyocyte cell cycle arrest. *Nature* 497, 249-253, doi: 10.1038/nature12054 (2013).

21 D'Uva, G. et al. ERBB2 triggers mammalian heart regeneration by promoting cardiomyocyte dedifferentiation and proliferation. *Nature cell biology* 17, 627-638, doi: 10.1038/ncb3149 (2015).

22 Kubin, T. et al. Oncostatin M is a major mediator of cardiomyocyte dedifferentiation and remodeling. *Cell stem cell* 9, 420-432, doi: 10.1016/j.stem.2011.08.013 (2011).

23 Puente, B. N. et al. The oxygen-rich postnatal environment induces cardiomyocyte cell-cycle arrest through DNA damage response. *Cell* 157, 565-579, doi: 10.1016/j.cell.2014.03.032 (2014).

24 Nakada, Y. et al. Hypoxia induces heart regeneration in adult mice. *Nature* 541, 222-227, doi: 10.1038/nature20173 (2017).

25 Kimura, W. et al. Hypoxia fate mapping identifies cycling cardiomyocytes in the adult heart. *Nature* 523, 226-230, doi: 10.1038/nature14582 (2015).

26 Morikawa, Y., Heallen, T., Leach, J., Xiao, Y. & Martin, J. F. Dystrophin-glycoprotein complex sequesters Yap to inhibit cardiomyocyte proliferation. *Nature* 547, 227-231, doi: 10.1038/nature22979 (2017).

27 Bassat, E. et al. The extracellular matrix protein agrin promotes heart regeneration in mice. *Nature* 547, 179-184, doi: 10.1038/nature22978 (2017).

28. Mohamed, T. M. A. et al. Regulation of Cell Cycle to Stimulate Adult Cardiomyocyte Proliferation and Cardiac Regeneration. *Cell* 173, 104-116. e112, doi: 10.1016/j.cell.2018.02.014 (2018).
29. Salamon, I., Saccani Jotti, G. & Condorelli, G. The long noncoding RNA landscape in cardiovascular disease: a brief update. *Current opinion in cardiology* 33, 282-289, doi: 10.1097/hco.0000000000000507 (2018).
30. Devaux, Y. et al. Long noncoding RNAs in cardiac development and ageing. Nature reviews. *Cardiology* 12, 415-425, doi: 10.1038/nrcardio.2015.55 (2015).
31. Wang, Z. et al. The long noncoding RNA Chaer defines an epigenetic checkpoint in cardiac hypertrophy. *Nature medicine* 22, 1131-1139, doi: 10.1038/nm.4179 (2016).
32. Han, P. et al. A long noncoding RNA protects the heart from pathological hypertrophy. *Nature* 514, 102-106, doi: 10.1038/nature 13596 (2014).
33. Viereck, J. et al. Long noncoding RNA Chast promotes cardiac remodeling. *Science translational medicine* 8, 326ra322, doi: 10.1126/scitranslmed.aaf1475 (2016).
34. Greco, S. et al. Increased BACE1-AS long noncoding RNA and beta-amyloid levels in heart failure. *Cardiovascular research* 113, 453-463, doi: 10.1093/cvr/cvx013 (2017).
35. Anderson, D. M. et al. A micropeptide encoded by a putative long noncoding RNA regulates muscle performance. *Cell* 160, 595-606, doi: 10.1016/j.cell.2015.01.009 (2015).
36. Ho, L. & van Dijk, M. ELABELA deficiency promotes preeclampsia and cardiovascular malformations in mice. 357, 707-713, doi: 10.1126/science.aam6607 (2017).
37. Bi, P., Ramirez-Martinez, A., Li, H. & Cannavino, J. Control of muscle formation by the fusogenic micropeptide myomixer. 356, 323-327, doi: 10.1126/science.aam9361 (2017).
38. Anderson, D. M. et al. Widespread control of calcium signaling by a family of SERCA-inhibiting micropeptides. *Science signaling* 9, ra119, doi: 10.1126/scisignal.aaj1460 (2016).
39. See, K., Tan, W. L. W., Lim, E. H. & Tiang, Z. Single cardiomyocyte nuclear transcriptomes reveal a lincRNA-regulated de-differentiation and cell cycle stress-response in vivo. *Nat Commun* 8, 225, doi: 10.1038/s41467-017-00319-8 (2017).
40. Carroll, J., Altman, M. C., Fearnley, I. M. & Walker, J. E. Identification of membrane proteins by tandem mass spectrometry of protein ions. *Proceedings of the National Academy of Sciences of the United States of America* 104, 14330-14335, doi: 10.1073/pnas.0706817104 (2007).
41. Zhang, D. et al. Functional prediction and physiological characterization of a novel short trans-membrane protein 1 as a subunit of mitochondrial respiratory complexes. *Physiological genomics* 44, 1133-1140, doi: 10.1152/physiolgenomics.00079.2012 (2012).
42. Fischer, R. & Kessler, B. M. Gel-aided sample preparation (GASP)—a simplified method for gel-assisted proteomic sample generation from protein extracts and intact cells. *Proteomics* 15, 1224-1229, doi: 10.1002/pmic.201400436 (2015).
43. Jiang, J., Wakimoto, H., Seidman, J. G. & Seidman, C. E. Allele-specific silencing of mutant Myh6 transcripts in mice suppresses hypertrophic cardiomyopathy. *Science* (New York, N.Y.) 342, 111-114, doi: 10.1126/science.1236921 (2013).
44. Lian, X. et al. Directed cardiomyocyte differentiation from human pluripotent stem cells by modulating Wnt/beta-catenin signaling under fully defined conditions. *Nature protocols* 8, 162-175, doi: 10.1038/nprot.2012.150 (2013).
45. Komor, A. C., Kim, Y. B., Packer, M. S., Zuris, J. A. & Liu, D. R. Programmable editing of a target base in genomic DNA without double-stranded DNA cleavage. *Nature* 533, 420-424, doi: 10.1038/nature17946 (2016).
46. Gaudelli, N. M. et al. Programmable base editing of A*T to G*C in genomic DNA without DNA cleavage. *Nature* 551, 464-471, doi: 10.1038/nature24644 (2017).

The invention claimed is:

1. A method of assessing heart function in a subject, the method comprising: determining an expression level of a polypeptide encoded by Sghrt in a sample obtained from the subject; comparing the expression level to a reference expression level, wherein if the expression level exceeds the reference expression level, the subject is considered to have impaired or deteriorated heart function.

2. The method according to claim 1, wherein the reference expression level comprises an expression level of the polypeptide in a healthy population.

3. The method according to claim 1, wherein the reference expression level comprises an expression level of the polypeptide in an earlier sample obtained from the subject.

4. The method according to claim 1, the method further comprising administering to the subject an inhibitor of the polypeptide.

5. The method of claim 1, wherein the impaired heart function is selected from the group consisting of: myocardial infarction, heart failure, coronary artery disease, narrowing of the arteries, heart attack, abnormal heart rhythms, arrhythmias, heart failure, heart valve disease, congenital heart disease, heart muscle disease, cardiomyopathy, pericardial disease, aorta disease, marfan syndrome, genetic cardiomyopathy, non-genetic cardiomyopathy, heart hypertrophy, pressure overload-induced heart dysfunction, and damaged heart tissue.

* * * * *